(12) United States Patent
Callen et al.

(10) Patent No.: US 7,556,920 B2
(45) Date of Patent: Jul. 7, 2009

(54) GENE BNO1 MAPPING TO CHROMOSOME 16Q24.3

(75) Inventors: David Frederick Callen, Malvern (AU); Jason Powell, Cumberland Park (AU); Gabriel Kremmidiotis, Flagstaff Hill (AU); Alison Gardner, Brighton (AU); Joanna Crawford, Stirling (AU); Anthony Bais, Parkholme (AU); Marina Kochetkova, Medindie (AU)

(73) Assignee: Bionomics Limited, Thebarton, South Australia (AU)

( * ) Notice: Subject to any disclaimer, the term of this patent is extended or adjusted under 35 U.S.C. 154(b) by 278 days.

(21) Appl. No.: 11/433,983

(22) Filed: May 15, 2006

(65) Prior Publication Data

US 2006/0211033 A1   Sep. 21, 2006

Related U.S. Application Data

(62) Division of application No. 10/470,700, filed on Jul. 29, 2003, now Pat. No. 7,083,927.

(30) Foreign Application Priority Data

Jan. 31, 2001  (AU) .................................. PR2783
Jan. 31, 2002  (AU) ..................... PCT/AU02/00096

(51) Int. Cl.
    *C07K 14/00* (2006.01)
(52) U.S. Cl. .......................................... 435/6; 530/350
(58) Field of Classification Search ................ 530/350
    See application file for complete search history.

(56) References Cited

U.S. PATENT DOCUMENTS 6,569,662 B1  5/2003  Tang et al.
7,083,927 B2  8/2006  Callen et al.

FOREIGN PATENT DOCUMENTS

WO   WO 01/53312        7/2001
WO      02/081514 A2   10/2002
WO      02/103320 A2   12/2002
WO      03/012103 A3    2/2003

OTHER PUBLICATIONS

Baumeister et al., "The Proteasome: Paradigm of a Self-Compartmentalizing Protease," *Cell*, 92:367-380 (Feb. 6, 1998).
Brenner et al., "Chromosome 9p Allelic Loss and *p. 16/CDKN2* in Breast Cancer and Evidence of *p/16* Inactivation in Immortal Breast Epithelial Cells," *Cancer Research*, 55:2892-2895 (Jul. 1, 1995).
Cenciarelli et al., "Identification of a family of human F-box proteins," *Current Biology*, 9(20):1177-1179 (Oct. 11, 1999).
Chen et al., "Deletion Map of Chromosome 16q in Ductal Carcinoma in Situ of the Breast: Refining a Putative Tumor Suppressor Gene Region," *Cancer Research*, 56:5605-5609 (Dec. 15, 1996).
Cleton-Jansen et al., "Loss of heterozygosity in sporadic breast tumours at the *BRCA2* locus on chromosome 13q12-q13," *British Journal of Cancer*, 72:1241-1244 (1995).
Cockman et al., "Hypoxia Inducible Factor-α Binding and Ubiquitylation by the von Hippel-Lindau Tumor Suppressor Protein," *Journal of Biological Chemistry*, 275(33):25733-25741 (Aug. 18, 2000).
Devilee et al., "Somatic genetic changes in human breast cancer," *Biochimica et Biophysica Acta*, 1198:113-130 (1994).
Drobnjak, et al., *Altered Expression of p27 and Skp2 Proteins in Prostate Cancer of African-American Patients*, Clinical Cancer Research 9:263-2619 (Jul. 2003).
*EMBL* database Accession No. AL117444.
Esteller et al., "Promoter Hypermethylation and BRCA1 Inactivation in Sporadic Breast and Ovarian Tumors," *Journal of the National Cancer Institute*, 92(7):564-569 (Apr. 5, 2000).
Fearon et al., "A Genetic Model for Colorectal Tumorigenesis," *Cell*, 61:759-767 (Jun. 1, 1990).
Futreal et al., "*BRCA1* Mutations in Primary Breast and Ovarian Carcinomas," *Science*, 266: (Oct. 7, 1994).
Haas et al., "Pathways of ubiquitin conjugation," *FASEB J.*, 11:1257-1268 (1997).
Hall et al., "Linkage of Early-Onset Familial Breast Cancer to Chromosome 17q21," *Science*, 250:1684-1689 (Dec. 21, 1990).
Herman et al., "Incidence and functional consequences of *hMLH1* promoter hypermethylation in colorectal carcinoma," *Proc. Natl. Acad. Sci. USA*, 95:6870-6875 (Jun. 1998).
Hershko et al., "The Ubiquitin System," *Annu. Rev. Biochem.*, 67:425-479 (1998).
International for Corresponding PCT Appl. No. PCT/AU02/00096 dated Mar. 22, 2002.
Kipreos et al., "The F-box protein family," *Genome Biology*, 1(5):3002.1-3002.7 (Nov. 10, 2000).
Koehrer K. et al., "*Homo sapiens* mRNA; cDNA DKFZp434B027(from clone DKFZp434B027", GenPept database Accession No. CAB55929 (Sep. 15, 1999).
Koehrer K. et al., "Hypothetical protein DKFZp434B027.1-human (fragment)"; *PIR* database Accession No. T17239 (Oct. 15, 1999).
Li et al., "Ubiquitination of A Novel Deubiquitinating Enzyme Requires Direct Binding to von Hippel-Lindau Tumor Suppressor Protein," Am. Soc. for Biochem. and Molecu. Bio., pp. 1-22 (Dec. 5, 2001).
Lopez Salon et al., "Defective Ubiquitination of Cerebral Proteins in Alzheimer's Disease," *Journal of Neuroscience Research*, 63:302-310 (2000).
Miki et al., "A Strong Candidate for the Breast and Ovarian Cancer Susceptibility Gene *BRCA1*," *Science*, 266:66-71 (Oct. 7, 1994).
Miki et al., "Mutation analysis in the *BRCA2i* gene in primary breast cancers," *Nature Genetics*, 13:245-247 (Jun. 1996).

(Continued)

*Primary Examiner*—Brandon J Fetterolf
(74) *Attorney, Agent, or Firm*—Jenkins, Wilson, Taylor & Hunt, P.A.

(57) ABSTRACT

An isolated nucleic acid molecule mapping to chromosome 16q24.3 and comprising the nucleotide sequence set forth in SEQ ID Numbers: 1 or 3.

4 Claims, 4 Drawing Sheets

OTHER PUBLICATIONS

Ohh et al., "Ubiquitination of hypoxia-inducible factor requires direct binding to the β-domain of the von Hippel-Lindau protein," Nature Cell Biology, 2:423-427 (Jul. 2000).

Ohtani-Fujita et al., "Hypermethylation in the Retinoblastoma Gene Is Associated with Unilateral, Sporadic Retinoblastoma," Cancer Genet Cytogenet, 98:43-49 (1997).

Osada et al., Mus musculus brain cDNA, clone MNCb-2609, similar to *Homo sapiens* mRNA; cDNA DKFZp434B027 (from clone DKFZp434B027), GenPept database Accession No. BAA95069 & EMBL database Accession No. AB041586 (Apr. 30, 2000).

Peters, "SCF and APC: the Yin and Yang of cell cycle regulated proteolysis," Current Opinion in Cell Biology, 10:759-768 (1998).

Powell et al., "Sequencing, Transcript Identification, and Quantitative Gene Expression Profiling in the Breast Cancer Loss of Heterozygosity Region 16q24.3 Reveal Three Potential Tumor Suppressor Genes," Genomics, 80(3):303-310 (Sep. 2002).

Prowse et al., "Somatic Inactivation of the VHL Gene in Von Hippel-Lindau Disease Tumors," Am. J. Hum. Genet., 60:765-771 (1997).

Radford et al., "Allelotyping of Ductal Carcinoma in Situ of the Breast: Deletion of Loci on 8p, 13q, 16q, 17p and 17q," Cancer Research, 55:3399-3405 (Aug. 1, 1995).

Saito et al., "Detailed Deletion Mapping of Chromosome 17q in Ovarian and Breast Cancers: 2-cM Region on 17q21.3 Often and Commonly Deleted in Tumors," Cancer Research, 53:3382-3385 (Jul. 15, 1993).

Semenza, "HIF-1 and human disease: one highly involved factor," Genes & Development, 14:1983-1991 (2000).

Shimura et al., "Ubiquitination of a New Form of α-Synuclein by Parkin from Human Brain: Implications for Parkinson's Disease," Science, 293:263-269 (Jul. 13, 2001).

Strausberg, R., "*Homo sapiens*, clone MGC:15419 IMAGE: 3958783, mRNA", GenPept database Accession No. AAH12748 & GenBank database Accession No. BC012748 (Sep. 20, 2001).

Supplementary Search Report from the European Patent Office for corresponding European application 02 71 1634 dated Apr. 1, 2004.

van 't Veer et al., "Gene expression profiling predicts clinical outcome of breast cancer," Nature, 415:530-536 (Jan. 31, 2002).

Wang et al., "Hypoxia-inducible factor 1 is a basic-helix-loop-helix-PAS heterodimer regulated by cellular $O_2$ tension," Proc. Natl. Acad. Sci. USA, 92:5510-5514 (Jun. 1995).

Winston et al., "A family of mammalian F-box proteins," Current Biology, 9:1180-1182 (Oct. 11, 1999).

Wooster et al., "Localization of a Breast Cancer Susceptibility Gene, *BRCA2*, to Chromosome 13q12-13," Science, 265:2088-2090 (Sep. 30, 1994).

Wooster et al., "Identification of the breast cancer susceptibility gene *BRCA2*," Nature, 378(21):789-792 (Dec. 28, 1995).

Zhou, et al.; "*Homo sapiens* pp2386 mRNA"; GenPept database Accession No. AAL55855 & GenBank database Accession No. AF318348 (Jan. 1, 2002).

Notice of Allowance for Parent Patent No. 7,083,927 dated Mar. 28, 2006.

Office Communication for Parent Patent No. 7,083,927 dated Sep. 22, 2005.

Office Communication for Parent Patent No. 7,083,927 dated May 11, 2005.

Restriction/Election Requirement for Parent Patent No. 7,083,927 dated Jan. 31, 2005.

BNO1  -RCSLLELPPELLVEIFASLPGTDLPSLAQVCTKFRRILHTDTIWRRR-- (SEQ ID NO: 84)
      kPFPLLRLPeEIlrKILeKILrKIleklDPidDLLrLRKVsKKWRsLVDslnlwfkfIe (SEQ ID NO: 85)

GENE BNO1 MAPPING TO CHROMOSOME 16Q24.3

RELATED APPLICATIONS

This application is a divisional patent application which claims the benefit of the filing date of U.S. patent application Ser. No. 10/470,700, filed Jul. 29, 2003 and now issued U.S. Pat. No. 7,083,927, which claims benefit to PCT International Patent Application Ser. No. PCT/AU01/00729, filed Jul. 29, 2003, the disclosures of which are incorporated herein by reference in their entirety.

TECHNICAL FIELD

The present invention relates to a novel gene which has been identified at the distal tip of the long arm of chromosome 16 at 16q24.3. The BNO1 gene encodes a polypeptide that forms part of a ubiquitin-ligase complex involved in targeting proteins by ubiquitination for degradation by the proteasome. In view of the realisation that BNO1 is involved in ubiquitination and protein degradation, the invention is also concerned with the therapy of disorders associated with this process, such as cancer (in particular breast and prostate carcinoma), immune/inflammatory disease and neurological disease. In addition, the invention is concerned with the diagnosis of disorders associated with ubiquitination and the screening of drugs for therapeutic intervention in these disorders.

BACKGROUND ART

The development of human carcinomas has been shown to arise from the accumulation of genetic changes involving both positive regulators of cell function (oncogenes) and negative regulators (tumour suppressor genes). For a normal somatic cell to evolve into a metastatic tumour it requires changes at the cellular level, such as immortalisation, loss of contact inhibition and invasive growth capacity, and changes at the tissue level, such as evasion of host immune responses and growth restraints imposed by surrounding cells, and the formation of a blood supply for the growing tumour.

Molecular genetic studies of colorectal carcinoma have provided substantial evidence that the generation of malignancy requires the sequential accumulation of a number of genetic changes within the same epithelial stem cell of the colon. For a normal colonic epithelial cell to become a benign adenoma, progress to intermediate and late adenomas, and finally become a malignant cell, inactivating mutations in tumour suppressor genes and activating mutations in proto-oncogenes are required (Fearon and Vogelstein, 1990).

The employment of a number of techniques, such as loss of heterozygosity (LOH), comparative genomic hybridisation (CGH) and cytogenetic studies of cancerous tissue, all of which exploit chromosomal abnormalities associated with the affected cell, has aided in the identification of a number of tumour suppressor genes and oncogenes associated with a range of tumour types.

In one aspect, studies of cancers such as retinoblastoma and colon carcinoma have supported the model that LOH is a specific event in the pathogenesis of cancer and has provided a mechanism in which to identify the cancer causing genes. This model is further highlighted in Von Hippel-Lindau (VHL) syndrome, a rare disorder that predisposes individuals to a variety of tumours including clear cell carcinomas of the kidneys and islet cell tumours of the pancreas. Both sporadic and inherited cases of the syndrome show LOH for the short arm of chromosome 3 and somatic translocations involving 3p in sporadic tumours, and genetic linkage to the same region in affected families has also been observed. The VHL tumour suppressor gene has since been identified from this region of chromosome 3 and mutations in it have been detected in 100% of patients who carry a clinical diagnosis of VHL disease. In addition, the VHL gene is inactivated in approximately 50-80% of the more common sporadic form of renal clear cell carcinoma.

The genetic determinants involved in breast cancer are not as well defined as that of colon cancer due in part to the histological stages of breast cancer development being less well characterised. However, as with colon carcinoma, it is believed that a number of genes need to become involved in a stepwise progression during breast tumourigenesis.

Certain women appear to be at an increased risk of developing breast cancer. Genetic linkage analysis has shown that 5 to 10% of all breast cancers are due to at least two autosomal dominant susceptibility genes. Generally, women carrying a mutation in a susceptibility gene develop breast cancer at a younger age compared to the general population, often have bilateral breast tumours, and are at an increased risk of developing cancers in other organs, particularly carcinoma of the ovary.

Genetic linkage analysis on families showing a high incidence of early-onset breast cancer (before the age of 46) was successful in mapping the first susceptibility gene, BRCA1, to chromosome 17q21 (Hall et al., 1990). Subsequent to this, the BRCA2 gene was mapped to chromosome 13q12-q13 (Wooster et al., 1994) with this gene conferring a higher incidence of male breast cancer and a lower incidence of ovarian cancer when compared to BRCA1.

Both BRCA1 and BRCA2 have since been cloned (Miki et al., 1994; Wooster et al., 1995) and numerous mutations have been identified in these genes in susceptible individuals with familial cases of breast cancer.

Additional inherited breast cancer syndromes exist, however they are rare. Inherited mutations in the TP53 gene have been identified in individuals with Li-Fraumeni syndrome, a familial cancer resulting in epithelial neoplasms occurring at multiple sites including the breast. Similarly, germline mutations in the MMAC1/PTEN gene involved in Cowden's disease and the ataxia telangiectasia (AT) gene have been shown to confer an increased risk of developing breast cancer, among other clinical manifestations, but together account for only a small percentage of families with an inherited predisposition to breast cancer.

Somatic mutations in the TP53 gene have been shown to occur in a high percentage of individuals with sporadic breast cancer. However, although LOH has been observed at the BRCA1 and BRCA2 loci at a frequency of 30 to 40% in sporadic cases (Cleton-Jansen et al., 1995; Saito et al., 1993), there is virtually no sign of somatic mutations in the retained allele of these two genes in sporadic cancers (Futreal et al., 1994; Miki et al., 1996). Recent data suggests that DNA methylation of the promoter sequence of these genes may be an important mechanism of down-regulation. The use of both restriction fragment length polymorphisms and small tandem repeat polymorphic markers has identified numerous regions of allelic imbalance in breast cancer suggesting the presence of additional genes, which may be implicated in breast cancer. Data compiled from more than 30 studies reveals the loss of DNA from at least 11 chromosome arms at a frequency of more than 25%, with regions such as 16q and 17p affected in more than 50% of tumours (Devilee and Cornelisse, 1994; Brenner and Aldaz, 1995). However only some of these regions are known to harbour tumour suppressor genes shown to be mutated in individuals with both sporadic (TP53 and RB genes) and familial (TP53, RB, BRCA1, and BRCA2 genes) forms of breast cancer.

Cytogenetic studies have implicated loss of the long arm of chromosome 16 as an early event in breast carcinogenesis since it is found in tumours with few or no other cytogenetic abnormalities. Alterations in chromosome 1 and 16 have also been seen in several cases of ductal carcinoma in situ (DCIS), the preinvasive stage of ductal breast carcinoma. In addition, LOH studies on DCIS samples identified loss of 16q markers in 29 to 89% of the cases tested (Chen et al., 1996; Radford et al., 1995). In addition, examination of tumours from other tissue types have indicated that 16q LOH is also frequently seen in prostate, liver, ovarian and primitive neuroectodermal carcinomas. Together, these findings suggest the presence of a gene mapping to the long arm of chromosome 16 that is critically involved in the early development of a large proportion of breast cancers as well as cancers from other tissue types, but to date no such gene has been identified.

DISCLOSURE OF THE INVENTION

The present invention provides an isolated nucleic acid molecule mapping to chromosome 16q24.3 comprising the nucleotide sequence set forth in SEQ ID Numbers: 1 or 3.

It also provides an isolated nucleic acid molecule comprising the nucleotide sequence set forth in SEQ ID Numbers: 1 or 3, or a fragment thereof, which encodes a polypeptide that forms part of a ubiquitin-ligase complex involved in targeting proteins by ubiquitination for degradation by the proteasome.

The invention also encompasses an isolated nucleic acid molecule that is at least 70% identical to a DNA molecule consisting of the nucleotide sequence set forth in SEQ ID Numbers: 1 or 3 and which encodes a polypeptide that forms part of a ubiquitin-ligase complex involved in targeting proteins by ubiquitination for degradation by the proteasome.

Such variants will have preferably at least about 85%, and most preferably at least about 95% sequence identity to the nucleotide sequence encoding BNO1. A particular aspect of the invention encompasses a variant of SEQ ID Numbers: 1 or 3 which has at least about 70%, more preferably at least about 85%, and most preferably at least about 95% sequence identity to SEQ ID Numbers: 1 or 3. Any one of the polynucleotide variants described above can encode an amino acid sequence, which contains at least one functional or structural characteristic of BNO1.

Typically, sequence identity is calculated using the BLASTN algorithm with the BLOSSUM62 default matrix.

The invention also encompasses an isolated nucleic acid molecule that encodes a polypeptide that forms part of a ubiquitin-ligase complex involved in protein degradation through ubiquitination, and which hybridizes under stringent conditions with a DNA molecule consisting of the nucleotide sequence set forth in SEQ ID Numbers: 1 or 3.

Under stringent conditions, hybridization will most preferably occur at 42° C. in 750 mM NaCl, 75 mM trisodium citrate, 2% SDS, 50% formamide, 1× Denhart's, 10% (w/v) dextran sulphate and 100 µg/ml denatured salmon sperm DNA. Useful variations on these conditions will be readily apparent to those skilled in the art. The washing steps which follow hybridization most preferably occur at 65° C. in 15 mM NaCl, 1.5 mM trisodium citrate, and 1% SDS. Additional variations on these conditions will be readily apparent to those skilled in the art The invention also provides an isolated nucleic acid molecule which encodes a polypeptide having the amino acid sequence set forth in SEQ ID Numbers: 2 or 4.

Still further, the invention encompasses an isolated nucleic acid molecule wherein the encoded amino acid sequence has at least 70%, preferably 85%, and most preferably 95%, sequence identity to the sequence set forth in SEQ ID Numbers: 2 or 4.

Preferably, sequence identity is determined using the BLASTP algorithm with the BLOSSUM62 default matrix.

In a further aspect, there is provided an isolated nucleic acid molecule comprising exons 1 to 9 or exons 1, 2, 2.5, and 3 to 9 identified in the nucleotide sequences set forth in SEQ ID Numbers: 1 and 3 respectively.

Still further, there is provided an isolated nucleic acid molecule consisting of the nucleotide sequence set forth in SEQ ID Numbers: 1 or 3.

In a still further aspect, there is provided an isolated nucleic acid molecule consisting of the nucleotide sequence set forth in SEQ ID NO: 1 from base 4 to base 1,621 or set forth in SEQ ID NO: 3 from base 4 to base 1,708.

In a further aspect, the invention provides an isolated gene comprising the nucleotide sequence set forth in SEQ ID Numbers: 1 or 3 and BNO1 control elements.

Preferably, the BNO1 control elements are those which mediate expression in breast, prostate, liver and ovarian tissue.

The nucleotide sequences of the present invention can be engineered using methods accepted in the art so as to alter BNO1-encoding sequences for a variety of purposes. These include, but are not limited to, modification of the cloning, processing, and/or expression of the gene product. PCR reassembly of gene fragments and the use of synthetic oligonucleotides allow the engineering of BNO1 nucleotide sequences. For example, oligonucleotide-mediated site-directed mutagenesis can introduce mutations that create new restriction sites, alter glycosylation patterns and produce splice variants etc.

As a result of the degeneracy of the genetic code, a number of polynucleotide sequences encoding BNO1, some that may have minimal similarity to the polynucleotide sequences of any known and naturally occurring gene, may be produced. Thus, the invention includes each and every possible variation of polynucleotide sequence that could be made by selecting combinations based on possible codon choices. These combinations are made in accordance with the standard triplet genetic code as applied to the polynucleotide sequence of naturally occurring BNO1, and all such variations are to be considered as being specifically disclosed.

The polynucleotides of this invention include RNA, cDNA, genomic DNA, synthetic forms, and mixed polymers, both sense and antisense strands, and may be chemically or biochemically modified, or may contain non-natural or derivatised nucleotide bases as will be appreciated by those skilled in the art. Such modifications include labels, methylation, intercalators, alkylators and modified linkages. In some instances it may be advantageous to produce nucleotide sequences encoding BNO1 or its derivatives possessing a substantially different codon usage than that of the naturally occurring BNO1. For example, codons may be selected to increase the rate of expression of the peptide in a particular prokaryotic or eukaryotic host corresponding with the frequency that particular codons are utilized by the host. Other reasons to alter the nucleotide sequence encoding BNO1 and its derivatives without altering the encoded amino acid sequences include the production of RNA transcripts having more desirable properties, such as a greater half-life, than transcripts produced from the naturally occurring sequence.

The invention also encompasses production of DNA molecules, which encode BNO1 and its derivatives, or fragments thereof, entirely by synthetic chemistry. Synthetic sequences may be inserted into expression vectors and cell systems that contain the necessary elements for transcriptional and translational control of the inserted coding sequence in a suitable host. These elements may include regulatory sequences, promoters, 5' and 3' untranslated regions and specific initiation signals (such as an ATG initiation codon and Kozak consensus sequence) which allow more efficient translation of sequences encoding BNO1. In cases where the complete BNO1 coding sequence including its initiation codon and upstream regulatory sequences are inserted into the appropriate expression vector, additional control signals may not be needed. However, in cases where only coding sequence, or a fragment thereof, is inserted, exogenous translational control signals as described above should be provided by the vector. Such signals may be of various origins, both natural and synthetic. The efficiency of expression may be enhanced by the inclusion of enhancers appropriate for the particular host cell system used (Scharf et al., 1994).

The present invention allows for the preparation of purified BNO1 polypeptide or protein, from the polynucleotides of the present invention or variants thereof. In order to do this, host cells may be transfected with a DNA molecule as described above. Typically said host cells are transfected with an expression vector comprising a DNA molecule according to the invention. A variety of expression vector/host systems may be utilized to contain and express sequences encoding BNO1. These include, but are not limited to, microorganisms such as bacteria transformed with plasmid or cosmid DNA expression vectors; yeast transformed with yeast expression vectors; insect cell systems infected with viral expression vectors (e.g., baculovirus); or mouse or other animal or human tissue cell systems. Mammalian cells can also be used to express the BNO1 protein using various expression vectors including plasmid, cosmid and viral systems such as adenoviral, retroviral or vaccinia virus expression systems. The invention is not limited by the host cell employed.

The polynucleotide sequences, or variants thereof, of the present invention can be stably expressed in cell lines to allow long term production of recombinant proteins in mammalian systems. Sequences encoding BNO1 can be transformed into cell lines using expression vectors which may contain viral origins of replication and/or endogenous expression elements and a selectable marker gene on the same or on a separate vector. The selectable marker confers resistance to a selective agent, and its presence allows growth and recovery of cells which successfully express the introduced sequences. Resistant clones of stably transformed cells may be propagated using tissue culture techniques appropriate to the cell type.

The protein produced by a transformed cell may be secreted or retained intracellularly depending on the sequence and/or the vector used. As will be understood by those of skill in the art, expression vectors containing polynucleotides which encode BNO1 may be designed to contain signal sequences which direct secretion of BNO1 through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, glycosylation, phosphorylation, and acylation. Post-translational cleavage of a "prepro" form of the protein may also be used to specify protein targeting, folding, and/or activity. Different host cells having specific cellular machinery and characteristic mechanisms for post-translational activities (e.g., CHO or HeLa cells), are available from the American Type Culture Collection (ATCC) and may be chosen to ensure the correct modification and processing of the foreign protein.

When large quantities of BNO1 are needed such as for antibody production, vectors which direct high levels of expression of BNO1 may be used such as those containing the T5 or T7 inducible bacteriophage promoter. The present invention also includes the use of the expression systems described above in generating and isolating fusion proteins which contain important functional domains of the protein. These fusion proteins are used for binding, structural and functional studies as well as for the generation of appropriate antibodies.

In order to express and purify the protein as a fusion protein, the appropriate BNO1 cDNA sequence is inserted into a vector which contains a nucleotide sequence encoding another peptide (for example, glutathionine succinyl transferase). The fusion protein is expressed and recovered from prokaryotic or eukaryotic cells. The fusion protein can then be purified by affinity chromatography based upon the fusion vector sequence and the BNO1 protein obtained by enzymatic cleavage of the fusion protein.

Fragments of BNO1 may also be produced by direct peptide synthesis using solid-phase techniques. Automated synthesis may be achieved by using the ABI 431A Peptide Synthesizer (Perkin-Elmer). Various fragments of BNO1 may be synthesized separately and then combined to produce the full-length molecule.

According to the invention there is provided an isolated polypeptide comprising the amino acid sequence set forth in SEQ ID Numbers: 2 or 4.

According to a still further aspect of the invention there is provided an isolated polypeptide, comprising the amino acid sequence set forth in SEQ ID Numbers: 2 or 4, or a fragment thereof, that forms part of a ubiquitin-ligase complex involved in protein degradation through ubiquitination.

The invention also encompasses an isolated polypeptide that forms part of a ubiquitin-ligase complex involved in protein degradation through ubiquitination that has at least 70%, preferably 85%, and more preferably 95%, identity with the amino acid sequence set forth in SEQ ID Numbers: 2 or 4.

Preferably, sequence identity is determined using the BLASTP algorithm with the BLOSSUM62 default matrix.

Also envisaged is an isolated polypeptide consisting of the amino acid sequence set forth in SEQ ID Numbers: 2 or 4.

In a further aspect of the invention there is provided a method of preparing a polypeptide as described above, comprising the steps of:

(1) culturing the host cells under conditions effective for production of the polypeptide; and (2) harvesting the polypeptide.

Substantially purified BNO1 protein or fragments thereof can then be used in further biochemical analyses to establish secondary and tertiary structure for example by x-ray crystallography of BNO1 protein or by nuclear magnetic resonance (NMR). Determination of structure allows for the rational design of pharmaceuticals to interact with the protein, alter protein charge configuration or charge interaction with other proteins, or to alter its function in the cell.

The BNO1 gene has been identified from a region of restricted LOH seen in breast and prostate cancer and appears to be down regulated in its expression in cancer cell lines derived from these tissues. In addition, chemical and structural similarity in the context of sequences and motifs, exists between regions of BNO1 and F-box proteins. F-box proteins are the substrate recognition components of one class of ubiquitin-E3 ligases, the so called "SCF" class, which are involved in the degradation of proteins through ubiquitination and subsequent proteolysis carried out by the proteasome. To date, proteins shown to be regulated by this mechanism include oncogenes, tumour suppressor genes, transcription factors and other signalling molecules. These proteins influence many cellular processes such as modulation of the immune and inflammatory responses, development and differentiation, as well as processes that are involved in cancer development such as cell-cycle regulation and apoptosis. BNO1 has also been shown to interact with Skp1, an essential component of SCF ubiquitin-E3 ligases.

A strong precedent for a tumour suppressor protein belonging to the ubiquitin-proteasome degradation system has previously been provided by the VHL gene. This gene has been demonstrated to associate with elongin C, elongin B, and cullin-2 in a complex termed VCB-CUL-2. This multiprotein complex exhibits structural and functional similarity to SCF ubiquitin ligases and has been shown to be involved in the ubiquitination of VHL substrates.

Collectively, this information suggests BNO1 is involved in the processes that lead to cancer, particularly breast and prostate carcinoma, most likely through its role in the ubiquitination of proteins involved in important cellular functions such as cell cycle regulation. As BNO1 is expressed in many tissue types, alterations in BNO1 function may also cause pathologies in these tissues through consequential abnormalities in the ubiquitination process.

With the identification of the BNO1 nucleotide and protein sequence, probes and antibodies raised to the gene can be used in a variety of hybridisation and immunological assays to screen for and detect the presence of either a normal or mutated gene or gene product. In addition the nucleotide and protein sequence of the BNO1 gene provided in this invention enables therapeutic methods for the treatment of all diseases associated with abnormalities of BNO1 function, including cancer, immune/inflammatory disease and neurological disorders, and also enables methods for the diagnosis or prognosis of all diseases associated with abnormalities of BNO1 function.

Examples of such disorders include, but are not limited to, cancers, immune/inflammatory disorders and neurological disorders. Cancers include adenocarcinoma, leukemia, lymphoma, melanoma, myeloma, sarcoma, teratocarcinoma, and, in particular, cancers of the breast, prostate, liver, ovary, head and neck, heart, brain, pancreas, lung, skeletal muscle, kidney, colon, uterus, testis, adrenal gland, blood, germ cells, placenta, synovial membrane, tonsil, cervix, lymph tissue, skin, bladder, spinal cord, thyroid gland and stomach. Other cancers may include those of the bone, bone marrow, gall bladder, ganglia, gastrointestinal tract, parathyroid, penis, salivary glands, spleen and thymus. Immune/inflammatory disorders include acquired immunodeficiency syndrome (AIDS), Addison's disease, adult respiratory distress syndrome, allergies, ankylosing spondylitis, amyloidosis, anemia, asthma, atherosclerosis. autoimmune hemolytic anemia, autoimmune thyroiditis, autoimmune polyenodocrinopathy-candidiasis-ectodermal dystrophy (APECED), bronchitis, cholecystitis, contact dermatitis, Crohn's disease, cystic fibrosis, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of wound healing (eg scarring), cancer, hemodialysis, and extracorporeal circulation, viral, bacterial, fungal, parasitic, protozoal, and helminthic infections, and trauma. Neurological disorders may include Parkinson's disease and Alzheimer's disease.

In the treatment of diseases associated with decreased BNO1 expression and/or activity, it is desirable to increase the expression and/or activity of BNO1. In the treatment of disorders associated with increased BNO1 expression and/or activity, it is desirable to decrease the expression and/or activity of BNO1.

Enhancing BNO1 Gene or Protein Function

Enhancing, stimulating or re-activating BNO1 gene or protein function can be achieved in a variety of ways. In one aspect of the invention administration of an isolated DNA molecule, as described above, to a subject in need of such treatment may be initiated.

Typically, BNO1 is administered to a subject to treat or prevent a disorder associated with decreased activity and/or expression of BNO1.

In a further aspect, there is provided the use of an isolated DNA molecule, as described above, in the manufacture of a medicament for the treatment of a disorder associated with decreased activity and/or expression of BNO1.

Typically, a vector capable of expressing BNO1 or a fragment or derivative thereof may be administered to a subject to treat or prevent a disorder associated with decreased activity and/or expression of TSG18 including, but not limited to, those described above. Transducing retroviral vectors are often used for somatic cell gene therapy because of their high efficiency of infection and stable integration and expression. The full length BNO1 gene, or portions thereof, can be cloned into a retroviral vector and driven from its endogenous promoter or from the retroviral long terminal repeat or from a promoter specific for the target cell type of interest. Other viral vectors can be used and include, as is known in the art, adenoviruses, adeno-associated virus, vaccinia virus, papovaviruses, lentiviruses and retroviruses of avian, murine and human origin.

Gene therapy would be carried out according to established methods (Friedman, 1991; Culver, 1996). A vector containing a copy of the BNO1 gene linked to expression control elements and capable of replicating inside the cells is prepared. Alternatively the vector may be replication deficient and may require helper cells or helper virus for replication and virus production and use in gene therapy.

Gene transfer using non-viral methods of infection can also be used. These methods include direct injection of DNA, uptake of naked DNA in the presence of calcium phosphate, electroporation, protoplast fusion or liposome delivery. Gene transfer can also be achieved by delivery as a part of a human artificial chromosome or receptor-mediated gene transfer. This involves linking the DNA to a targeting molecule that will bind to specific cell-surface receptors to induce endocytosis and transfer of the DNA into mammalian cells. One such technique uses poly-L-lysine to link asialoglycoprotein to DNA. An adenovirus is also added to the complex to disrupt the lysosomes and thus allow the DNA to avoid degradation and move to the nucleus. Infusion of these particles intravenously has resulted in gene transfer into hepatocytes.

In affected subjects that express a mutated form of BNO1 it may be possible to prevent the disorder by introducing into the affected cells a wild-type copy of the gene such that it recombines with the mutant gene. This requires a double recombination event for the correction of the gene mutation.

Vectors for the introduction of genes in these ways are known in the art, and any suitable vector may be used. Alternatively, introducing another copy of the gene bearing a second mutation in that gene may be employed so as to negate the original gene mutation and block any negative effect.

In affected subjects that have decreased expression of BNO1, a mechanism of down-regulation may be abnormal methylation of the CpG island present in the 5' end of the gene. Therefore, in an alternative approach to therapy, administration of agents that remove BNO1 promoter methylation will reactivate BNO1 gene expression and may suppress the associated disease phenotype.

In a further aspect, a suitable agonist may also include a small molecule or peptide that can mimic the function of wild-type BNO1.

Inhibiting BNO1 Gene or Protein Function

Inhibiting the function of a mutated gene or protein can be achieved in a variety of ways. In one aspect of the invention there is provided a method of treating a disorder associated with increased activity and/or expression of BNO1, comprising administering an antagonist of BNO1 to a subject in need of such treatment.

In still another aspect of the invention there is provided the use of an antagonist of BNO1 in the manufacture of a medicament for the treatment of a disorder associated with increased activity and/or expression of BNO1.

Such disorders may include, but are not limited to, those discussed above. In one aspect of the invention an isolated DNA molecule, which is the complement of any one of the DNA molecules described above and which encodes an RNA molecule that hybridises with the mRNA encoded by BNO1, may be administered to a subject in need of such treatment.

In a still further aspect of the invention there is provided the use of an isolated DNA molecule which is the complement of a DNA molecule of the invention and which encodes an RNA molecule that hybridises with the mRNA encoded by BNO1, in the manufacture of a medicament for the treatment of a disorder associated with increased activity and/or expression of BNO1.

Typically, a vector expressing the complement of the polynucleotide encoding BNO1 may be administered to a subject to treat or prevent a disorder associated with increased activity and/or expression of BNO1 including, but not limited to, those described above. Antisense strategies may use a variety of approaches including the use of antisense oligonucleotides, ribozymes, DNAzymes, injection of antisense RNA and transfection of antisense RNA expression vectors. Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (For example, see Goldman et al., 1997).

According to still another aspect of the invention, there is provided a method of treating a disorder associated with increased activity and/or expression of BNO1 comprising administering an antagonist of BNO1 to a subject in need of such treatment.

In still another aspect of the invention there is provided the use of an antagonist of BNO1 in the manufacture of a medicament for the treatment of a disorder associated with increased activity and/or expression of BNO1.

Such disorders may include, but are not limited to, those discussed above. In one aspect purified protein according to the invention may be used to produce antibodies which specifically bind BNO1. These antibodies may be used directly as an antagonist or indirectly as a targeting or delivery mechanism for bringing a pharmaceutical agent to cells or tissues that express BNO1. Such antibodies may include, but are not limited to, polyclonal, monoclonal, chimeric and single chain antibodies as would be understood by the person skilled in the art.

For the production of antibodies, various hosts including rabbits, rats, goats, mice, humans, and others may be immunized by injection with a protein of the invention or with any fragment or oligopeptide thereof, which has immunogenic properties. Various adjuvants may be used to increase immunological response and include, but are not limited to, Freund's, mineral gels such as aluminum hydroxide, and surface-active substances such as lysolecithin. Adjuvants used in humans include BCG (bacilli Calmette-Guerin) and *Corynebacterium parvum*.

It is preferred that the oligopeptides, peptides, or fragments used to induce antibodies to BNO1 have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of amino acids from these proteins may be fused with those of another protein, such as KLH, and antibodies to the chimeric molecule may be produced.

Monoclonal antibodies to BNO1 may be prepared using any technique which provides for the production of antibody molecules by continuous cell lines in culture. These include, but are not limited to, the hybridoma technique, the human B-cell hybridoma technique, and the EBV-hybridoma technique. (For example, see Kohler et al., 1975; Kozbor et al., 1985; Cote et al., 1983; Cole et al., 1984).

Antibodies may also be produced by inducing in vivo production in the lymphocyte population or by screening immunoglobulin libraries or panels of highly specific binding reagents as disclosed in the literature. (For example, see Orlandi et al., 1989; Winter et al., 1991).

Antibody fragments which contain specific binding sites for BNO1 may also be generated. For example, such fragments include, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (For example, see Huse et al., 1989).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between a protein and its specific antibody. A two-site, monoclonal-based immunoassay utilizing monoclonal antibodies reactive to two non-interfering epitopes is preferred, but a competitive binding assay may also be employed.

In a still further aspect the invention provides a method for the treatment of a disorder shown to be associated with abnormal activity and/or expression of BNO1, comprising administering a nucleic acid molecule, antibody or compound as described above, to a subject in need of such treatment.

In another aspect the invention provides the use of a nucleic acid molecule, antibody or compound as described above, in the manufacture of a medicament for the treatment of a disorder shown to be associated with abnormal activity and/or expression of BNO1.

In a further aspect a pharmaceutical composition comprising a nucleic acid molecule, antibody or compound as described above, and a pharmaceutically acceptable carrier may be administered.

The pharmaceutical composition may be administered to a subject to treat or prevent a disorder associated with abnormal activity and/or expression of BNO1 including, but not limited to, those provided above. Pharmaceutical compositions in accordance with the present invention are prepared by mixing BNO1 or active fragments or variants thereof having the desired degree of purity, with acceptable carriers, excipients, or stabilizers which are well known. Acceptable carriers, excipients or stabilizers are nontoxic at the dosages and concentrations employed, and include buffers such as phosphate, citrate, and other organic acids; antioxidants including absorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitrol or sorbitol; salt-forming counterions such as sodium; and/or nonionic surfactants such as Tween, Pluronics or polyethylene glycol (PEG).

In further embodiments, any of the genes, peptides, antagonists, antibodies, complementary sequences, or vectors of the invention may be administered in combination with other appropriate therapeutic agents. Selection of the appropriate agents may be made by those skilled in the art, according to conventional pharmaceutical principles. The combination of therapeutic agents may act synergistically to effect the treatment or prevention of the various disorders described above. Using this approach, therapeutic efficacy with lower dosages of each agent may be possible, thus reducing the potential for adverse side effects.

Drug Screening

According to still another aspect of the invention, peptides of the invention, particularly purified BNO1 polypeptides, and cells expressing these are useful for screening of candidate pharmaceutical agents in a variety of techniques for the treatment of disorders associated with BNO1 dysfunction. Such techniques include, but are not limited to, utilising eukaryotic or prokaryotic host cells that are stably transformed with recombinant molecules expressing the BNO1 polypeptide or fragment thereof, preferably in competitive binding assays. Binding assays will measure for the formation of complexes between the BNO1 polypeptide, or fragments thereof, and the agent being tested, or will measure the degree to which an agent being tested will interfere with the formation of a complex between the BNO1 polypeptide, or fragment thereof, and a known ligand, particularly other members of the SCF complex and BNO1 substrates targeted for ubiquitination.

Another technique for drug screening provides high-throughput screening for compounds having suitable binding affinity to the BNO1 polypeptide (see PCT published application WO84/03564). In this stated technique, large numbers of small peptide test compounds can be synthesised on a solid substrate and can be assayed through BNO1 polypeptide binding and washing. Bound BNO1 polypeptide is then detected by methods well known in the art. In a variation of this technique, purified polypeptides can be coated directly onto plates to identify interacting test compounds.

An additional method for drug screening involves the use of host eukaryotic cell lines which carry mutations in the BNO1 gene. The host cell lines are also defective at the polypeptide level. Other cell lines may be used where the gene expression of BNO1 can be switched off. The host cell lines or cells are grown in the presence of various drug compounds and the rate of growth of the host cells is measured to determine if the compound is capable of regulating the growth of defective cells.

BNO1 polypeptide may also be used for screening compounds developed as a result of combinatorial library technology. This provides a way to test a large number of different substances for their ability to modulate activity of a polypeptide. The use of peptide libraries is preferred (see patent WO97/02048) with such libraries and their use known in the art.

A substance identified as a modulator of polypeptide function may be peptide or non-peptide in nature. Non-peptide "small molecules" are often preferred for many in vivo pharmaceutical applications. In addition, a mimic or mimetic of the substance may be designed for pharmaceutical use. The design of mimetics based on a known pharmaceutically active compound ("lead" compound) is a common approach to the development of novel pharmaceuticals. This is often desirable where the original active compound is difficult or expensive to synthesise or where it provides an unsuitable method of administration. In the design of a mimetic, particular parts of the original active compound that are important in determining the target property are identified. These parts or residues constituting the active region of the compound are known as its pharmacophore. Once found, the pharmacophore structure is modelled according to its physical properties using data from a range of sources including x-ray diffraction data and NMR. A template molecule is then selected onto which chemical groups which mimic the pharmacophore can be added. The selection can be made such that the mimetic is easy to synthesise, is likely to be pharmacologically acceptable, does not degrade in vivo and retains the biological activity of the lead compound. Further optimisation or modification can be carried out to select one or more final mimetics useful for in vivo or clinical testing.

It is also possible to isolate a target-specific antibody and then solve its crystal structure. In principle, this approach yields a pharmacophore upon which subsequent drug design can be based as described above. It may be possible to avoid protein crystallography altogether by generating anti-idiotypic antibodies (anti-ids) to a functional, pharmacologically active antibody. As a mirror image of a mirror image, the binding site of the anti-ids would be expected to be an analogue of the original binding site. The anti-id could then be used to isolate peptides from chemically or biologically produced peptide banks.

Any of the therapeutic methods described above may be applied to any subject in need of such therapy, including, for example, mammals such as dogs, cats, cows, horses, rabbits, monkeys, and most preferably, humans.

Diagnostic and Prognostic Applications

Polynucleotide sequences encoding BNO1 may be used for the diagnosis or prognosis of disorders associated with BNO1 dysfunction, or a predisposition to such disorders. Examples of such disorders include, but are not limited to, cancers, immune/inflammatory disorders and neurological disorders. Cancers include adenocarcinoma, leukemia, lymphoma, melanoma, myeloma, sarcoma, teratocarcinoma, and, in particular, cancers of the breast, prostate, liver, ovary, head and neck, heart, brain, pancreas, lung, skeletal muscle, kidney, colon, uterus, testis, adrenal gland, blood, germ cells, placenta, synovial membrane, tonsil, cervix, lymph tissue, skin, bladder, spinal cord, thyroid gland and stomach. Other cancers may include those of the bone, bone marrow, gall bladder, ganglia, gastrointestinal tract, parathyroid, penis, salivary glands, spleen and thymus. Immune/inflammatory disorders include acquired immunodeficiency syndrome (AIDS), Addison's disease, adult respiratory distress syndrome, allergies, ankylosing spondylitis, amyloidosis, anemia, asthma, atherosclerosis. autoimmune hemolytic anemia, autoimmune thyroiditis, autoimmune polyenodocrinopathy-candidiasis-ectodermal dystrophy (APECED), bronchitis, cholecystitis, contact dermatitis, Crohn's disease, cystic fibrosis, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of wound healing (eg scarring), cancer, hemodialysis, and extracorporeal circulation, viral, bacterial, fungal, parasitic, protozoal, and helminthic infections, and trauma. Neurological disorders may include Parkinson's disease and Alzheimer's disease.

Diagnosis or prognosis may be used to determine the severity, type or stage of the disease state in order to initiate an appropriate therapeutic intervention.

In another embodiment of the invention, the polynucleotides that may be used for diagnostic or prognostic purposes include oligonucleotide sequences, genomic DNA and complementary RNA and DNA molecules. The polynucleotides may be used to detect and quantitate gene expression in biopsied tissues in which mutations in BNO1 or abnormal expression of BNO1 may be correlated with disease. Genomic DNA used for the diagnosis or prognosis may be obtained from body cells, such as those present in the blood, tissue biopsy, surgical specimen, or autopsy material. The DNA may be isolated and used directly for detection of a specific sequence or may be amplified by the polymerase chain reaction (PCR) prior to analysis. Similarly, RNA or cDNA may also be used, with or without PCR amplification. To detect a specific nucleic acid sequence, direct nucleotide sequencing, reverse transcriptase PCR (RT-PCR), hybridization using specific oligonucleotides, restriction enzyme digest and mapping, PCR mapping, RNAse protection, and various other methods may be employed. Oligonucleotides specific to particular sequences can be chemically synthesized and labelled radioactively or non-radioactively and hybridised to individual samples immobilized on membranes or other solid-supports or in solution. The presence, absence or excess expression of BNO1 may then be visualized using methods such as autoradiography, fluorometry, or colorimetry.

In a particular aspect, the nucleotide sequences encoding BNO1 may be useful in assays that detect the presence of associated disorders, particularly those mentioned previously. The nucleotide sequences encoding BNO1 may be labelled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding BNO1 in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis or prognosis of a disorder shown to be associated with a mutation in BNO1, the nucleotide sequence of the BNO1 gene can be compared between normal tissue and diseased tissue in order to establish whether the patient expresses a mutant gene.

In order to provide a basis for the diagnosis or prognosis of a disorder shown to be associated with abnormal expression of BNO1, a normal or standard profile for expression is established. This may be accomplished by combining body fluids or cell extracts taken from normal subjects, either animal or human, with a sequence, or a fragment thereof, encoding BNO1, under conditions suitable for hybridization or amplification. Standard hybridization may be quantified by comparing the values obtained from normal subjects with values from an experiment in which a known amount of a substantially purified polynucleotide is used. Another method to identify a normal or standard profile for expression of BNO1 is through quantitative RT-PCR studies. RNA isolated from body cells of a normal individual, particularly RNA isolated from tumour cells, is reverse transcribed and real-time PCR using oligonucleotides specific for the BNO1 gene is conducted to establish a normal level of expression of the gene.

Standard values obtained in both these examples may be compared with values obtained from samples from patients who are symptomatic for a disorder. Deviation from standard values is used to establish the presence of a disorder.

Once the presence of a disorder is established and a treatment protocol is initiated, hybridization assays or quantitative RT-PCR studies may be repeated on a regular basis to determine if the level of expression in the patient begins to approximate that which is observed in the normal subject. The results obtained from successive assays may be used to show the efficacy of treatment over a period ranging from several days to months.

In one aspect, hybridization with PCR probes which are capable of detecting polynucleotide sequences, including genomic sequences, encoding BNO1 or closely related molecules may be used to identify nucleic acid sequences which encode BNO1. The specificity of the probe, whether it is made from a highly specific region, e.g., the 5' regulatory region, or from a less specific region, e.g., a conserved motif, and the stringency of the hybridization or amplification will determine whether the probe identifies only naturally occurring sequences encoding BNO1, allelic variants, or related sequences.

Probes may also be used for the detection of related sequences, and should preferably have at least 50% sequence identity to any of the BNO1 encoding sequences. The hybridization probes of the subject invention may be DNA or RNA and may be derived from the sequence of SEQ ID Numbers: 1 or 3 or from genomic sequences including promoters, enhancers, and introns of the BNO1 gene (SEQ ID Numbers: 5-11).

Means for producing specific hybridization probes for DNAs encoding BNO1 include the cloning of polynucleotide sequences encoding BNO1 or BNO1 derivatives into vectors for the production of mRNA probes. Such vectors are known in the art, and are commercially available. Hybridization probes may be labelled by radionuclides such as $^{32}$P or $^{35}$S, or by enzymatic labels, such as alkaline phosphatase coupled to the probe via avidin/biotin coupling systems, or other methods known in the art.

According to a further aspect of the invention there is provided the use of a polypeptide as described above in the diagnosis or prognosis of a disorder shown to be associated with BNO1, or a predisposition to such disorders.

When a diagnostic or prognostic assay is to be based upon the BNO1 protein, a variety of approaches are possible. For example, diagnosis or prognosis can be achieved by monitoring differences in the electrophoretic mobility of normal and mutant proteins. Such an approach will be particularly useful in identifying mutants in which charge substitutions are present, or in which insertions, deletions or substitutions have resulted in a significant change in the electrophoretic migration of the resultant protein. Alternatively, diagnosis may be based upon differences in the proteolytic cleavage patterns of normal and mutant proteins, differences in molar ratios of the various amino acid residues, or by functional assays demonstrating altered function of the gene products.

In another aspect, antibodies that specifically bind BNO1 may be used for the diagnosis or prognosis of disorders characterized by abnormal expression of BNO1, or in assays to monitor patients being treated with BNO1 or agonists, antagonists, or inhibitors of BNO1. Antibodies useful for diagnostic purposes may be prepared in the same manner as described above for therapeutics. Diagnostic or prognostic assays for BNO1 include methods that utilize the antibody and a label to detect BNO1 in human body fluids or in extracts of cells or tissues. The antibodies may be used with or without modification, and may be labelled by covalent or non-covalent attachment of a reporter molecule.

A variety of protocols for measuring BNO1, including ELISAs, RIAs, and FACS, are known in the art and provide a basis for diagnosing altered or abnormal levels of BNO1 expression. Normal or standard values for BNO1 expression are established by combining body fluids or cell extracts taken from normal mammalian subjects, preferably human, with antibody to BNO1 under conditions suitable for complex formation. The amount of standard complex formation may be quantitated by various methods, preferably by photometric means. Quantities of BNO1 expressed in subject, control, and disease samples from biopsied tissues are compared with the standard values. Deviation between standard and subject values establishes the parameters for diagnosing disease.

Once an individual has been diagnosed with a disorder, effective treatments can be initiated. These may include administering a selective agonist to the mutant BNO1 so as to restore its function to a normal level or introduction of wild-type BNO1, particularly through gene therapy approaches as described above. Typically, a vector capable of expressing the appropriate full-length BNO1 gene or a fragment or derivative thereof may be administered. In an alternative approach to therapy, substantially purified BNO1 polypeptide and a pharmaceutically acceptable carrier may be administered as described above or drugs which can replace the function of, or mimic the action of BNO1 may be administered.

In the treatment of disorders shown to be associated with increased BNO1 expression and/or activity, the affected individual may be treated with a selective antagonist such as an antibody to the relevant protein or an antisense (complement) probe to the corresponding gene as described above, or through the use of drugs which may block the action of BNO1.

Microarray

In further embodiments, complete cDNAs, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose or prognose a disorder, and to develop and monitor the activities of therapeutic agents. Microarrays may be prepared, used, and analyzed using methods known in the art. (For example, see Schena et al., 1996; Heller et al., 1997).

Transformed Hosts

The present invention also provides for the production of genetically modified (knock-out, knock-in and transgenic), non-human animal models transformed with the DNA molecules of the invention. These animals are useful for the study of the BNO1 gene function, to study the mechanisms of disease as related to the BNO1 gene, for the screening of candidate pharmaceutical compounds, for the creation of explanted mammalian cell cultures which express the protein or mutant protein and for the evaluation of potential therapeutic interventions.

The BNO1 gene may have been inactivated by knock-out deletion, and knock-out genetically modified non-human animals are therefore provided.

Animal species which are suitable for use in the animal models of the present invention include, but are not limited to, rats, mice, hamsters, guinea pigs, rabbits, dogs, cats, goats, sheep, pigs, and non-human primates such as monkeys and chimpanzees. For initial studies, genetically modified mice and rats are highly desirable due to their relative ease of maintenance and shorter life spans. For certain studies, transgenic yeast or invertebrates may be suitable and preferred because they allow for rapid screening and provide for much easier handling. For longer term studies, non-human primates may be desired due to their similarity with humans.

To create an animal model for mutated BNO1 several methods can be employed. These include generation of a specific mutation in a homologous animal gene, insertion of a wild type human gene and/or a humanized animal gene by homologous recombination, insertion of a mutant (single or multiple) human gene as genomic or minigene cDNA constructs using wild type or mutant or artificial promoter elements or insertion of artificially modified fragments of the endogenous gene by homologous recombination. The modifications include insertion of mutant stop codons, the deletion of DNA sequences, or the inclusion of recombination elements (lox p sites) recognized by enzymes such as Cre recombinase.

To create a transgenic mouse, which is preferred, a mutant version of BNO1 can be inserted into a mouse germ line using standard techniques of oocyte microinjection or transfection or microinjection into embryonic stem cells. Alternatively, if it is desired to inactivate or replace the endogenous BNO1 gene, homologous recombination using embryonic stem cells may be applied.

For oocyte injection, one or more copies of the mutant or wild type BNO1 gene can be inserted into the pronucleus of a just-fertilized mouse oocyte. This oocyte is then reimplanted into a pseudo-pregnant foster mother. The liveborn mice can then be screened for integrants using analysis of tail DNA for the presence of human BNO1 gene sequences. The transgene can be either a complete genomic sequence injected as a YAC, BAC, PAC or other chromosome DNA fragment, a cDNA with either the natural promoter or a heterologous promoter, or a minigene containing all of the coding region and other elements found to be necessary for optimum expression.

According to still another aspect of the invention there is provided the use of genetically modified non-human animals as described above for the screening of candidate pharmaceutical compounds.

The identification of the nucleotide and amino acid sequence of both isoforms of BNO1 enables the identification of BNO1-specific protein substrates using protein interaction studies such as the yeast two-hybrid analysis as would be understood by those skilled in the art. These protein substrates would be targets for degradation via ubiquitination mediated by the BNO1-containing ubiquitin-E3 ligase. Each isoform of BNO1 may share common protein substrates or may interact with isoform-specific substrates.

In one aspect of the invention there is provided a complex of wild-type BNO1 and a BNO1-specific substrate that is targeted for degradation by ubiquitination.

In a still further aspect of the invention there is provided a complex of BNO1 and proteins of the ubiquitin-E3 ligase complex.

According to a still further aspect of the invention there is provided a complex of wild-type BNO1 and the Skp1 protein.

In a still further aspect of the invention there is provided a nucleic acid encoding a mutant BNO1 polypeptide which cannot form a complex with wild-type proteins with which wild-type BNO1 does form a complex. Typically one of these proteins is Skp1 while others are BNO1-specific protein substrates targeted for degradation by ubiquitination.

According to a still further aspect of the invention there is provided a mutant BNO1 polypeptide which cannot form a complex with wild-type proteins with which wild-type BNO1 does form a complex. Typically one of these proteins is Skp1 while others are BNO1-specific protein substrates targeted for degradation by ubiquitination.

In a still further aspect of the present invention there is provided the use of complexes as described above in screening for candidate pharmaceutical compounds. One may also screen for a drug which replaces the activity of BNO1 in a patient deficient in BNO1.

It will be clearly understood that, although a number of prior art publications are referred to herein, this reference does not constitute an admission that any of these documents forms part of the common general knowledge in the art, in Australia or in any other country. Throughout this specification and the claims, the words "comprise", "comprises" and "comprising" are used in a non-exclusive sense, except where the context requires otherwise.

BRIEF DESCRIPTION OF THE DRAWINGS

FIG. 1. Schematic representation of tumours with interstitial and terminal allelic loss on chromosome arm 16q in the two series of tumour samples. Polymorphic markers are listed according to their order on 16q from centromere to telomere and the markers used for each series are indicated by X. Tumour identification numbers are shown at the top of each column. At the right of the figure, the three smallest regions of loss of heterozygosity are indicated.

FIG. 3. BNO1 F-box sequence alignment compared with the F-box consensus sequence as reported by Kipreos and Pagano, (2000). The single letter amino-acid code is used. Bold capital letters indicate residues found in over 40% of F-box sequences; non-bold capital letters indicate residues found in 20-40% of F-box sequences; bold, lower case letters indicate residues found in 15-19% of the F-boxes; non-bold lower case letters indicate residues found in 10-14% of F-boxes. The top line represents the F-box motif of BNO1 indicating a high degree of homology with the consensus.

MODES FOR PERFORMING THE INVENTION

Example 1

Collection of Breast Cancer Patient Material

Figure 2:
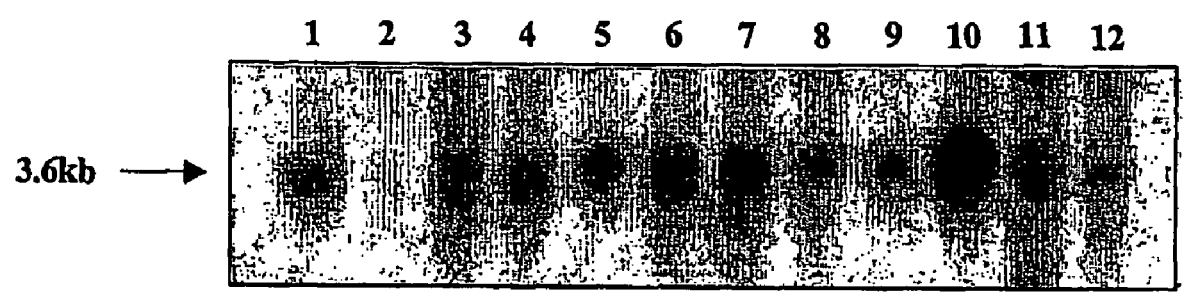
FIG. 2. Northern blot analysis of the BNO1 gene. The size of the BNO1 gene in kilobases is indicated by an arrow on the left of the Northern. The blot contained RNA from the following tissues: 1: Mammary gland; 2: Bone marrow; 3: Testis; 4: Ovary; 5: Uterus; 6: Prostate; 7: Stomach; 8: Bladder; 9: Spinal cord; 10: Brain; 11: Pancreas; 12: Thyroid. A single band of approximately 3.6 Kb was seen in all tissues except bone marrow. Strongest expression of the gene was seen in the brain.

Two series of breast cancer patients were analysed for this study. Histopathological classification of each tumour specimen was carried out by our collaborators according to World Health Organisation criteria (WHO, 1981). Patients were graded histopathologically according to the modified Bloom and Richardson method (Elston and Ellis, 1990) and patient material was obtained upon approval of local Medical Ethics Committees. Tumour tissue DNA and peripheral blood DNA from the same individual was isolated as previously described (Devilee et al., 1991) using standard laboratory protocols.

Series 1 consisted of 189 patients operated on between 1986 and 1993 in three Dutch hospitals, a Dutch University and two peripheral centres. Tumour tissue was snap frozen within a few hours of resection. For DNA isolation, a tissue block was selected only if it contained at least 50% of tumour cells following examination of haematoxilin and eosin stained tissue sections by a pathologist. Tissue blocks that contained fewer than 50% of tumour cells were omitted from further analysis.

Series 2 consisted of 123 patients operated on between 1987 and 1997 at the Flinders Medical Centre in Adelaide, Australia. Of these, 87 were collected as fresh specimens within a few hours of surgical resection, confirmed as malignant tissue by pathological analysis, snap frozen in liquid nitrogen, and stored at −70° C. The remaining 36 tumour tissue samples were obtained from archival paraffin embedded tumour blocks. Prior to DNA isolation, tumour cells were microdissected from tissue sections mounted on glass slides so as to yield at least 80% tumour cells. In some instances, no peripheral blood was available such that pathologically identified paraffin embedded non-malignant lymph node tissue was used instead.

Example 2

LOH Analysis of Chromosome 16q Markers in Breast Cancer Samples

Figure 1:
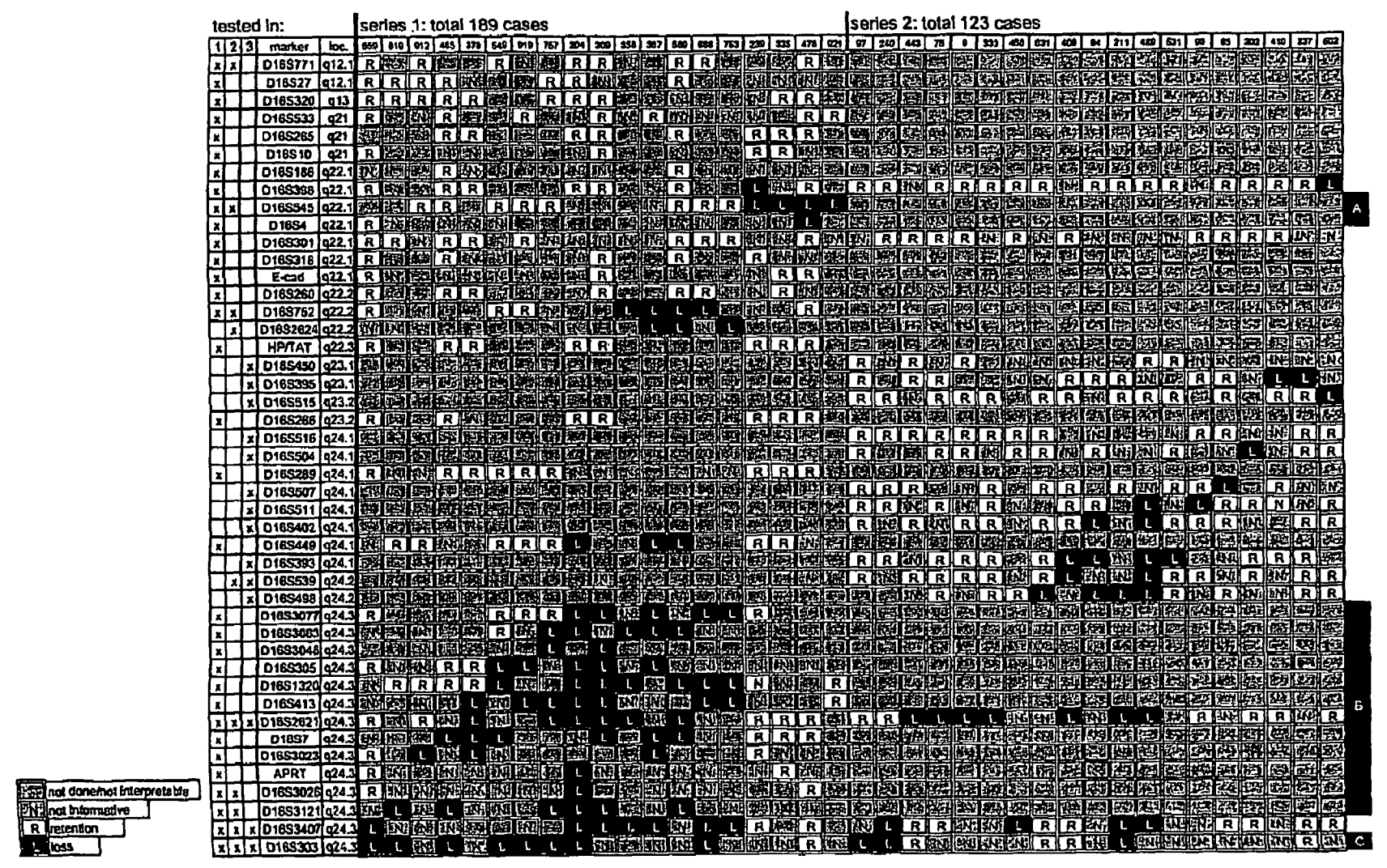

In order to identify the location of genes associated with breast cancer, LOH analysis of tumour samples was conducted. A total of 45 genetic markers mapping to chromosome 16 were used for the LOH analysis of the breast tumour and matched normal DNA samples collected for this study. FIG. 1 indicates for which tumour series they were used and their cytogenetic location. Details regarding all markers can be obtained from the Genome Database (GDB), Hosted by The Hospital for Sick Children, Toronto, Ontario, Canada, and available on the World Wide Web at mirror sites worldwide. The physical order of markers with respect to each other was determined from a combination of information in GDB, by mapping on a chromosome 16 somatic cell hybrid map (Callen et al., 1995) and by genomic sequence information.

Four alternative methods were used for the LOH analysis:

1) For RFLP and VNTR markers, Southern blotting was used to test for allelic imbalance. These markers were used on only a subset of samples. Methods used were as previously described (Devilee et al., 1991).

2) Microsatellite markers were amplified from tumour and normal DNA using the polymerase chain reaction (PCR) incorporating standard methodologies (Weber and May, 1989; Sambrook et al., 1989). A typical reaction consisted of 12 μl and contained 100 ng of template, 5 pmol of both primers, 0.2 mM of each dNTP, 1 μCurie [α-$^{32}$P]dCTP, 1.5 mM MgCl$_2$, 1.2 μl Supertaq buffer and 0.06 units of Supertaq (HT biotechnologies). A Phosphor Imager type 445 SI (Molecular Dynamics, Sunnyvale, Calif.) was used to quantify ambiguous results. In these cases, the Allelic Imbalance Factor (AIF) was determined as the quotient of the peak height ratios from the normal and tumour DNA pair. The threshold for allelic imbalance was defined as a 40% reduction of one allele, agreeing with an AIF of $\geq 1.7$ or $\leq 0.59$. This threshold is in accordance with the selection of tumour tissue blocks containing at least 50% tumour cells with a 10% error-range. The threshold for retention has been previously determined to range from 0.76 to 1.3 (Devilee et al., 1994). This leaves a range of AIFs (0.58-0.75 and 1.31-1.69) for which no definite decision has been made. This "grey area" is indicated by grey boxes in FIG. 1 and tumours with only "grey area" values were discarded completely from the analysis.

3) The third method for determining allelic imbalance was similar to the second method above, however radioactively labelled dCTP was omitted. Instead, PCR of polymorphic microsatellite markers was done with one of the PCR primers labelled fluorescently with FAM, TET or HEX. Analysis of PCR products generated was on an ABI 377 automatic sequencer (PE Biosystems) using 6% polyacrylamide gels containing 8M urea. Peak height values and peak sizes were analysed with the GeneScan programme (PE Biosystems). The same thresholds for allelic imbalance, retention and grey areas were used as for the radioactive analysis.

4) An alternative fluorescent based system was also used. In this instance PCR primers were labelled with fluorescein or hexachlorofluorescein. PCR reaction volumes were 20 μl and included 100 ng of template, 100 ng of each primer, 0.2 mM of each dNTP, 1-2 mM MgCl$_2$, 1× AmpliTaq Gold buffer and 0.8 units AmpliTaq Gold enzyme (Perkin Elmer). Cycling conditions were 10 cycles of 94° C. for 30 seconds, 60° C. for 30 seconds, 72° C. for 1 minute, followed by 25 cycles of 94° C. 30 seconds, 55° C. for 30 seconds, 72° C. for 1 minute, with a final extension of 72° C. for 10 minutes. PCR amplimers were analysed on an ABI 373 automated sequencer (PE Biosystems) using the GeneScan programme (PE Biosystems). The threshold range of AIF for allele retention was defined as 0.61-1.69, allelic loss as $\leq 0.5$ or $\geq 2.0$, or the "grey area" as 051-0.6 or 1.7-1.99.

The first three methods were applied to the first tumour series while the last method was adopted for the second series of tumour samples. For statistical analysis, a comparison of allelic imbalance data for validation of the different detection methods and of the different tumour series was done using the Chi-square test.

The identification of the smallest region of overlap (SRO) involved in LOH is instrumental for narrowing down the location of the gene targeted by LOH. FIG. 1 shows the LOH results for tumour samples, which displayed small regions of loss (ie interstitial and telomeric LOH) and does not include samples that showed complex LOH (alternating loss and retention of markers). When comparing the two sample sets at least three consistent regions emerge with two being at the telomere in band 16q24.3 and one at 16q22.1. The region at 16q22.1 is defined by the markers D16S398 and D16S301 and is based on the interstitial LOH events seen in three tumours from series 1 (239/335/478) and one tumour from series 2 (237). At the telomere (16q24.2-16q24.3), the first region is defined by the markers D16S498 and D16S3407 and is based on four tumours from series 2 (443/75/631/408) while the second region (16q24.3) extends from D16S3407 to the telomere and is based on one tumour from series 1 (559) and three from series 2 (97/240/466). LOH limited to the telomere but involving both of the regions identified at this site could be found in an additional 17 tumour samples.

Other studies have shown that the long arm of chromosome 16 is also a target for LOH in prostate, lung, hepatocellular, ovarian, rhabdomyosarcoma and Wilms' tumours. Detailed analysis of prostate carcinomas has revealed an overlap in the smallest regions of LOH seen in this cancer to that seen with breast cancer which suggests that 16q harbours a gene implicated in many tumour types.

Example 3

Construction of a Physical Map of 16q24.3

To identify novel candidate breast cancer genes mapping to the smallest regions of overlap at 16q24.3, a clone based physical map contig covering this region was needed. At the start of this phase of the project the most commonly used and readily accessible cloned genomic DNA fragments were contained in lambda, cosmid or YAC vectors. During the construction of whole chromosome 16 physical maps, clones from a number of YAC libraries were incorporated into the map (Doggett et al., 1995). These included clones from a flow-sorted chromosome 16-specific YAC library (McCormick et al., 1993), from the CEPH Mark I and MegaYAC libraries and from a half-telomere YAC library (Riethman et al., 1989). Detailed STS and Southern analysis of YAC clones mapping at 16q24.3 established that very few were localised between the CY2/CY3 somatic cell hybrid breakpoint and the long arm telomere. However, those that were located in this region gave inconsistent mapping results and were suspected to be rearranged or deleted. Coupled with the fact that YAC clones make poor sequencing substrates, and the difficulty in isolating the cloned human DNA, a physical map based on cosmid clones was the initial preferred option.

A flow-sorted chromosome 16 specific cosmid library had previously been constructed (Longmire et al., 1993), with individual cosmid clones gridded in high-density arrays onto nylon membranes. These filters collectively contained ~15,000 clones representing an approximately 5.5 fold coverage of chromosome 16. Individual cosmids mapping to the critical regions at 16q24.3 were identified by the hybridisation of these membranes with markers identified by this and previous studies to map to the region. The strategy to align overlapping cosmid clones was based on their STS content and restriction endonuclease digestion pattern. Those clones extending furthest within each initial contig were then used to walk along the chromosome by the hybridisation of the ends of these cosmids back to the high-density cosmid grids. This process continued until all initial contigs were linked and therefore the region defining the location of the breast cancer tumour suppressor genes would be contained within the map. Individual cosmid clones representing a minimum tiling path in the contig were then used for the identification of transcribed sequences by exon trapping, and for genomic sequencing.

Chromosome 16 was sorted from the mouse/human somatic cell hybrid CY18, which contains this chromosome as the only human DNA, and Sau3A partially digested CY18 DNA was ligated into the BamHI cloning site of the cosmid sCOS-1 vector. All grids were hybridised and washed using methods described in Longmire et al. (1993). Briefly, the 10 filters were pre-hybridised in 2 large bottles for at least 2 hours in 20 ml of a solution containing 6×SSC; 10 mM EDTA (pH8.0); 10× Denhardt's; 1% SDS and 100 µg/ml denatured fragmented salmon sperm DNA at 65° C. Overnight hybridisations with [$\alpha$-$^{32}$P]dCTP labelled probes were performed in 20 ml of fresh hybridisation solution at 65° C. Filters were washed sequentially in solutions of 2×SSC; 0.1% SDS (rinse at room temperature), 2×SSC; 0.1% SDS (room temperature for 15 minutes), 0.1×SSC; 0.1% SDS (room temperature for 15 minutes), and 0.1×SSC; 0.1% SDS (twice for 30 minutes at 50° C. if needed). Membranes were exposed at −70° C. for between 1 to 7 days.

Initial markers used for cosmid grid screening were those known to be located below the somatic cell hybrid breakpoints CY2/CY3 and the long arm telomere (Callen et al., 1995). These included three genes, CMAR, DPEP1, and MC1R; the microsatellite marker D16S303; an end fragment from the cosmid 317E5, which contains the BBC1 gene; and four cDNA clones, yc81e09, yh09a04, D16S532E, and ScDNA-C113. The IMAGE consortium cDNA clone, yc81e09, was obtained through screening an arrayed normalised infant brain oligo-dT primed cDNA library (Soares et al., 1994), with the insert from cDNA clone ScDNA-A55. Both the ScDNA-A55 and ScDNA-C113 clones were originally isolated from a hexamer primed heteronuclear cDNA library constructed from the mouse/human somatic cell hybrid CY18 (Whitmore et al., 1994). The IMAGE cDNA clone yh09a04 was identified from direct cDNA selection of the cosmid 37B2 which was previously shown to map between the CY18A(D2) breakpoint and the 16 q telomere. The EST, D16S532E, was also mapped to the same region. Subsequent to these initial screenings, restriction fragments representing the ends of cosmids were used to identify additional overlapping clones.

Contig assembly was based on methods previously described (Whitmore et al., 1998). Later during the physical map construction, genomic libraries cloned into BAC or PAC vectors (Genome Systems or Rosewell Park Cancer Institute) became available. These libraries were screened to aid in chromosome walking or when gaps that could not be bridged by using the cosmid filters were encountered. All BAC and PAC filters were hybridised and washed according to manufacturers recommendations. Initially, membranes were individually pre-hybridised in large glass bottles for at least 2 hours in 20 ml of 6×SSC; 0.5% SDS; 5× Denhardt's; 100 µg/ml denatured salmon sperm DNA at 65° C. Overnight hybridisations with [$\alpha$-$^{32}$P]dCTP labelled probes were performed at 65° C. in 20 ml of a solution containing 6×SSC; 0.5% SDS; 100 µg/ml denatured salmon sperm DNA. Filters were washed sequentially in solutions of 2×SSC; 0.5% SDS (room temperature 5 minutes), 2×SSC; 0.1% SDS (room temperature 15 minutes) and 0.1×SSC; 0.5% SDS (37° C. 1 hour if needed). PAC or BAC clones identified were aligned to the existing contig based on their restriction enzyme pattern or formed unique contigs which were extended by additional filter screens.

As the microsatellite D16S303 was known to be the most telomeric marker in the 16q24.3 region (Callen et al., 1995), fluorescence in situ hybridisation (FISH) to normal metaphase chromosomes using whole cosmids mapping in the vicinity of this marker, was used to define the telomeric limit for the contig. Whole cosmid DNA was nick translated with biotin-14-dATP and hybridised in situ at a final concentration of 20 ng/µl to metaphases from 2 normal males. The FISH method had been modified from that previously described (Callen et al., 1990). Chromosomes were stained before analysis with both propidium iodide (as counter-stain) and DAPI (for chromosome identification). Images of metaphase preparations were captured by a cooled CCD camera using the CytoVision Ultra image collection and enhancement system (Applied Imaging Int. Ltd.). The cosmid 369E1 showed clear fluorescent signals at the telomere of the long arm of chromosome 16. However, this probe also gave clear signal at the telomeres of chromosomal arms 3q, 7p, 9q, 11p, and 17p. Conversely, the cosmid 439G8, which mapped proximal to D16S303, gave fluorescent signals only at 16qter with no consistent signal detected at other telomeres. These results enabled us to establish the microsatellite marker D16S303 as the boundary of the transition from euchromatin to the subtelomeric repeats, providing a telomeric limit to the contig (Whitmore et al., 1998).

A high-density physical map consisting of cosmid, BAC and PAC clones has been established, which extends approximately 3 Mb from the telomere of the long arm of chromosome 16. This contig extends beyond the CY2/CY3 somatic cell hybrid breakpoint and includes the 2 regions of minimal LOH identified at the 16q24.3 region in breast cancer samples. To date, a single gap of unknown size exists in the contig and will be closed by additional contig extension experiments. The depth of coverage has allowed the identification of a minimal tiling path of clones which were subsequently used as templates for gene identification methods such as exon trapping and genomic DNA sequencing.

Example 4

Identification of Candidate Breast Cancer Genes by Analysis of Genomic DNA Sequence Selected minimal overlapping BAC and PAC clones from the physical map contig were sequenced in order to aid in the identification of candidate breast cancer genes. DNA was prepared from selected clones using a large scale DNA isolation kit (Qiagen). Approximately 25-50 ug of DNA was then sheared by nebulisation (10 psi for 45 seconds) and blunt ended using standard methodologies (Sambrook et al., 1989).

Samples were then run on an agarose gel in order to isolate DNA in the 2-4 Kb size range. These fragments were cleaned from the agarose using QIAquick columns (Qiagen), ligated into puc18 and used to transform competent DH10B or DH5a *E. coli* cells. DNA was isolated from transformed clones and was sequenced using vector specific primers on an ABI377 sequencer. Analysis of genomic sequence was performed using PHRED, PHRAP and GAP4 software on a SUN workstation. To assist in the generation of large contigs of genomic sequence, information present in the high-throughput genomic sequence (htgs) database at NCBI was incorporated into the assembly phase of the sequence analysis. The resultant genomic sequence contigs were masked for repeats and analysed using the BLAST algorithm (Altschul et al., 1997) to identify nucleotide and protein homology to sequences in the GenBank non-redundant and EST databases at NCBI. The genomic sequence was also analysed for predicted gene structure using the GENSCAN program.

Homologous IMAGE Consortium cDNA clones were purchased from Genome Systems and were sequenced. These longer stretches of sequence were then compared to known genes by nucleotide and amino acid sequence comparisons using the above procedures. Any sequences that are expressed in the breast are considered to be candidate breast cancer genes. Those genes whose function could implicate them in the tumourigenic process, as predicted from homology searches with known proteins, were treated as the most likely candidates. Evidence that a particular candidate is the responsible gene comes from the identification of defective alleles of the gene in affected individuals or from analysis of the expression levels of a particular candidate gene in breast cancer samples compared with normal control tissues.

Example 5

Identification of the BNO1 Sequence

Genomic Sequence Analysis

Sequences from BAC clones mapping close to the CY2/CY3 breakpoint were assembled and used in BLASTN homology searches of the dbEST database available at the website of the National Center for Biotechnology Information (NCBI). A large number of cDNA clones were identified to be part of the sequence in this region and these could be further characterised into distinct UniGene clusters.

The human IMAGE cDNA clone 46795, corresponding to the UniGene cluster Hs.7970, was sequenced and used in further database homology searches. This identified an overlapping cDNA clone present in the non-redundant database (GenBank accession number AL117444) that extended the sequence of clone 46795 further 5'. As this additional 5' sequence was also present in the genomic sequence located 5' to the 46795 clone sequence, it confirmed that AL117444 most likely belonged to the Hs.7970 transcript. To verify this fact, RT-PCR was done.

Briefly, polyA+ mRNA from normal mammary gland (Clontech) was initially primed with an oligo-dT primer and reverse transcribed using the OmniScript RT kit (Qiagen) according to manufacturers conditions. Control reactions were included for each RNA template which omitted reverse transcriptase from the cDNA synthesis step. This was to determine the presence of any genomic DNA contamination in the RNA samples. The resulting first strand cDNA was PCR amplified using primers AL-1 (specific for AL117444; SEQ ID NO: 20) and 7970-1 (specific for the 3' end of Hs.7970; SEQ ID NO: 21) using the HotStarTaq kit (Qiagen) in a 10 ul reaction volume for 35 cycles. Initially, primers to the control house-keeping gene Esterase D (SEQ ID Numbers: 22 and 23) were used in a separate reaction to confirm the presence of cDNA templates for each reverse transcription reaction. Primer sequences are shown in Table 1. These experiments confirmed that the AL117444 and IMAGE cDNA clone 46795 belonged to the Hs.7970 transcript.

Northern Analysis

To determine the size of the gene corresponding to Hs.7970, a polyA$^+$ Northern blot obtained from Clontech was probed with a portion of the gene which was generated by PCR using primers BNO1-2 (SEQ ID NO: 24) and BNO1-3 (SEQ ID NO: 25). Table 1 lists the primer sequences used. Hybridisations were conducted in 10 ml of ExpressHyb solution (Clontech) overnight at 65° C. Filters were washed according to manufacturers conditions. FIG. 2 shows the results of the hybridisation. A single band of approximately 3.6 kb was detected in the mammary gland, testis, ovary, uterus, prostate, stomach, bladder, spinal cord, brain, pancreas and thyroid. Strongest expression of the gene was seen in the brain. The size of the mRNA corresponding to Hs.7970 as determined by the Northern hybridisation indicated that additional 5' sequence needed to be obtained for the gene.

5' Sequence Identification

To identify additional 5' sequence for the Hs.7970 transcript, cDNA sequences present in dbEST corresponding to the mouse orthologue were utilised. The furthest 5' extending mouse clone (AU080856) included a putative translation start site. Alignment of AU080856 with the human genomic sequence containing Hs.7970 delineated the corresponding human sequence of this transcript up to an identical translation start site. Additional RT-PCR experiments were conducted which confirmed the presence of this 5' sequence in the human Hs.7970 transcript. In addition, further dbEST blast searches identified human cDNA clones containing the 5' end of the gene (eg IMAGE clone 3958783).

The RT-PCR experiments also indicated that Hs.7970 exists as an alternatively spliced isoform. This variant is due to the inclusion of an additional in-frame exon (exon 2.5) located between exons 2 and 3.

In combination, these experiments have established that the Hs.7970 transcript, termed BNO1, exists as two alternatively spliced isoforms. One isoform is 3,574 bp in length (SEQ ID NO: 1) and is composed of 9 exons that span approximately 55 Kb of genomic DNA, while the second form of BNO1, which contains exon 2.5, is 3,661 bp in length (SEQ ID NO: 3). Table 2 shows the genomic structure of the gene indicating the size of introns and exons. Analysis of the BNO1 isoforms indicates that isoform 1 (minus exon 2.5) has an open reading frame of 1,617 nucleotides which codes for a protein of 539 amino acids (SEQ ID NO: 2). Isoform 2 (plus exon 2.5) of BNO1 has an open reading frame of 1,704 bp in length and codes for a protein of 568 amino acids (SEQ ID NO: 4). Partial genomic DNA sequences indicating exon/intron junctions for BNO1 are set forth in SEQ ID Numbers: 5-11.

Example 6

Characteristics of the BNO1 Sequence

Nucleotide Sequence

A large number of human cDNA clones are present in dbEST which represent the BNO1 gene. An observation of the tissues these cDNA clones were derived from indicates that the gene is also expressed in the adrenal gland, blood, colon, germ cells, heart, kidney, liver, lung, muscle, placenta, synovial membrane, tonsil, cervix, lymph tissue and the skin. These tissues are in addition to those shown to express BNO1 from Northern analysis (eg mammary gland, testis, ovary, uterus, prostate, stomach, bladder, spinal cord, brain, pancreas and thyroid) and RT-PCR procedures (eg human mammary gland).

The human BNO1 nucleotide sequence also detects a large number of mouse cDNA clones as previously mentioned. In silico BLAST analysis of mouse genomic DNA sequence in the htgs database at NCBI using the human BNO1 nucleotide sequence was successful in identifying the mouse BNO1 nucleotide (SEQ ID NO: 12) and corresponding amino acid sequence (SEQ ID NO: 13). The amino acid homology between the two genes is as high as 95% (from amino acid 76 in exon 1 to amino acid 369 in exon 8) which suggests that the gene is highly conserved between the two species.

Analysis of the human genomic sequence located 3' to the BNO1 gene identified the presence of a number of additional UniGene clusters (Hs.130367, Hs.227170 and Hs.87068) running in the same orientation. RT-PCR experiments using a Hs.130367 (130367-1; SEQ ID NO: 26) and Hs.87068 (87068-1; SEQ ID NO: 27) specific primer (see Table 1 for primer sequences) indicated that these two UniGene clusters could be linked. Sequencing of the RT-PCR product also identified the presence of the Hs.227170 cluster. Additional RT-PCR experiments using a BNO1 specific primer (BNO1-1; SEQ ID NO: 28) in combination with a Hs.130367 specific primer (130367-2; SEQ ID NO: 29) established that Hs.130367 could also be linked to the BNO1 gene (see Table 1 for primer sequences). Therefore, the three UniGene clusters lying 3' to BNO1 most likely represent variants of this gene that contain additional 3' UTR sequences. The absence of Northern bands corresponding to the size of these BNO1 variants suggests that they are rare forms of the gene. SEQ ID Numbers:14-19 represent the nucleotide sequences of these variants.

Amino Acid Sequence

The amino acid sequence of BNO1 was used for in silico analysis to identify homologous proteins in order to establish the function of the gene product. Analysis of the BNO1 protein against the Prosite and PfScan databases (available on the World Wide Web), showed that both splice isoforms of this protein (SEQ ID Numbers: 2 and 4) contain an F-box domain at the amino terminal end with a highly significant expectation value of 5.6e-10. FIG. 3 shows the sequence of the F-box of BNO1 compared to the consensus F-box sequence.

The F-box is a protein motif of approximately 50 amino acids that defines an expanding family of eukaryotic proteins. F-box containing proteins are the substrate-recognition components of the SCF ubiquitin-ligase complexes. These complexes contain four components: Skp1, Cullin, Rbx/Roc1/Hrt1, and an F-box protein. The F-box motif tethers the F-box protein to other components of the SCF complex by binding the core SCF component, Skp1. This motif is generally found in the amino half of the proteins and is often coupled with other protein domains in the variable carboxy terminus of the protein. The most common carboxy terminal domains include leucine-rich repeats (LRRs) and WD-40 domains. There are currently three subdivisions of the F-box protein family based on the type of carboxy terminal motifs present in the protein sequences. Following the pattern proposed by Cenciarelli et al (1999) and Winston et al (1999), the nomenclature adopted by the Human Genome Organisation denotes F-boxes that contain LRRs as FBXL, those containing WD repeats as FBXW, and those lacking all known protein-interaction domains FBXO. Analysis of the BNO1 sequence failed to identify additional protein motifs present in the gene indicating that BNO1 forms part of the FBXO class of F-box proteins.

The ubiquitin-dependant proteasome degradation pathway is an important mechanism for regulating protein abundance in eukaryotes. A wide variety of proteins have been shown to be regulated by this mechanism and include oncogenes, tumour suppressor genes, transcription factors and other signalling molecules (Hershko and Ciechanover, 1998; Baumeister et al., 1998). These proteins influence a number of important cellular processes such as cell-cycle regulation and apoptosis, modulation of the immune and inflammatory responses, development and differentiation. The diverse range of proteins and processes that are regulated by ubiquitination suggests that pathologies arising from a disruption of the ubiquitination process will also be diverse. For example there is precedence for this in neurodegenerative disorders. Parkin, a protein mutated in inherited forms of Parkinson's disease, is an E3 ubiquitin ligase (Shimura et al., 2000) and in Alzheimer's disease defective ubiquitination of cerebral proteins has been identified (Lopez Salon et al., 2000).

The ubiquitination process begins with the addition of ubiquitin moieties (ubiquitination) to target proteins and follows a multi-step process, the end point of which is the proteolysis of polyubiquitinated substrates by a 26S multi-protein complex (Haas and Siepmann, 1997; Hochstrasser, 1996). Ubiquitination of substrates targeted for degradation requires 3 classes of enzyme: the ubiquitin-activating enzymes (E1), the ubiquitin-conjugating enzymes (E2) and the ubiquitin ligases (E3). The E3 proteins play an integral role in cell cycle progression. SCF complexes (a class of E3 ligases) have been shown to regulate the G1-S phase transition (reviewed in Peters, 1998). A wide variety of SCF targets have been reported that include G1-phase cyclins, cyclin-dependant kinase inhibitors, DNA replication factors, transcription factors that promote cell-cycle progression and other important cellular proteins. The sequences present in the variable carboxy terminal region of the F-box proteins therefore allow recruitment of specific substrates for ubiquitination and subsequent degradation.

Recent studies of the Von Hippel-Lindau (VHL) tumour suppressor protein have shown that it is part of a complex that functions as a ubiquitin-protein ligase E3 (Zaibo et al., 2001). The VHL protein links the ligase complex to target proteins which include HIFα (hypoxia inducible factor) (Ohh et al., 2000; Cockman et al., 2000) and VDU1 (VHL interacting deubiquitinating enzyme 1) (Zaibo et al., 2001). HIFα has been shown to regulate genes involved in angiogenesis, a process critical for the growth of tumours (Wang et al., 1995; Semenza, 2000), while VDU1 has deubiquitinating activity.

The predicted role of BNO1, based on the presence of the F-box domain, indicates that the gene may be involved in a diverse range of cellular processes including cell-cycle regulation. Combined with the fact that BNO1 lies in a region of LOH seen in breast and other tumour types suggests BNO1 is an ideal candidate breast cancer gene.

Example 7

Examination of the Expression Level of BNO1 in Breast Cancer Cell Lines

To investigate a potential role of BNO1 in breast cancer, the level of expression of the gene was compared in breast cancer cell lines with normal tissue controls. Examination of the genomic sequence surrounding BNO1 shows that the 5' end including exon 1 is extremely G-C rich suggesting the presence of a CpG island. While not wishing to be bound by theory, this raises the possibility that epigenetic mechanisms to inactivate BNO1 function may exist. Abnormal methylation at this site may result in a down-regulation of BNO1 transcription of the remaining copy of the gene. Recent studies have shown that this mechanism has been responsible for the inactivation of other tumour suppressor genes such as RB1 (Ohtani-Fujita et al., 1997), VHL (Prowse et al., 1997), MLH1 (Herman et al., 1998) and BRCA1 (Esteller et al., 2000).

To detect the level of expression of BNO1 in cancer samples compared with normal controls, quantitative RT-PCR using BNO1 specific primers was done. This initially involved the isolation of RNA from breast cancer cell lines along with appropriate cell line controls.

Breast/Prostate Cancer Cell Lines and RNA Extraction

Cancer cell lines were purchased from ATCC (USA) and grown in the recommended tissue culture medium. Breast cancer cell lines were chosen for RT-PCR analysis that demonstrated homozygosity for a number of markers mapping to chromosome 16q indicating potential LOH for this chromosomal arm. Cells were harvested from confluent cultures and total RNA was extracted using the RNAeasy kit (Qiagen). Breast cancer cell lines obtained for RNA extraction were BT549, MDA-MB-468, CAMA-1, ZR75-30, MDA-MB-157, ZR75-1, SKBR3, MDA-MB-231, T47D, and MDA-MB-436. The normal breast epithelial cell line MCF12A and the prostate cancer cell line PC3 were also purchased. PolyA$^+$ mRNA was subsequently isolated from all sources using the Oligotex bead system (Qiagen). PolyA$^+$ mRNA from normal mammary gland, prostate, ovary and liver was purchased commercially (Clontech, USA).

Reverse Transcription

PolyA$^+$ mRNA was primed with oligo-dT primers and reverse transcribed using the Omniscript RT kit (Qiagen) according to manufacturers conditions. Control reactions were included for each RNA template which omitted reverse transcriptase from the cDNA synthesis step. This was to determine the presence of any genomic DNA contamination in the RNA samples.

cDNA Normalisation

Internal standard curve amplicons were generated from a mixed pool of normal tissue cDNA using the HotStarTaq™ DNA Polymerase kit (Qiagen). A reaction mix sufficient to generate >1 ug of amplicon cDNA contained 10 ul of 10×PCR buffer (containing 15 MM MgCl$_2$), 2 ul of 10 mM DNTP mix, 0.5 uM of each primer, 0.5 ul of 2.5 units HotStarTaq polymerase (Qiagen), 100 ng of cDNA template and DEPC treated water to 100 ul. Amplification cycling was performed as follows: 94° C. for 10 minutes followed by 35 cycles at 93° C. for 20 seconds, 60° C. for 30 seconds and 70° C. for 30 seconds with a final extension at 72° C. for 4 minutes. Amplicons were purified using the QIAquick gel extraction kit (Qiagen) according to manufacturers conditions and concentrations were measured at A$_{260}$. Purified amplicons were serially diluted 10-fold from 10 ng/ul to 1 fg/ul. These dilutions served as internal standards of known concentration for real-time analysis of BNO1 specific amplicons as described below.

Real-time PCR

All cDNA templates were amplified using the SYBR Green I PCR Master Mix kit (PE Biosystems, USA). PCR reactions were in a volume of 25 ul and included 12.5 ul of SYBR Green I PCR Master mix, 0.5 uM of each primer, 2 ul normalised cDNA template (see below) and 9.5 ul of water. Real-time PCR analysis was performed using the Rotor-Gene™2000 (Corbett Research, AUS) with the following amplification cycling conditions: 94° C. for 10 minutes followed by 45 cycles of 93° C. for 20 sec, 60° C. for 30 sec and 70° C. for 30 sec. Fluorescence data was acquired at 510 nm during the 72° C. extension phase. Melt curve analyses were performed with an initial 99-50° C. cycling followed by fluorescence monitoring during heating at 0.2° C./second to 99° C. Prior to real-time quantification, product size and specificity was confirmed by ethidium bromide staining of 2.5% agarose gels following electrophoresis of completed PCRs. Control and BNO1 specific primers used for all real-time PCR applications are listed in Table 1 and are represented by the SEQ ID Numbers: 30-41.

Real-time PCR Quantification

Quantification analyses were performed on the Rotor-Gene™ DNA sample analysis system (Version 4.2, Build 96). Standard curves were generated by amplifying 10-fold serial dilutions (1 ul of 10 pg/ul down to 1 ul of 1 fg/ul in triplicate) of the internal standard amplicon during real-time PCR of BNO1 amplicons from normal tissues and breast cancer cell lines. Internal standard amplicon concentrations were arbitrarily set to 1.0e+12 copies for 10 pg standards to 1.0e+08 copies for 1 fg standards. $C_T$ (cycle threshold) coefficients of variation for all internal standard dilutions averaged 2% between triplicate samples within the same and different runs. The Rotor-Gene™ quantification software generated a line of best-fit at the parameter $C_T$ and determined unknown normal tissue and breast cancer cell line BNO1 amplicon copy numbers by interpolating the noise-band intercept of BNO1 amplicons against the internal standards with known copy numbers.

Normalization and Relative Expression of Data

Figure 4:
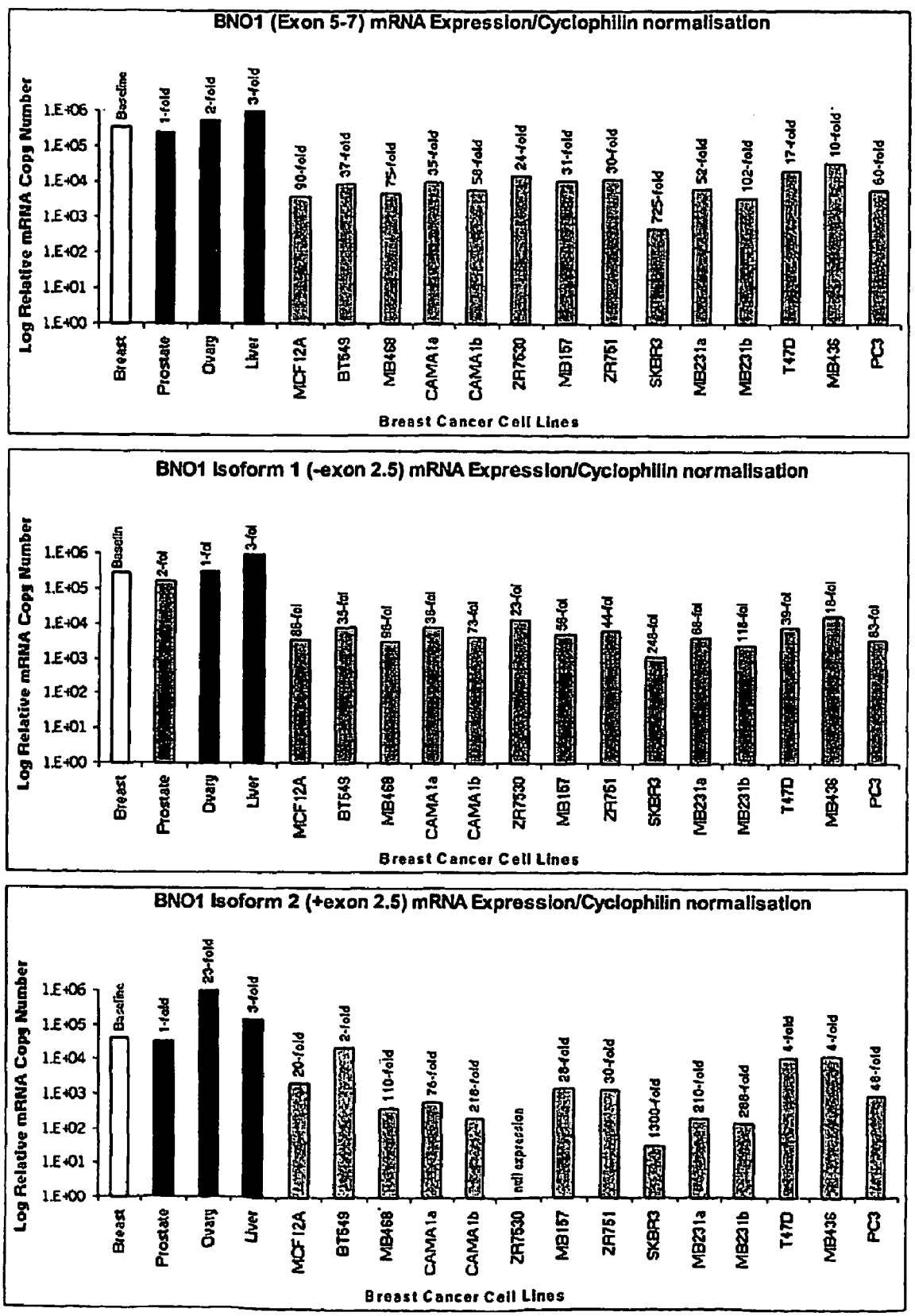
FIG. 4. Quantitative RT-PCR expression analysis of the BNO1 gene in breast cancer cell lines. BNO1 copy numbers in normalized normal mammary gland (breast) cDNA were arbitrarily set to a 'baseline' of 1.0e+06 (empty bar). Breast cancer cell lines and other normal tissue cDNA copy numbers were calculated relative to the 'baseline'. Grey filled bars represent amplicon fold expression down-regulation compared to the baseline reference, while black filled bars represent amplicon fold expression up-regulation from the baseline reference. Note: replicate cell lines (a and b) represent independent cell cultures, total RNA isolation and reverse transcription reactions. Replicates served as another level of control to monitor the variability in gene expression resulting from differences in cell confluency, total RNA integrity and reverse transcription efficiencies.

To account for variation in sample-to-sample starting template concentrations, RiboGreen™ RNA quantitation (Molecular Probes) was used to accurately assay 1 ug of normal tissue and breast cancer cell line RNA for cDNA synthesis. Selected housekeeping gene expression levels were then analyzed in all samples to determine the most accurate endogenous control for data normalization. Housekeeping amplicons included Esterase D (Accession Number M13450), Cyclophilin (Accession Number X52851), APRT (Accession Number M16446) and RNA Polymerase II (Accession Number Z47727). As Cyclophilin displayed the least variable expression profile, calculated BNO1 copy numbers were divided by the respective Cyclophilin amplicon copy number for each breast cancer cell line and normal tissue analyzed. BNO1 copy numbers in normalized normal breast cDNA were arbitrarily set to a 'baseline' of 1.0e+06 copies. Breast cancer cell lines and other normal tissue cDNA copy numbers were calculated relative to the 'baseline'. Data was expressed as log relative mRNA copy number. FIG. 4 shows the results from these experiments.

The degree of variation in mRNA expression levels for Cyclophilin, RNA polymerase II subunit and APRT were relatively uniform between the normal tissues and cancer cell lines. Three-way combinations for normalization between Cyclophilin, RNA polymerase II subunit and APRT demonstrated a mean 7-fold and maximum 50-fold variance in mRNA expression level between samples. The significance of variable mRNA expression levels within a gene of interest may therefore reasonably be evaluated based on these normalization results. A predicted aberrant decrease in gene of interest mRNA copy number of ~100 fold in breast cancer cell lines relative to a 'baseline' normal breast expression level was therefore considered to be significantly abnormal.

FIG. 4 indicates that BNO1 amplicons specific for exon 5-7 and isoform 1 (minus exon 2.5) show a consistent pattern of mRNA expression among normal tissues and breast cancer cell lines. For both amplicons analyzed, the breast cancer cell lines MDA-MB-468, SK-BR3, MDA-MB-231 and the prostate cancer cell line PC3 all display low-level mRNA expression with respect to the 'baseline' normal breast tissue. A significant 725-fold reduction in BNO1 exon 5-7 mRNA expression was detected in SK-BR3 with respect to the normal breast tissue expression (equivalent to an approximately 350,000-480,000 down-regulation in mRNA molecule expression). Similar results were obtained for isoform 1 of BNO1 (minus exon 2.5), with a 248-fold reduction in mRNA expression in SK-BR3 (equivalent to an approximately 300,000-1,000,000 down-regulation in mRNA molecule expression). BNO1 isoform 2 (plus exon 2.5) displayed significantly low mRNA expression in the cell lines MDA-MB-468, CAMA-1, SK-BR3 and MDA-MB-231, with no expression detected in ZR75-30. These results indicate that both isoforms of the BNO1 gene are down-regulated in certain breast cancer cell lines as well as a prostate cancer cell line. The exact mechanism of this down-regulation is not known at this stage but may result from mechanisms such as mutation or promoter methylation. From these expression studies we propose that BNO1 is a protein responsible for the development of breast and prostate cancer. Due to its broad tissue expression pattern, BNO1 may also be implicated in cancers originating from other tissues.

Other methods to detect BNO1 expression levels may be used. These include the generation of polyclonal or monoclonal antibodies, which are able to detect relative amounts of both normal and mutant forms of BNO1 using various immunoassays such as ELISA assays (See Example 11 and 12).

Example 8

Analysis of Tumours and Cell Lines for BNO1 Mutations

The BNO1 gene was screened by SSCP analysis in DNA isolated from tumours from series 1 as well as a subset of series 2 tumours (not shown in FIG. 1) that displayed loss of the whole long arm of chromosome 16. These samples from series 2 were used due to larger amounts of DNA being available. In total 45 primary breast tumours with 16q LOH were examined for mutations.

A number of cell lines were also screened for mutations. These included 22 breast cancer cell lines (BT20, BT474, BT483, BT549, CAMA-1, DU4475, Hs578T, MCF7, MB157, MB231, MB361, MB415, MB436, MB453, MB468, SKBR3, T47D, UACC893, ZR75-1, ZR75-30, MB134 and MB175), 2 prostate cancer cell lines (LNCAP and PC3), 2 gastric carcinoma cell lines (AGS and KATO), 1 liver cancer cell line (HEP2) and 2 normal breast epithelial cell lines (HBL100 and MCF12A). All cell lines were purchased from ATCC, grown according to manufacturers conditions, and DNA isolated from cultured cells using standard protocols (Wyman and White, 1980; Sambrook et al., 1989).

BNO1 exons were amplified by PCR using flanking intronic primers, which were labeled at their 5' ends with HEX. An exception was made for exon 1 and 8, as due to their size had to be split into 2 overlapping amplimers. Table 3 lists the sequences of all primers used for the SSCP analysis, the expected amplimer size and the $MgCl_2$ concentration used in the PCR reaction. Typical PCR reactions were performed in 96-well plates in a volume of 10 ul using 30 ng of template DNA. Cycling conditions were an initial denaturation step at 94° C. for 3 minutes followed by 35 cycles of 94° C. for 30 seconds, 60° C. for $1^{1/2}$ minutes and 72° C. for $1^{1/2}$ minutes. A final extension step of 72° C. for 10 minutes followed. Twenty ul of loading dye comprising 50% (v/v) formamide, 12.5 mM EDTA and 0.02% (w/v) bromophenol blue were added to completed reactions which were subsequently run on 4% polyacrylamide gels and analysed on the GelScan 2000 system (Corbett Research, AUS) according to manufacturers specifications.

Of all 12 amplicons tested, only 2 identified SSCP bandshifts. In exon 2.5, identical bandshifts were seen in 2 tumour samples from series 1 (380 and 355) and the breast cancer cell line MCF7. SSCP analysis of the corresponding normal DNA from sample 380 and 355 identified the same bandshift indicating the change was most likely not causative for the disease. Sequence analysis of this bandshift in all samples showed that a single nucleotide base change (−5T→C) was responsible for this bandshift. This change does not affect the consensus splice acceptor site score for this exon and hence most likely represents a polymorphism. The incidence of this change in the general population has not been examined as yet. In exon 8b, a bandshift was identified in only a single cancer cell line (KATO). Sequencing of this bandshift indicated a C→T change at position +10 of this amplicon which is located in the splice donor site (5' splice site). This base change occurs outside the splice junction consensus sequence and it is envisaged that the mutation has no effect on splicing of this exon.

Example 9

Immunoprecipitation of BNO1 and Skp1

To test if BNO1 contained a functional F-box motif, a co-immunoprecipitation assay was employed. This involved cloning of the full-length Myc-tagged open reading frame of BNO1 into the SalI/ClaI sites of the retroviral expression vector LNCX2 (Clontech) using standard techniques (Sambrook et al., 1989). Following this, $10^7$ 293T cells were transfected with 10 ug of the BNO1-LNCX2 construct or separately with LCNX2 vector alone as a control using Lipofectamine 2000 (Invitrogen) according to manufacturers instructions. Cells were harvested 24 hours post-transfection and lysed in 2 ml of lysis buffer (50 mM Tris-HCL [pH 7.5], 150 mM NaCl, 0.5% Nonidet P-40 supplemented with 1 mM PMSF and 5 μg/ml leupeptin, antipain and aprotenin). Following this, 0.5 ml of the cell lysate was incubated with 2 ug of anti-Myc monoclonal antibody (Roche) or anti-p19$^{SkP1}$ rabbit polyclonal antibody (Neo Markers, Fremont, Calif.) for 1 hour and protein A-Sepharose for 1 hour at 4° C. Immune complexes were washed three times with 1 ml of lysis buffer followed by separation on 10% SDS-PAGE and immunoblotting according to standard techniques (Sambrook et al., 1989).

Results from these experiments indicated that BNO1 specifically co-precipitated with endogenous Skp1, confirming both an association between these two proteins and the presence of a functional F-box within BNO1. This interaction indicates that BNO1 belongs to a novel E3-ubiquitin ligase complex that may be critical for the controlled degradation of BNO1 specific substrates.

Example 10

Analysis of the BNO1 Gene

The following methods are used to determine the structure and function of BNO1.

Biological Studies

Mammalian expression vectors containing BNO1 cDNA (representing both isoforms of BNO1) can be transfected into breast, prostate or other carcinoma cell lines that have lesions in the gene. Phenotypic reversion in cultures (eg cell morphology, growth of transformants in soft-agar, growth rate) and in animals (eg tumourigenicity in nude mice) is examined. These studies can utilise wild-type or mutant forms of BNO1. Deletion and missense mutants of BNO1 can be constructed by in vitro mutagenesis.

Molecular Biological Studies

The ability of both isoforms of the BNO1 protein to bind known and unknown proteins can be examined. Procedures such as the yeast two-hybrid system are used to discover and identify any functional partners, particularly BNO1 specific substrates or isoform-specific substrates that are targeted for degradation by ubiquitination. The principle behind the yeast two-hybrid procedure is that many eukaryotic transcriptional activators, including those in yeast, consist of two discrete modular domains. The first is a DNA-binding domain that binds to a specific promoter sequence and the second is an activation domain that directs the RNA polymerase II complex to transcribe the gene downstream of the DNA binding site. Both domains are required for transcriptional activation as neither domain can activate transcription on its own. In the yeast two-hybrid procedure, the gene of interest or parts thereof (BAIT), is cloned in such a way that it is expressed as a fusion to a peptide that has a DNA binding domain. A second gene, or number of genes, such as those from a cDNA library (TARGET), is cloned so that it is expressed as a fusion to an activation domain. Interaction of the protein of interest with its binding partner brings the DNA-binding peptide together with the activation domain and initiates transcription of the reporter genes. The first reporter gene will select for yeast cells that contain interacting proteins (this reporter is usually a nutritional gene required for growth on selective media). The second reporter is used for confirmation and while being expressed in response to interacting proteins it is usually not required for growth.

The nature of the BNO1 interacting genes and proteins can also be studied such that these partners can also be targets for drug discovery. Of particular interest are those BNO1-interacting proteins that are targeted for ubiquitination and subsequent degradation by the BNO1-containing ubiquitin-E3 ligase.

Structural Studies

BNO1 recombinant proteins can be produced in bacterial, yeast, insect and/or mammalian cells and used in crystallographical and NMR studies. Together with molecular modeling of the protein, structure-driven drug design can be facilitated.

Example 11

Generation of Polyclonal Antibodies Against BNO1

The knowledge of the nucleotide and amino acid sequence of BNO1 allows for the production of antibodies, which selectively bind to BNO1 protein or fragments thereof. Following the identification of mutations in the gene, antibodies can also be made to selectively bind and distinguish mutant from normal protein. Antibodies specific for mutagenised epitopes are especially useful in cell culture assays to screen for malignant cells at different stages of malignant development. These antibodies may also be used to screen malignant cells, which have been treated with pharmaceutical agents to evaluate the therapeutic potential of the agent.

To prepare polyclonal antibodies, short peptides can be designed homologous to the BNO1 amino acid sequence. Such peptides are typically 10 to 15 amino acids in length. These peptides should be designed in regions of least homology to the mouse orthologue to avoid cross species interactions in further down-stream experiments such as monoclonal antibody production. Synthetic peptides can then be conjugated to biotin (Sulfo-NHS-LC Biotin) using standard protocols supplied with commercially available kits such as the PIERCE™ kit (PIERCE). Biotinylated peptides are subsequently complexed with avidin in solution and for each peptide complex, 2 rabbits are immunized with 4 doses of antigen (200 µg per dose) in intervals of three weeks between doses. The initial dose is mixed with Freund's Complete adjuvant while subsequent doses are combined with Freund's Immuno-adjuvant. After completion of the immunization, rabbits are test bled and reactivity of sera assayed by dot blot with serial dilutions of the original peptides. If rabbits show significant reactivity compared with pre-immune sera, they are then sacrificed and the blood collected such that immune sera can separated for further experiments.

Example 12

Generation of Monoclonal Antibodies Specific for BNO1

Monoclonal antibodies can be prepared for BNO1 in the following manner. Immunogen comprising intact BNO1 protein or BNO1 peptides (wild type or mutant) is injected in Freund's adjuvant into mice with each mouse receiving four injections of 10 to 100 ug of immunogen. After the fourth injection blood samples taken from the mice are examined for the presence of antibody to the immunogen. Immune mice are sacrificed, their spleens removed and single cell suspensions are prepared (Harlow and Lane, 1988). The spleen cells serve as a source of lymphocytes, which are then fused with a permanently growing myeloma partner cell (Kohler and Milstein, 1975). Cells are plated at a density of $2 \times 10^5$ cells/well in 96 well plates and individual wells are examined for growth. These wells are then tested for the presence of BNO1 specific antibodies by ELISA or RIA using wild type or mutant BNO1 target protein. Cells in positive wells are expanded and subcloned to establish and confirm monoclonality. Clones with the desired specificity are expanded and grown as ascites in mice followed by purification using affinity chromatography using Protein A Sepharose, ion-exchange chromatography or variations and combinations of these techniques.

Disclosed in one embodiment is an isolated gene comprising the nucleotide sequence set forth in SEQ ID NO: 1 from base 4 to base 1,621 or set forth in SEQ ID NO: 3 from base 4 to base 1,708 and BNO1 control elements. The BNO1 control elements can be those which mediate expression in breast, prostate, liver and ovarian tissue.

In another embodiment, provided is a cell transformed with an expression vector as disclosed herein. In the cell, BNO1 can be expressed in a mutant form. In the cell, BNO1 expression can switched off. The cell can be an eukaryotic cell. In one embodiment a method of preparing a polypeptide is provided, wherein the method comprising the steps of: culturing such cells under conditions effective for production of the polypeptide; and harvesting the polypeptide. Also disclosed is a method of screening for drug candidates, comprising the steps of: providing a cell as described above; adding a drug candidate to the cell; and determining the effect of the drug candidate on the expression of BNO1 by the cell. The use of a cell as described above in the screening of drug candidates is also disclosed, as is the use of a nucleic acid as described herein in screening for drug candidates.

Also disclosed is an isolated polypeptide comprising the amino acid sequence set forth in SEQ ID Numbers: 2 or 4. In another embodiment, disclosed is an isolated polypeptide, comprising the amino acid sequence set forth in SEQ ID Numbers: 2 or 4, or a fragment thereof, capable of forming part of a ubiquitin-ligase complex involved in protein degradation through ubiquitination. In another embodiment, disclosed is an isolated polypeptide capable of forming part of a ubiquitin-ligase complex involved in protein degradation through ubiquitination that has at least 70% identity with the amino acid sequence set forth in SEQ ID Numbers: 2 or 4; optionally, with at least 85% sequence identity, and also optionally, with at least 95% sequence identity. The sequence identity can determined using the BLASTP algorithm and the BLOSSUM62 default matrix. An isolated polypeptide consisting of the amino acid sequence set forth in SEQ ID Numbers: 2 or 4 is also disclosed, as is an isolated polypeptide as described herein which is inactivated as a result of mutation or polymorphism.

An antibody that binds a polypeptide as disclosed herein is also provided. The antibody can be selected from the group consisting of a monoclonal antibody, a humanised antibody, a chimaeric antibody or an antibody fragment including a Fab fragment, F(ab')$_2$ fragment, Fv fragment, single chain antibodies and single domain antibodies.

In another embodiment disclosed is a method of treatment of a disorder associated with decreased expression or activity of BNO1, comprising administering an isolated nucleic acid molecule as defined herein to a subject in need of such treatment. An expression vector comprising the isolated nucleic acid molecule operably linked to suitable control elements can be administered. The use of a nucleic acid molecule as disclosed herein in the manufacture of a medicament for the treatment of disorder associated with decreased expression or activity of BNO1 is also provided. Optionally, the nucleic acid molecule is a part of an expression vector which also includes suitable control elements.

Also disclosed is a method for the treatment of a disorder associated with decreased expression or activity of BNO1, comprising administering a compound which increases expression or activity of BNO1 to a subject in need of such treatment.

Also disclosed is a method for the treatment of a disorder associated with increased expression or activity of BNO1, comprising administering an antagonist of BNO1 to a subject in need of such treatment. The antagonist of BNO1 can be an antibody as defined herein. Also disclosed is the use of an antagonist of BNO1 in the manufacture of a medicament for the treatment of a disorder associated with increased expression or activity of BNO1. The antagonist of BNO1 can be an antibody as defined herein.

Also disclosed is a method for the treatment of a disorder associated with increased expression or activity of BNO1, comprising administering a nucleic acid molecule which is the complement of any one of the nucleic acid molecules as defined herein, the transcription product of which is a RNA molecule that hybridizes with the mRNA encoded by BNO1. Also disclosed is the use of an isolated nucleic acid molecule which is the complement of a nucleic acid molecule as defined herein, the transcription product of which is a mRNA that hybridizes with the mRNA encoded by BNO1, in the manufacture of a medicament for the treatment of a disorder associated with increased activity or expression of BNO1.

Also disclosed is a method for the treatment of a disorder associated with increased expression or activity of BNO1, comprising administering a compound which decreases expression or activity of BNO1 to a subject in need of such treatment. The use of a compound which modulates the expression of BNO1 in the preparation of a medicament for the treatment of disorders associated with abnormal expression or activity of BNO1 is also disclosed.

Also disclosed are a pharmaceutical composition comprising a nucleic acid molecule as defined herein, and a pharmaceutical acceptable carrier; a pharmaceutical composition comprising an antibody as defined herein, and a pharmaceutical acceptable carrier; and a pharmaceutical composition comprising a compound that modulates the expression of BNO1, and a pharmaceutical acceptable carrier.

Also disclosed is a method for screening for a compound capable of modulating the activity of BNO1 comprising combining a peptide as defined herein and a candidate compound, and determining the binding of the candidate compound to the peptide. The use of a peptide as defined herein in screening for candidate pharmaceutical agents is also disclosed.

Also disclosed is a method for the diagnosis of a disorder associated with mutations in BNO1, or a predisposition to such disorders in a patient, comprising the steps of: obtaining a sample which includes BNO1 or a nucleic acid which codes for BNO1 from the patient; comparing BNO1 or a nucleic acid which codes for TSG18 from the sample with wild-type BNO1 or a nucleic acid which codes for it in order to establish whether the person expresses a mutant BNO1. Optionally, the nucleotide sequence of DNA from the patient is compared to the sequence of DNA encoding wild-type BNO1.

Also disclosed is a method for the diagnosis of a disorder associated with abnormal expression or activity of BNO1, or a predisposition to such disorders, comprising the steps of: establishing a profile for normal expression of BNO1 in unaffected subjects; measuring the level of expression of BNO1 in a person suspected of abnormal expression or activity of BNO1; and comparing the measured level of expression with the profile for normal expression. Reverse transcriptase PCR can be employed to measure levels of expression. A hybridisation assay using a probe derived from BNO1, or a fragment thereof, can be employed to measure levels of expression. The probe can have at least 50% sequence identity to a nucleotide sequence encoding BNO1, or a fragment thereof.

Also disclosed is a method for the diagnosis of a disorder associated with BNO1, or a predisposition to such disorders, comprising the steps of: establishing a physical property of wild-type BNO1; obtaining BNO1 from a person suspected of an abnormality of BNO1; and measuring the property for the BNO1 expressed by the person and comparing it to the established property for wild-type BNO1 in order to establish whether the person expresses a mutant BNO1. The property can be the electrophoretic mobility. The property can be the proteolytic cleavage pattern.

Also disclosed is a genetically modified non-human animal transformed with an isolated nucleic acid molecule as defined herein. The genetically modified non-human animal can be selected from the group consisting of rats, mice, hamsters, guinea pigs, rabbits, dogs, cats, goats, sheep, pigs and non-human primates such as monkeys and chimpanzees. In one embodiment, the genetically modified non-human animal is a mouse. In one embodiment, the genetically modified non-human animal is an animal in which BNO1 gene function has been knocked out. In this embodiment, the genetically modified non-human animal can be selected from the group consisting of rats, mice, hamsters, guinea pigs, rabbits, dogs, cats, goats, sheep, pigs and non-human primates such as monkeys and chimpanzees. In one embodiment the genetically modified non-human animal is a mouse. The use of a genetically modified non-human animal as defined herein in screening for candidate pharmaceutical compounds is also disclosed.

Also disclosed is a microarray comprising a nucleic acid encoding either isoform of BNO1 or, a fragment thereof, or nucleic acids encoding both isoforms of BNO1, or fragments thereof. The use of either isoform of BNO1 in order to identify BNO1-specific protein substrates that are targeted for degradation by ubiquitination is also disclosed.

Also disclosed is a complex of BNO1 and a BNO1-specific protein substrate, as is the use of a complex of BNO1 and a BNO1-specific protein substrate in the screening for candidate pharmaceutical compounds.

Also disclosed is a complex of BNO1 and proteins of the ubiquitin-E3 ligase complex, as is the use of a complex of BNO1 and proteins of the ubiquitin-E3 ligase complex in screening for candidate pharmaceutical compounds.

Also disclosed is a mutant BNO1 polypeptide which cannot form a complex with its specific protein substrate, as is the use of a mutant BNO1 polypeptide as defined herein in screening for candidate pharmaceutical compounds. A mutant BNO1 polypeptide which cannot form a complex with the ubiquitin-E3 ligase complex is disclosed, as is the use of a mutant BNO1 polypeptide as defined herein in screening for candidate pharmaceutical compounds.

Also disclosed is an isolated nucleic acid molecule comprising the partial genomic DNA sequences set forth in any one of SEQ ID Numbers: 5-11. Also disclosed is an isolated nucleic acid molecule comprising the nucleotide sequence set forth in SEQ ID NO: 12. Also disclosed is an isolated polypeptide comprising the amino acid sequence set forth in SEQ ID NO: 13. Also disclosed is an isolated nucleic acid comprising the nucleotide sequence set forth in any one of SEQ ID Numbers: 14-19.

INDUSTRIAL APPLICABILITY

The BNO1 gene is implicated in cancer and based on its role in the ubiquitination process, BNO1 may also be implicated in cellular mechanisms which are regulated by this process. The novel DNA molecules of the present invention are therefore useful in methods for the early detection of disease susceptible individuals as well as in therapeutic procedures associated with these disease states.

TABLE 1

Primers Used for Analysis of BNO1

| Primer Name | Primer Sequence (5' → 3') | |
|---|---|---|
| AL-1 | GTA AAG AAG GAT GAG TTC TCC | (SEQ ID NO: 20) |
| 7970-1 | AGC TGA GCA TCA CAA TCT CC | (SEQ ID NO: 21) |
| ESTD-F | GGA GCT TCC CCA ACT CAT AAA TGC C | (SEQ ID NO: 22) |
| ESTD-R | GCA TGA TGT CTG ATG TGG TCA GTA A | (SEQ ID NO: 23) |
| BNO1-2 | TGC GAA GCT GCT TCA CCG AT | (SEQ ID NO: 24) |
| BNO1-3 | GGC CGT ACA TGC ACT CCA CTG | (SEQ ID NO: 25) |
| 130367-1 | GAG AAC CTG CAG TTG TGC TG | (SEQ ID NO: 26) |
| 87068-1 | ATG GTG CTG CTT GTA GCA AG | (SEQ ID NO: 27) |
| 130367-2 | ACA CTC AGC AGT GGA CAC TTG | (SEQ ID NO: 28) |
| Cyclophilin F[1] | GGC AAA TGC TGG ACC CAA CAC AAA | (SEQ ID NO: 30) |
| Cyclophilin R[1] | CTA GGC ATG GGA GGG AAC AAG GAA | (SEQ ID NO: 31) |
| APRT-F[1] | GAC TGG GCT GCG TGC TCA TCC | (SEQ ID NO: 32) |
| APRT-R[1] | AGG CCC TGT GGT CAC TCA TAC TGC | (SEQ ID NO: 33) |
| RNA Polymerase II-F[1] | AGG GGC TAA CAA TGG ACA CC | (SEQ ID NO: 34) |
| RNA Polymerase II-R[1] | CCG AAG ATA GGG GGA AC TAC T | (SEQ ID NO: 35) |
| BNO1 (Exon 5-7)-F[1] | CCG GCG GGA GGC AGG AGG AGT | (SEQ ID NO: 36) |
| BNO1 (Exon 5-7)-R[1] | GCG GCG GTA GGT CAG GCA GTT GTC | (SEQ ID NO: 37) |
| BNO1 (Isoform 1)-F[1] | TGC GAA GCT GCT TCA CCG AT | (SEQ ID NO: 38) |

TABLE 1-continued

Primers Used for Analysis of BN01

| Primer Name | Primer Sequence (5' → 3') | |
|---|---|---|
| BNO1 (Isoform 1)-R[1] | GGC CGT ACA TGC ACT CCA CTG | (SEQ ID NO: 39) |
| BNO1 (Isoform 2)-F[1] | GTG AAG TCG GGA CGT TTT GTG A | (SEQ ID NO: 40) |
| BNO1 (Isoform 2)-R[1] | CCG TGG TGG GGC CCT TTG TGG | (SEQ ID NO: 41) |

Note:
[1]These primers were labeled at their 5' ends with HEX. Isoform 1 of BNO1 lacks exon 2.5 (SEQ ID NO:1). Isoform 2 of BNO1 contains exon 2.5 (SEQ ID NO:3)

TABLE 2

Splice Sites of the BNO1 Gene

| Exon | Size (bp) | 3' Splice site (intron/exon) | Consensus strength (%) | 5' Splice site (exon/intron) | Consensus strength (%) | Intron size (bp) |
|---|---|---|---|---|---|---|
| 1 | 343 | 5'UTR | | TGCCGTGAGG/gtgagcgcgc (SEQ ID NO: 51) | 83.03 | 23042 |
| 2 | 72 | cttgttacag/AGTATGGTGT (SEQ ID NO: 42) | 94.28 | TATGCGAAGC/gtgagtgaat (SEQ ID NO: 52) | 75.36 | 1797 |
| 2.5 | 87 | gtctgttcag/GTATAAACCC (SEQ ID NO: 43) | 90.0 | TACACCTGCC/gtatgtacct (SEQ ID NO: 53) | 66.97 | 11160 |
| 3 | 77 | cctcctgtag/TGCTTCACCG (SEQ ID NO: 44) | 78.70 | GAACGTGGTG/gtaagtcccg (SEQ ID NO: 54) | 92.15 | 3408 |
| 4 | 168 | cctcctgtag/GTGGACGGCC (SEQ ID NO: 45) | 84.95 | CCACATCCAG/gtgtgtgcag (SEQ ID NO: 55) | 85.40 | 646 |
| 5 | 75 | aacactgaag/ATTGTGAAGA (SEQ ID NO: 46) | 63.39 | GAGGCAGGAG/gtgagcccac (SEQ ID NO: 56) | 90.87 | 6612 |
| 6 | 110 | cttttggaag/GAGTTTCGGA (SEQ ID NO: 47) | 85.65 | GTCAGTACGA/gtgagtgcgg (SEQ ID NO: 57) | 76.46 | 697 |
| 7 | 154 | ctccccacag/CAACTGCCTG (SEQ ID NO: 48) | 85.32 | CAAGATCACG/gtgagtggcg (SEQ ID NO: 58) | 88.50 | 1017 |
| 8 | 401 | tgctccacag/GGCGACCCCA (SEQ ID NO: 49) | 89.22 | GCAGGATGTG/gtaaggatg (SEQ ID NO: 59) | 87.59 | 2375 |
| 9 | 2174 | ttctgctcag/TTTTTATGGC (SEQ ID NO: 50) | 90.62 | 3'UTR | | |

TABLE 3

Primers used for the SSCP analysis of BNO1

| Exon | Primer 1 (5' → 3') | Primer 2 (5' → 3') | [MgCl$_s$] | Product Size (bp) |
|---|---|---|---|---|
| 1a | GCGCTGGAGCGTGCGCACA (SEQ ID NO: 60) | AGCTCGGGCGGCAGCTCCA (SEQ ID NO: 72) | 2.0 mM | 269 |
| 1b | GGTCGGGGGCGGCTTGTG (SEQ ID NO: 61) | GCCTCCACCTGGCAGGGA (SEQ ID NO: 73) | 2.0 mM | 252 |
| 2 | CTGTCGCGTTATGAGTTGTTG (SEQ ID NO: 62) | GTACAAAGTTAATCATGGATGGT (SEQ ID NO: 74) | 2.0 mM | 168 |
| 2.5 | AGGCATTGGGTCGTATTCAC (SEQ ID NO: 63) | AGAAGCCAAAGCTCGCAGGA (SEQ ID NO: 75) | 1.5 mM | 198 |
| 3 | GGCACGCTGGGTCTAACAC (SEQ ID NO: 64) | CCTGCCCGTGCACAGACCT (SEQ ID NO: 76) | 1.5 mM | 167 |

TABLE 3-continued

Primers used for the SSCP analysis of BN01

| Exon | Primer 1 (5' → 3') | Primer 2 (5' → 3') | [MgCl$_s$] | Product Size (bp) |
|---|---|---|---|---|
| 4 | CTCATGGACCTTTGCCCATCT (SEQ ID NO: 65) | GTCTGCAGCTGAGAATAGCAC (SEQ ID NO: 77) | 1.0 mM | 290 |
| 5 | GTGATGGACTCTGTTCCTCAC (SEQ ID NO: 66) | AGGTCCGCACCATATGAACAC (SEQ ID NO: 78) | 2.0 mM | 170 |
| 6 | CACAGCCTCCTGTCATATGGA (SEQ ID NO: 67) | ACCCCAGCACCGAGCAGGA (SEQ ID NO: 79) | 1.5 mM | 187 |
| 7 | GGCGTTCTCAGTCCTGCCT (SEQ ID NO: 68) | CCCTGACTCCACAGCCCAC (SEQ ID NO: 80) | 1.5 mM | 284 |
| 8a | CTGGCCTGAGCCCTGCTGA (SEQ ID NO: 69) | ACCCTCTCGCGCACCTCCA (SEQ ID NO: 81) | 1.0 mM | 171 |
| 8b | CAATGAGCTCTCCCGCATC (SEQ ID NO: 70) | CCATGCTGTCCCACCTTCA (SEQ ID NO: 82) | 1.5 mM | 354 |
| 9 | AGAATGCTGTACGTGGCGTG (SEQ ID NO: 71) | AGGAGGTGAGGGACTGAATG (SEQ ID NO: 83) | 1.0 mM | 292 |

Note:
All primes were labelled at their 5' ends with HEX.

REFERENCES

References cited herein are listed on the following pages, and are incorporated herein by this reference.

Altschul, S F. et al. (1997). *Nucleic Acids Res.* 25: 3389-3402.
Brenner, A J. and Aldaz C M. (1995). *Cancer Res.* 55: 2892-2895.
Baumeister, W. et al. (1998). *Cell* 92: 367-380.
Callen, D F. et al. (1990). *Ann. Genet.* 33: 219-221.
Callen, D F. et al. (1995). *Genomics* 29: 503-511.
Cenciarelli, C. et al. (1999). *Curr. Biol.* 9: 1177-1179.
Chen, T. et al. (1996). *Cancer Res.* 56: 5605-5609.
Cleton-Jansen, A-M. et al. (1995). *Br. J. Cancer* 72: 1241-1244.
Cockman, M E. et al. (2000). *J. Biol. Chem.* 275: 25733-25741.
Cole, S P. et al. (1984). *Mol. Cell Biol.* 62: 109-120.
Cote, R J. et al. (1983). *Proc. Natl. Acad. Sci. USA* 80: 2026-2030.
Culver, K. (1996). Gene Therapy: *A Primer for Physicians*. Second Edition. (Mary Ann Liebert).
Devilee, P. et al. (1991). *Oncogene* 6: 1705-1711.
Devilee, P. and Cornelisse, C J. (1994). *Biochimica et Biophysica Acta* 1198: 113-130.
Doggett, N A. et al. (1995). *Nature* 377 Suppl: 335-365.
Elston, C W. and Ellis, I O. (1990). *Histopathology* 16: 109-118.
Esteller, M. et al. (2000). *J. Natl. Cancer Inst.* 92: 564-569.
Fearon, E R. and Vogelstein, B. (1990). *Cell* 61: 759-767.
Friedman, T. (1991). In *Therapy for Genetic Diseases*. T Friedman (Ed). Oxford University Press. pp 105-121.
Futreal, P A. et al. (1994). *Science* 266: 120-122.
Goldman, C K. et al. (1997). *Nature Biotechnology* 15: 462-466.
Haas, A L, and Siepmann, T J. (1997). *FASEB* 11: 1257-1268.
Hall, J M. et al. (1990). *Science* 250: 1684-1689.
Harlow, E. and Lane, D. (1988). *Antibodies: A Laboratory Manual* (Cold Spring Harbor Laboratory, Cold Spring Harbor, NY).
Heller, R A. et al. (1997). *Proc. Natl. Acad. Sci. USA* 94: 2150-2155.
Herman, J G. et al. (1998). *Proc. Natl. Acad. Sci. USA* 95: 6870-6875.
Hershko, A. and Ciechanover, A. (1998). *Annu. Rev. Biochem.* 67: 425-479.
Hochstrasser, M. (1996). *Ann. Rev. Genet.* 30 : 405-439.
Huse, W D. et al. (1989). *Science* 246: 1275-1281.
Kipreos, E T. and Pagano, M. (2000). *Genome Biology* 1: reviews 3002.1-3002.7.
Kohler, G. and Milstein, C. (1975). *Nature* 256: 495-497.
Kozbor, D. et al. (1985). *J. Immunol. Methods* 81:31-42.
Longmire, J L. et al. (1993). *GATA* 10: 69-76.
Lopez Salon, M. et al. (2000). i J. Neurosci. Res. 62: 302-310.
McCormick, M K. et al. (1993). *Proc. Natl. Acad. Sci. USA* 90: 1063-1067.
Miki, Y. et al. (1994). *Science* 266: 66-71.
Miki, Y. et al. (1996). *Nature Genet.* 13: 245-247.
Ohh, M. et al. (2000). *Nat. Cell Biol.* 2: 423-427.
Ohtani-Fujita, N. et al. (1997). *Cancer Genet. Cytogenet.* 98:43-49.
Orlandi, R. et al. (1989). *Proc. Natl. Acad. Sci. USA* 86: 3833-3837.
Peters, J M. (1998). *Curr. Opin. Cell Biology* 10: 759-768.
Prowse, A H. et al. (1997). *Am. J. Hum. Genet.* 60:765-771.
Radford, D M. et al. (1995). *Cancer Res.* 55: 3399-3405.
Riethman, H C. et al. (1989). *Proc. Natl. Acad. Sci. USA* 86: 6240-6244.
Saito, H. et al. (1993). *Cancer Res.* 53: 3382-3385.
Sambrook, J. et al. (1989). *Molecular cloning: a laboratory manual*. Second Edition. (Cold Spring Harbour Laboratory Press, New York).
Scharf, D. et al. (1994). *Results Probl. Cell Differ.* 20: 125-162.
Schena, M. et al. (1996). *Proc. Natl. Acad. Sci. USA* 93: 10614-10619.
Semenza, G L. (2000). *Gene Dev.* 14: 1983-1991.
Sharan, SK. et al. (1997). *Nature* 386: 804-810.
Shimura, H. et al. (2001). *Science* 293: 263-269.

Soares, M B. et al. (1994). *Proc. Natl. Acad. Sci. USA* 91: 9228-9232.
Wang, G L. et al. (1995). *Proc. Natl. Acad. Sci. USA* 92: 5510-5514.
Weber, J L. and May, P E. (1989). *Am. J. Hum. Genet.* 44: 388-396.
Whitmore, S A. et al. (1994). *Genomics* 20: 169-175.
Whitmore, S A. et al. (1998). *Genomics* 50: 1-8.
WHO. (1981). *Histological Typing of Breast Tumours*. Second Edition. (Geneva).
Winston, J T. et al. (1999). *Current Biology* 9: 1180-1182.
Winter, G. et al. (1991). *Nature* 349: 293-299.
Wooster, R. et al. (1995). *Nature* 378: 789-791.
Wooster, R. et al. (1994). *Science* 265: 2088-2090.
Wyman, A. and White, R. (1980). *Proc. Natl. Acad. Sci. USA* 77: 6754-6758.
Zaibo, L. et al. (2001). *J. Biol. Chem.* (Papers in Press, Manuscript M108269200).

The claims defining the invention are as follows:

1. An isolated polypeptide comprising the amino acid sequence set forth in SEQ ID Nos: 2 or 4.

2. An isolated polypeptide, comprising the amino acid sequence set forth in SEQ ID NOs: 2 or 4, capable of forming part of a ubiquitin-ligase complex involved in protein degradation through ubiquitination.

3. An isolated polypeptide which has at least 95% sequence identity with the amino acid sequence set forth in SEQ ID NOs: 2or 4.

4. An isolated polypeptide consisting of the amino acid sequence set forth in SEQ ID NOs: 2 or 4.

* * * * *

SEQUENCE LISTING

<160> NUMBER OF SEQ ID NOS: 85

<210> SEQ ID NO 1
<211> LENGTH: 3574
<212> TYPE: DNA
<213> ORGANISM: Homo sapiens

<400> SEQUENCE: 1

```
ggcatggcgg tgtgtgctcg cctttgcggc gtgggcccgt cgcgcggatg tcggcgccgc      60
cagcagcgcc ggggcccggc cgagacggcg gcggccgaca gcgagccgga cacagacccc     120
gaggaggagc gcatcgaggc tagcgccggg gtcggggcg gcttgtgcgc gggcccctcg      180
ccgccgcccc cgcgctgctc gctgctggag ctgccgcccg agctgctggt ggagatcttc     240
gcgtcgctgc cgggcacgga cctacccagc ttggcccagg tctgcacgaa gttccggcgc     300
atcctccaca ccgacaccat ctggaggagg cgttgccgtg aggagtatgg tgtttgcgaa     360
aacttgcgga agctggagat cacaggcgtg tcttgtcggg acgtctatgc gaagctgctt     420
caccgatata gacacatttt gggattgtgg cagccagata tcgggccata cggaggactg     480
ctgaacgtgg tggtggacgg cctgttcatc atcgggtgga tgtacctgcc tccccatgac     540
ccccacgtcg atgaccctat gagattcaag cctctgttca ggatccacct gatggagagg     600
aaggctgcca cagtggagtg catgtacggc cacaaagggc cccaccacgg ccacatccag     660
attgtgaaga aggatgagtt ctccaccaag tgcaaccaga cggaccacca caggatgtcc     720
ggcgggaggc aggaggagtt tcggacgtgg ctgagggagg aatgggggcg cacgctggag     780
gacatcttcc acgagcacat gcaggagctc atcctgatga agttcatcta caccagtcag     840
tacgacaact gcctgaccta ccgccgcatc tacctgccgc ccagccgccc cgacgacctc     900
atcaagcctg gcctcttcaa aggtacctat ggcagccacg gcctggagat tgtgatgctc     960
agcttccacg gccggcgtgc caggggcacc aagatcacgg gcgaccccaa catccccgct    1020
gggcagcaga cagtggagat cgacctgagg catcggatcc agctgcccga cctcgagaac    1080
cagcgcaact tcaatgagct ctcccgcatc gtcctggagg tgcgcgagag ggtgcgccag    1140
gagcagcagg aaggcgggca cgaggcgggc gagggtcgtg gccggcaggg ccccggggag    1200
tcccagccaa gccctgccca gcccagggca gaggcgccca gcaagggccc agatgggaca    1260
cctggtgagg atggtggcga gcctggggat gccgtagctg cggccgagca gcctgcccag    1320
tgtgggcagg ggcagccgtt cgtgctgccc gtgggcgtga gctccaggaa tgaggactac    1380
ccccgaacct gcaggatgtg tttttatggc acaggcctca tcgcgggcca cggcttcacc    1440
agccctgaac gcaccccggg ggtcttcatc ctcttcgatg aggaccgctt cgggttcgtc    1500
tggctggagc tgaaatcctt cagcctgtac agccgggtcc aggccacctt ccggaacgca    1560
gatgcgccgt ccccacaggc cttcgatgag atgctcaaga acattcagtc cctcacctcc    1620
```

```
tgaccggcca catccttgcc gccacatccc gggtggctct ggggctctga actctgacct    1680
gtgaatagaa gcagcatgca ctttggaaat ccggccttt gaccagaacg cacacctcgt    1740 cgggggggccc agtccagcca cccccagca ctttatgtag agagtgtgac atagacctgc    1800
atatttgtca gtgccatgat ggaagaagct gagcatgtct taccaaaaac agagagaacg    1860
agcctgaata cagcagatgt aggggacagc cgtgggaccg cgtgagaatt gaagcggtgg    1920
ggttcccgca ccctgggctg ctggtggtt ttctcgggaa gcaggaccct cctgactggt    1980
gctcttcctg tgagcggata gagtgataga ctgggtcgtg tgtgagacgc atgtgctcca    2040
ccccactcct tttgggggaa gccaggcaac agtggcctct gggaggggt caggaagagg    2100 cgaacagctc aggcagcgca ggtgtgatgg cacagtacg cagagcaagc tcgggaagtt    2160
ggtaggatct caggcttggg gccgggactc tggagtgaat ccccatttct ctaccggctt    2220
gcttggagtt tggacagaag catttcacct ctgatctcag cttccccacc tgtggagtgg    2280
gtttagtgac ctgagtcact agggaatgtc acctgaatgc acagcccagc ccatgcacct    2340
gccccagccc ctccagcttt ggagccaagg ccatcgttcc agccacttga ctgtcctcga    2400
cggcctgttc cagacagggc gtttgttttg tccatgcctt cctccctgca cgcacacggc    2460
gtcaaaacca agctgccggc cactgtctcc agaacgcaag gctccaggcc cgtgtgtctg    2520
aagcagtgag tggtccacac aggtgccagg agtgcccata tgagatgacg aggaaacccc    2580
tttgcaggtg aggggacagc tttctagaaa agccacacct gcatctgggg acacactttg    2640
gaaagtggga ccctccagcc tggagacccc atggactgat gcctccactg ctgtgtgccc    2700
catgttgtgt taacacctgc gtgtggggac cccatctgag gtcttggctg aggttggcat    2760
ctcctgaaga acagagagca cggtgtccag agctggccct tccccagcc cacagccagc    2820 tccgtgcccg agtgggcgtc cccagcgagc cttccctctc tgccgcttgt ccttgtgtct    2880
gggctgctcc aagtccttgt gctgggcacc ctggacacgt cctgctggtg agggacctcg    2940
ggaaggtgac agtctgtgtg ccttggtgtg gagaccaacc tgaggatgtc ctgggaaatg    3000
ttttcctgat gaatttctcc ttgactggcc tttaaagaac ataagaattc ccattgccca    3060
gcctcagtgc atttggcaaa tgcttacttt gcttcccaga gtcagagaat tggcaaaggt    3120
tcctaaatgg taatctggcc ggcctgggag aaagactcac gagaaaagcc agtggagaaa    3180
gcgcccttcc agggcggcag cagcgggagc cacgcagacc ccgaggcgca cctgctggct    3240
cttgtgtgtg gccccagttt ctagcggctt ttgcagcatt agcctacaag cttgtcact    3300 ccctgccctc tgtggtggtc actgttttc tctcttgcca aatgaggcag tctctgagtg    3360
acggtgactg tggccttgaa gcctggagga ctgttgggca tgtagactgg cacttgaag    3420 attcaccatt gtttaaataa aatcaagcaa atgctttttt accaagagcc cgagcctcgc    3480
tctaagggac gcagtcctag aggcgtgccc tttgggctt gaagagcaca ctgtgggacg    3540
cacgtgcttc tgattaaagg aatctcagat ctca                                3574
```

<210> SEQ ID NO 2
<211> LENGTH: 539
<212> TYPE: PRT
<213> ORGANISM: Homo sapiens

<400> SEQUENCE: 2

Met Ala Val Cys Ala Arg Leu Cys Gly Val Gly Pro Ser Arg Gly Cys
1               5                   10                  15

Arg Arg Arg Gln Gln Arg Arg Gly Pro Ala Glu Thr Ala Ala Ala Asp

-continued

```
                20                  25                  30
Ser Glu Pro Asp Thr Asp Pro Glu Glu Arg Ile Glu Ala Ser Ala
         35                  40                  45
Gly Val Gly Gly Gly Leu Cys Ala Gly Pro Ser Pro Pro Pro Arg
         50                  55                  60
Cys Ser Leu Leu Glu Leu Pro Pro Glu Leu Leu Val Glu Ile Phe Ala
 65                  70                  75                  80
Ser Leu Pro Gly Thr Asp Leu Pro Ser Leu Ala Gln Val Cys Thr Lys
                     85                  90                  95
Phe Arg Arg Ile Leu His Thr Asp Thr Ile Trp Arg Arg Cys Arg
                100                 105                 110
Glu Glu Tyr Gly Val Cys Glu Asn Leu Arg Lys Leu Glu Ile Thr Gly
                 115                 120                 125
Val Ser Cys Arg Asp Val Tyr Ala Lys Leu Leu His Arg Tyr Arg His
 130                 135                 140
Ile Leu Gly Leu Trp Gln Pro Asp Ile Gly Pro Tyr Gly Gly Leu Leu
 145                 150                 155                 160
Asn Val Val Asp Gly Leu Phe Ile Ile Gly Trp Met Tyr Leu Pro
                 165                 170                 175
Pro His Asp Pro His Val Asp Asp Pro Met Arg Phe Lys Pro Leu Phe
                 180                 185                 190
Arg Ile His Leu Met Glu Arg Lys Ala Ala Thr Val Glu Cys Met Tyr
                 195                 200                 205
Gly His Lys Gly Pro His His Gly His Ile Gln Ile Val Lys Lys Asp
                 210                 215                 220
Glu Phe Ser Thr Lys Cys Asn Gln Thr Asp His His Arg Met Ser Gly
 225                 230                 235                 240
Gly Arg Gln Glu Glu Phe Arg Thr Trp Leu Arg Glu Trp Gly Arg
                 245                 250                 255
Thr Leu Glu Asp Ile Phe His Glu His Met Gln Glu Leu Ile Leu Met
                 260                 265                 270
Lys Phe Ile Tyr Thr Ser Gln Tyr Asp Asn Cys Leu Thr Tyr Arg Arg
                 275                 280                 285
Ile Tyr Leu Pro Pro Ser Arg Pro Asp Asp Leu Ile Lys Pro Gly Leu
 290                 295                 300
Phe Lys Gly Thr Tyr Gly Ser His Gly Leu Glu Ile Val Met Leu Ser
 305                 310                 315                 320
Phe His Gly Arg Arg Ala Arg Gly Thr Lys Ile Thr Gly Asp Pro Asn
                 325                 330                 335
Ile Pro Ala Gly Gln Gln Thr Val Glu Ile Asp Leu Arg His Arg Ile
                 340                 345                 350
Gln Leu Pro Asp Leu Glu Asn Gln Arg Asn Phe Asn Glu Leu Ser Arg
                 355                 360                 365
Ile Val Leu Glu Val Arg Glu Arg Val Arg Gln Gln Gln Glu Gly
                 370                 375                 380
Gly His Glu Ala Gly Glu Gly Arg Gly Arg Gln Gly Pro Arg Glu Ser
 385                 390                 395                 400
Gln Pro Ser Pro Ala Gln Pro Arg Ala Glu Ala Pro Ser Lys Gly Pro
                 405                 410                 415
Asp Gly Thr Pro Gly Glu Asp Gly Glu Pro Gly Asp Ala Val Ala
                 420                 425                 430
Ala Ala Glu Gln Pro Ala Gln Cys Gly Gln Gly Gln Pro Phe Val Leu
                 435                 440                 445
```

```
Pro Val Gly Val Ser Ser Arg Asn Glu Asp Tyr Pro Arg Thr Cys Arg
    450                 455                 460

Met Cys Phe Tyr Gly Thr Gly Leu Ile Ala Gly His Gly Phe Thr Ser
465                 470                 475                 480

Pro Glu Arg Thr Pro Gly Val Phe Ile Leu Phe Asp Glu Asp Arg Phe
                485                 490                 495

Gly Phe Val Trp Leu Glu Leu Lys Ser Phe Ser Leu Tyr Ser Arg Val
            500                 505                 510

Gln Ala Thr Phe Arg Asn Ala Asp Ala Pro Ser Pro Gln Ala Phe Asp
        515                 520                 525

Glu Met Leu Lys Asn Ile Gln Ser Leu Thr Ser
    530                 535

<210> SEQ ID NO 3
<211> LENGTH: 3661
<212> TYPE: DNA
<213> ORGANISM: Homo sapiens

<400> SEQUENCE: 3
```

| | | | | | |
|---|---|---|---|---|---|
| ggcatggcgg | tgtgtgctcg | cctttgcggc | gtgggcccgt | cgcgcggatg | tcggcgccgc | 60 |
| cagcagcgcc | ggggcccggc | cgagacggcg | gcggccgaca | gcgagccgga | cacagacccc | 120 |
| gaggaggagc | gcatcgaggc | tagcgccggg | gtcgggggcg | gcttgtgcgc | gggcccctcg | 180 |
| ccgccgcccc | cgcgctgctc | gctgctggag | ctgccgcccg | agctgctggt | ggagatcttc | 240 |
| gcgtcgctgc | cgggcacgga | cctacccagc | ttggcccagg | tctgcacgaa | gttccggcgc | 300 |
| atcctccaca | ccgacaccat | ctggaggagg | cgttgccgtg | aggagtatgg | tgtttgcgaa | 360 |
| aacttgcgga | agctggagat | cacaggcgtg | tcttgtcggg | acgtctatgc | gaagcgtata | 420 |
| aaccctcgcg | tgaagtcggg | acgttttgtg | aaaattctcc | ctgattatga | gcacatggcg | 480 |
| tacagagacg | tttacacctg | cctgcttcac | cgatatagac | acattttggg | attgtggcag | 540 |
| ccagatatcg | ggccatacgg | aggactgctg | aacgtggtgg | tggacggcct | gttcatcatc | 600 |
| gggtggatgt | acctgcctcc | ccatgacccc | cacgtcgatg | accctatgag | attcaagcct | 660 |
| ctgttcagga | tccacctgat | ggagaggaag | gctgccacag | tggagtgcat | gtacggccac | 720 |
| aaagggcccc | accacggcca | catccagatt | gtgaagaagg | atgagttctc | caccaagtgc | 780 |
| aaccagacgg | accaccacag | gatgtccggc | gggaggcagg | aggagtttcg | gacgtggctg | 840 |
| agggaggaat | gggggcgcac | gctggaggac | atcttccacg | agcacatgca | ggagctcatc | 900 |
| ctgatgaagt | tcatctacac | cagtcagtac | gacaactgcc | tgacctaccg | ccgcatctac | 960 |
| ctgccgccca | gccgccccga | cgacctcatc | aagcctggcc | tcttcaaagg | tacctatggc | 1020 |
| agccacggcc | tggagattgt | gatgctcagc | ttccacggcc | ggcgtgccag | gggcaccaag | 1080 |
| atcacgggcg | accccaacat | ccccgctggg | cagcagacag | tggagatcga | cctgaggcat | 1140 |
| cggatccagc | tgcccgacct | cgagaaccag | cgcaacttca | atgagctctc | ccgcatcgtc | 1200 |
| ctggaggtgc | gcgagagggt | gcgccaggag | cagcaggaag | cgggcacga | ggcgggcgag | 1260 |
| ggtcgtggcc | ggcagggccc | ccgggagtcc | cagccaagcc | ctgcccagcc | cagggcagag | 1320 |
| gcgcccagca | agggcccaga | tgggacacct | ggtgaggatg | gtggcgagcc | tgggatgcc | 1380 |
| gtagctgcgg | ccgagcagcc | tgcccagtgt | gggcagggc | agccgttcgt | gctgcccgtg | 1440 |
| ggcgtgagct | ccaggaatga | ggactacccc | cgaacctgca | ggatgtgttt | ttatggcaca | 1500 |
| ggcctcatcg | cgggccacgg | cttcaccagc | cctgaacgca | cccccggggt | cttcatcctc | 1560 |

```
ttcgatgagg accgcttcgg gttcgtctgg ctggagctga aatccttcag cctgtacagc   1620
cgggtccagg ccaccttccg gaacgcagat gcgccgtccc cacaggcctt cgatgagatg   1680
ctcaagaaca ttcagtccct cacctcctga ccggccacat ccttgccgcc acatcccggg   1740
tggctctggg gctctgaact ctgacctgtg aatagaagca gcatgcactt tggaaatccg   1800 gcctttgac cagaacgcac acctcgtcgg ggggcccagt ccagccaccc cccagcactt    1860
tatgtagaga gtgtgacata gacctgcata tttgtcagtg ccatgatgga agaagctgag   1920
catgtcttac caaaaacaga gagaacgagc ctgaatacag cagatgtagg ggacagccgt   1980
gggaccgcgt gagaattgaa gcggtggggt ccccgcaccc tgggctggct ggtggttttc   2040
tcgggaagca ggaccctcct gactggtgct cttcctgtga gcggatagag tgatagactg   2100
ggtcgtgtgt gagacgcatg tgctccaccc cactcctttt gggggaagcc aggcaacagt   2160
ggcctctggg aggggtcag gaagaggcga acagctcagg cagcgcaggt gtgatgggca    2220
cagtacgcag agcaagctcg ggaagttggt aggatctcag gcttggggcc gggactctgg   2280
agtgaatccc catttctcta ccggcttgct ggagtttgg acagaagcat ttcacctctg    2340
atctcagctt ccccacctgt ggagtgggtt tagtgacctg agtcactagg gaatgtcacc   2400
tgaatgcaca gcccagccca tgcacctgcc ccagcccctc cagctttgga gccaaggcca   2460
tcgttccagc cacttgactg tcctcgacgg cctgttccag acagggcgtt tgttttgtcc   2520
atgccttcct ccctgcacgc acacggcgtc aaaaccaagc tgccggccac tgtctccaga   2580
acgcaaggct ccaggcccgt gtgtctgaag cagtgagtgg tccacacagg tgccaggagt   2640
gcccatatga gatgacgagg aaacccctttt gcaggtgagg ggacagcttt ctagaaaagc  2700
cacacctgca tctggggaca cactttggaa agtgggaccc tccagcctgg agaccccatg   2760
gactgatgcc tccactgctg tgtgcccat gttgtgttaa cacctgcgtg tggggacccc    2820
atctgaggtc ttggctgagg ttggcatctc ctgaagaaca gagagcacgg tgtccagagc   2880
tggcccttcc cccagcccac agccagctcc gtgcccgagt gggcgtcccc agcgagcctt   2940
ccctctctgc cgcttgtcct tgtgtctggg ctgctccaag tccttgtgct gggcaccctg   3000
gacacgtcct gctggtgagg gacctcggga aggtgacagt ctgtgtgcct tggtgtggag   3060
accaacctga ggatgtcctg ggaaatgttt tcctgatgaa tttctccttg actggccttt   3120
aaagaacata agaattccca ttgcccagcc tcagtgcatt tggcaaatgc ttactttgct   3180
tcccagagtc agagaattgg caaaggttcc taaatggtaa tctggccggc ctggagaaaa   3240
gactcacgag aaaagccagt ggagaaagcg cccttccagg gcggcagcag cgggagccac   3300
gcagaccccg aggcgcacct gctggctctt gtgtgtggcc ccagtttcta gcggcttttg   3360
cagcattagc ctacaagctt tgtcactccc tgccctctgt ggtggtcact gttttctct    3420 cttgccaaat gaggcagtct ctgagtgacg gtgactgtgg ccttgaagcc tggaggactg   3480
ttgggcatgt agactggcac cttgaagatt caccattgtt taaataaaat caagcaaatg   3540
cttttttacc aagagcccga gcctcgctct aagggacgca gtcctagagg cgtgcccttt   3600
ggggcttgaa gagcacactg tgggacgcac gtgcttctga ttaaaggaat ctcagatctc   3660
a                                                                   3661
```

<210> SEQ ID NO 4
<211> LENGTH: 568
<212> TYPE: PRT
<213> ORGANISM: Homo sapiens

<400> SEQUENCE: 4

```
Met Ala Val Cys Ala Arg Leu Cys Gly Val Gly Pro Ser Arg Gly Cys
1               5                   10                  15

Arg Arg Arg Gln Gln Arg Arg Gly Pro Ala Glu Thr Ala Ala Ala Asp
            20                  25                  30

Ser Glu Pro Asp Thr Asp Pro Glu Glu Arg Ile Glu Ala Ser Ala
        35                  40                  45

Gly Val Gly Gly Gly Leu Cys Ala Gly Pro Ser Pro Pro Pro Arg
    50                  55                  60

Cys Ser Leu Leu Glu Leu Pro Glu Leu Leu Val Glu Ile Phe Ala
65              70                  75                  80

Ser Leu Pro Gly Thr Asp Leu Pro Ser Leu Ala Gln Val Cys Thr Lys
                85                  90                  95

Phe Arg Arg Ile Leu His Thr Asp Thr Ile Trp Arg Arg Cys Arg
            100                 105                 110

Glu Glu Tyr Gly Val Cys Glu Asn Leu Arg Lys Leu Glu Ile Thr Gly
            115                 120                 125

Val Ser Cys Arg Asp Val Tyr Ala Lys Arg Ile Asn Pro Arg Val Lys
    130                 135                 140

Ser Gly Arg Phe Val Lys Ile Leu Pro Asp Tyr Glu His Met Ala Tyr
145                 150                 155                 160

Arg Asp Val Tyr Thr Cys Leu Leu His Arg Tyr Arg His Ile Leu Gly
                165                 170                 175

Leu Trp Gln Pro Asp Ile Gly Pro Tyr Gly Gly Leu Leu Asn Val Val
            180                 185                 190

Val Asp Gly Leu Phe Ile Ile Gly Trp Met Tyr Leu Pro Pro His Asp
    195                 200                 205

Pro His Val Asp Asp Pro Met Arg Phe Lys Pro Leu Phe Arg Ile His
    210                 215                 220

Leu Met Glu Arg Lys Ala Ala Thr Val Glu Cys Met Tyr Gly His Lys
225                 230                 235                 240

Gly Pro His His Gly His Ile Gln Ile Val Lys Lys Asp Glu Phe Ser
                245                 250                 255

Thr Lys Cys Asn Gln Thr Asp His His Arg Met Ser Gly Gly Arg Gln
            260                 265                 270

Glu Glu Phe Arg Thr Trp Leu Arg Glu Glu Trp Gly Arg Thr Leu Glu
            275                 280                 285

Asp Ile Phe His Glu His Met Gln Glu Leu Ile Leu Met Lys Phe Ile
            290                 295                 300

Tyr Thr Ser Gln Tyr Asp Asn Cys Leu Thr Tyr Arg Arg Ile Tyr Leu
305                 310                 315                 320

Pro Pro Ser Arg Pro Asp Asp Leu Ile Lys Pro Gly Leu Phe Lys Gly
            325                 330                 335

Thr Tyr Gly Ser His Gly Leu Glu Ile Val Met Leu Ser Phe His Gly
                340                 345                 350

Arg Arg Ala Arg Gly Thr Lys Ile Thr Gly Asp Pro Asn Ile Pro Ala
            355                 360                 365

Gly Gln Gln Thr Val Glu Ile Asp Leu Arg His Arg Ile Gln Leu Pro
    370                 375                 380

Asp Leu Glu Asn Gln Arg Asn Phe Asn Glu Leu Ser Arg Ile Val Leu
385                 390                 395                 400

Glu Val Arg Glu Arg Val Arg Gln Glu Gln Gln Glu Gly Gly His Glu
                405                 410                 415
```

```
Ala Gly Glu Gly Arg Gly Arg Gln Gly Pro Arg Glu Ser Gln Pro Ser
            420                 425                 430

Pro Ala Gln Pro Arg Ala Glu Ala Pro Ser Lys Gly Pro Asp Gly Thr
        435                 440                 445

Pro Gly Glu Asp Gly Glu Pro Gly Asp Ala Val Ala Ala Glu
    450                 455                 460

Gln Pro Ala Gln Cys Gly Gln Gly Gln Pro Phe Val Leu Pro Val Gly
465                 470                 475                 480

Val Ser Ser Arg Asn Glu Asp Tyr Pro Arg Thr Cys Arg Met Cys Phe
                485                 490                 495

Tyr Gly Thr Gly Leu Ile Ala Gly His Gly Phe Thr Ser Pro Glu Arg
            500                 505                 510

Thr Pro Gly Val Phe Ile Leu Phe Asp Glu Asp Arg Phe Gly Phe Val
        515                 520                 525

Trp Leu Glu Leu Lys Ser Phe Ser Leu Tyr Ser Arg Val Gln Ala Thr
    530                 535                 540

Phe Arg Asn Ala Asp Ala Pro Ser Pro Gln Ala Phe Asp Glu Met Leu
545                 550                 555                 560

Lys Asn Ile Gln Ser Leu Thr Ser
                565

<210> SEQ ID NO 5
<211> LENGTH: 2340
<212> TYPE: DNA
<213> ORGANISM: Homo sapiens

<400> SEQUENCE: 5
tatttgtttt gtagacaggg tctcgctgta ttgcccaggc cggtctcgag ctcctggcct      60
cgattgatac tcccgcctgg gcctccaaga gatggggtcc gaggcgagcc cacggcgacg     120
tgcgcggctg ctcaggtgag aggacgcctt cgcggtcacc acccgcggac ctgggagacg     180
accccgctca gcggcctcgg cggagcccag ctggagcagg cgtgcgcggc tcccagcagc     240
tgcaggaaca ggcgcccttt gggcggcgcc gcatggcagg gcctcccttt ccagaccggg     300
cgcgcatccc cggatctctt gggccgcgcc ggccgccgcc cctccaagcc ctccccgggg     360
cttccgcagg gagctcggga tccccgaagg tccctgcaga gctccgcagc tcgggccttt     420
tggttaccat aaggcggaga cgatggaacg cgcgttgttt caatggacaa aagggcttct     480
aggcgccctt tggggttctg ctgctgcct ctgtatttgg aggctgtaag gcgcatcttt      540
ctactcaccg gccggcgcgg cacagtttcg ggcgccggaa gcgggacgca cgggcgcgag     600
gggcgacccc tatctccaca aaagccgcgc gcgaagtgg tcgccgagca gcctcgttag     660
cgcagtaggc agcgcgtcag tctcataatc tgaaggtcgt gagttcgagc ctcacacggg     720
gcagtctaac gttttgcact cggcatcacc actttctttt ctcatgcccg tcacgggcgg     780
cgccctcacg ctgagggga gggcagcagt gcggggtctc tgaggtcgcc gccccgcggg     840 gaggggtgg cgcggccggg gcggagctct acgtaggggc ggggctaggc tctccagggg     900
gcgtggcgag ctctgcggcg ggggcgtggc tcggcgctgg cggggcgggg ccgcgctgga     960
gcgtgcgcac aggcggcagc agtggccgtc actgggcggc atggcggtgt gtgctcgcct    1020
ttgcggcgtg ggcccgtcgc gcggatgtcg gcgccgccag cagcgccggg gcccggccga    1080
gacggcggcg gccgacagcg agccggacac agaccccgag gaggagcgca tcgaggctag    1140
cgccggggtc gggggcggct tgtgcgcggg ccccctcgccg ccgcccccgc gctgctcgct   1200
gctggagctg ccgcccgagc tgctggtgga gatcttcgcg tcgctgccgg gcacggacct    1260
```

```
acccagcttg gcccaggtct gcacgaagtt ccggcgcatc ctccacaccg acaccatctg   1320
gaggaggcgt tgccgtgagg gtgagcgcgc ggggtggcg gggccgggag ggcggggg     1380 tccctgccag gtggaggcct cggagctggg agtggcgggg gcggtggccc cggccgggg    1440 ccaccagttg ggcgcggggc ccggcgatgt ggtgttttgg gtgtgggtgg ggagcggccg   1500
cggtgacacc acgttgaggg ggccaggag gtatttgagg cggttaggga gggtccgagg   1560
ggtccaagag aggcagacgg ggtagggagg ggttgagggc gtcagggagg catcgaagag   1620
gccctgacgc ggggcacggg acaccacggg gccgaggccg tgccgggagc tggggctggg   1680
atccctcgag gtctgcgcgg ggcctaagct gacgcctggg ggccgcctcc tctgcccctg   1740
tcttgaaggc gagccgaggg tgccccgctg gccctgacca gagacgaggt gaacttgaag   1800
aaatgggagc aggccgggcg cggttttcacg cctgtaatct cagcacttag ggaggccgag   1860
gcgggcgggt cacctgaggt caggagttcg agaccagcct ggtgaagatg gtaaaacccc   1920
gtctctactt acaaaaatac aaaaattagc cgggcgtggt agcgggcgcc tgtaatccca   1980
gctactcggg agggtgaggc agaagaatgg cttgaacccg ggaggcggag gttgcactga   2040
gccaacatct gggccattgc actccaccct aggcgacaga gtgcgacttg gtctcaaaca   2100
acagcaacaa aaaaattac gggagtaggg gaagcccagt gtcggggggct cctgatggtg   2160 ggggcgtaga gagacggatg gatcacacgc gtgcgggctg acttttgcc ttcagcaata   2220 ttggatgtaa cagatcacag gaggagatgt ttatttaatc tggagttcaa ggctctctct   2280
gtttaaaggt tgacagctct ttgatgttca agcagctcat atttaggtaa aaggacagg   2340
```

<210> SEQ ID NO 6
<211> LENGTH: 2072
<212> TYPE: DNA
<213> ORGANISM: Homo sapiens

<400> SEQUENCE: 6

```
aaggaagctt tttgatctag gcttcaattc ttggtcccag ctgaccataa gctccaggtc     60 cttttgtggag tcatgtcacc tctctgcact tgttttctct gttaaaatgg agatgacagt   120
ggtgactctc ttatgggact gctgtaggat gcagtgaggt gatgcccagc atggcttggc    180
atggtacaca gcacgtggaa agctcaatgc aggtgttgcc agtagcagct cttggcccat    240
gtgcagttct gtagttgtgt ggattagtcc ctggcggtct ttcctttcaa aggctagcgg    300
agacccaagc cggaggacct gggattttgc ttgggacgtg ctgggtgttg gtgattgtga    360
aaagtgcagc tgtggtgggg tgggagtagg ggacaaagag gaaggtgctg tcagcaggtg    420
agggtgtgag gacagggggtt gcgggaggtg tccagggccc tgcactgggc cctggccaag   480
cctagccagt ggagaaggga caatgttcac cccttccccc atgtcttgca cggtcccctc    540 ttggcccttgg gctgagttga acacacaggc agcacaggga agtacatggg gtggactggc   600
ctctggcact gtctgaaccc taacaccagt ggtgaatttg tttccatgga acatggcac    660 tgtgtccaga caactgaatt ctgcctcacc ttgttcataa actagggatt gtctgatatt    720
ggtttgtgtg gttaggcttc tagagcttat tagaatagac attgcagatt attattttgt   780
aaagggtgac attgactaaa atagaataat gtcttcatcg gtgaacaagg gtgtttactg    840
aatgtggaga agtcagtgaa atctccacag tgacagatgc actctggaga tggggctgag    900
gctaggtgtg cacctcccct gccagccatc agcagcctgc ccacgtcgt cgcgttatga    960 gttgttgatc ttaaatttct gcaaatgttt cttgttacag agtatggtgt ttgcgaaaac   1020
```

```
ttgcggaagc tggagatcac aggcgtgtct tgtcgggacg tctatgcgaa gcgtgagtga    1080
atctatttgt taccatccat gattaacttt gtaccagaag cagacagtgc acatcaatga    1140
caaataatca aagtgattta gtccacactt ttgttttctc agacaccatc ttacagtcac    1200
attttgaata gagcactggt agtaacagca ctaaaattag ggaggggaca ccgtattctc    1260
ccattctggg catcgtagat actagtgtct tttaccaggc atcgaggccc tttagagctg    1320
agaaatgtag gctgcaccag agcgacttgg gtgttcctgg aggctgcctg tttctctggc    1380
ttctgggcct ccagccttca ggatgggact gcctgtggtc attgggaaat gaagctgtgg    1440
tgccttctgt ccaagcccca ggtacggaga acagccccc tgctagagtt ctccttccct    1500
ttagcattct gtgagcaggc tgagcccccc agcccgttt catgtttctc tggttcaccc    1560
gctttccaga gtcaactgtg acactcaccg atcaggcaga ggctccttgg ccccaggctg    1620
tcttcccgcg ggtgtttctt cagtgccagg gactttccca tttcttgctc actggacgaa    1680
gctcttggct tttttggatg gtcagagggt ttctgtgagt gtctcatacc ccacgttttc    1740
atcttctgac cattctttga gcttcttttc tttttttctt ttcatttctg caaggcagtt    1800
gctctttgag tttcttaggc catttgggtc atatcatctc aaagtgacat gaagacatat    1860
ttctctctaa gagttgtcag caccaaaagt catgtcccgg tagggacaca ggtgtttggc    1920
ctgcccaggt gttagggttt cctgtaacag ccataggagt gtacacatgg atgctccttc    1980
cagctgtggg ggtcggaggt gttgcctgag cactgagtcc tcctgtcctg tgggagaggc    2040
catccgggca taggcaggca ggaggcagtg tg                                  2072

<210> SEQ ID NO 7
<211> LENGTH: 2087
<212> TYPE: DNA
<213> ORGANISM: Homo sapiens

<400> SEQUENCE: 7
agagttgtca gcaccaaaag tcatgtcccg gtagggacac aggtgtttgg cctgcccagg      60
tgttagggtt tcctgtaaca gccataggag tgtacacatg gatgctcctt ccagctgtgg     120
ggtcggagg tgttgcctga gcactgagtc ctcctgtcct gtgggagagg ccatccgggc     180
ataggcaggc aggaggcagt gtggccgagg gtagggcagg gggtgggcac agaagagggg     240
ataggaggac agggcattgg gagatttctt ttcactgctg attcttgacc ccttgaaagt     300
gtttgcaaaa tgcggagaat tcacatgatc tgtttccgac agtgtttatt ccccgcagtg     360
ttagtctgca gtggccaaag caaatgtcag tgttcatttt cacagcgcag caactgtgtt     420
tctgtgaatt tgctttaagg cttatccagg agaaaattac ttagctttgg gaacaggtgg     480
tggaagaaaa tcagccttag ctccagaaac gggtggtgta gttgggcaac cttggatgac     540
ctgtgacgag gctggcctga gttagcaggc tgggaaacgc caggtgggtg ctgggcaaag     600
tgagtatgtt agccggggta agtgttctct agacggtcat cccagatgct cacctgccag     660
gacacctgcc ctcccacctc ctgagcccca gtgagctgtg gcctgggcc tgccgggagt     720
gtgctggccc cggaggagt gtgatcaaat atggaaagga tttccaagct tgctgccacc     780
gtgagtttct ggtggcacca ctgatggaag gaaaacgtgt cacagtgttg ttctctccag     840
caggtttctc agagccacct ctctgtgtcc tgggtggctg cataaacacg aggggattgt     900
atcacactgg tgaggggcag gcattgggtc gtattcacgc tgtttgcaca gtcctgtaaa     960
gggagccatc cttagccctt tccctgctgt gtctgttcag gtataaaccc tcgcgtgaag    1020
```

-continued

```
tcgggacgtt ttgtgaaaat tctccctgat tatgagcaca tggcgtacag agacgtttac      1080
acctgccgta tgtacctcct gcgagctttg gcttctgcgg cagccagcac ggccaagaac      1140
tgcatgggga gggccctctg attcacacat gggacagctt tggtcctgga gcaagcggac      1200
ctcgtggctt tttgtcatcc tttcacgttc acttgctgca gcgtggctct gcttcagctg      1260
tgacagagat cacacctgtg tgttggaccc aggctgcatt tggcttacct ttctgcagtg      1320
gtttctgggt actaccagtc gagatcactt taatgcacat tttcacatgt atcgtttatt      1380
gaggagctac tgcagacaca gagaggaacg aacagagtag aagctttaaa attttattct      1440
aaagtgaaat atgaatattt gacttctgac ctttattagt tttaatcaca ttttaatagc      1500
ctatgtgaat taaaaatcac atatgcatat accctcaata gacaaaggca ggtagcaaca      1560
gttgactcct tttttttttt tgaggcagag tctcactctg tcacccaagc tggagtgcag      1620
tgtcacaacc tctgcctcct cggttcaagt aatactgcca cctcagcctc ccaggtagct      1680
aggattacag gcatacacca ccatgcccag caaattttt tgtattttta gtagagatgg      1740
ggtttcatca tgttggccag gctggtctca agtgatctgc ccatctcggc ctcccagagt      1800
tctgggatta caggcatgag gtaccgtgcc tggctaacag ttgactcttt agaacttaat      1860
tcttcttttt ggccagacat ggtggctaat gcctgtaatc ccagtgcttt gggaggccga      1920
ggcaggtgga tcatctgagg tcaggagttc gagacctgtc tggccaacat ggtgaaactc      1980
atctctacta aaagtacaaa aattagctgg gtgtggtggc gtgtgcttgt aatcccaggt      2040
acccagaggc tgaggtgggg gaatcgcttg aacccgggag gtgaagg                   2087
```

<210> SEQ ID NO 8
<211> LENGTH: 2077
<212> TYPE: DNA
<213> ORGANISM: Homo sapiens

<400> SEQUENCE: 8

```
gctgatggag agcgggcagg tagggtggag aggcaggaag gttggtggca gccacatggc       60
tgagggccta gagcctggcc agggagtcgt ggagagaggc agtgggtggg ctggggttc      120 aggcctgcct gaagggagg cagctggtgc agtggcccat accccatggg gtgaaggcct      180
gggcagggcc caggggcagc ttcgagggtg acctggagct gctcaggaag tgagatggcc      240
cagcctgacc tgaccattgg ctggcaagga acgggatgga gaagttgtgt cctgggcctt      300
cagcgagtgt gacattgtca ttgttgggat agctttaaag atctgattgc ttatgacatg      360
ccttgtagcg ctaccagcat cttggcattt ggcaggtcta gtccagctcg ctgtttgcac      420
gtcttctgtc ttattcctag aagagagagt tcccagcctt gcttgatttc ccccattga      480 tgggaggctc atcacttcat gggagactca ttttacttag gccttctgag gatagtttca      540
ttctgatagt tttttttttt tttttttttt ggagactgag tttccctctg tcgcccgggc      600
tggagtgcag ttgtgtgatc tcggctcact gcaagctcca cctcccaggt tcatgccatt      660
ctcctgcctc agcctcccaa gtagctggga ctacaggcac ccgccaccac cccggctaa      720 ttttttgtag ttttagtaga cgggggttt caccgtgtta gccaggatgg tctgaatctc      780
ctgaccttgt aatccgccca aagtgctggg attaaaggcg tgagccaccg cacccggcct      840
cattctgata catctttaga ggcttggtgt gcatgtgttt ggagggctct tgcaagcctt      900
ttgtgagtcc tcatggttcc ttcctccctc tcggggttcc tgggctccct gcggcacgct      960
gggtctaaca cagagacttg ctcttttctct cctcctgtag tgcttcaccg atatagacac     1020
attttgggat tgtggcagcc agatatcggg ccatacggag gactgctgaa cgtggtggta     1080
```

```
agtcccggag cctcgcgacg aggtctgtgc acgggcagga gtggtgcctt acgtggagga    1140
atttgagggc ctcttctacc tgggtacaag ctggcccaga tgtgcgtttg aggtaattac    1200
caaaaaattc ttgctctgtc acttttcagg agccaatttt attttccaaa tgagcaaagg    1260
tttgcttaga gcaacacttc ggccttgtgg cccgtccttg actctctgg tctgagggg     1320 tggcttgtga gggcctttgc ttcctggacg ctgaggccca tcgcgcacat gttggcgggg    1380
tctggagccc gccctcagcc aggtccttcc gttcctggtc tttgcccccc atgttccagc    1440
catggtgcac tctgacgtct gtttccttgg gttctgctgt ggacccgctc tgaccaccct    1500
gcctcccgcc ccctgtgccc tcctactgga gcctctcgaa cggaaagccc tgctctgact    1560
ttgttgagct ctgggcaggt ggctggcccc tgctagaaag tgctagaacg ttgcaggcgg    1620
aagtccaggc tggtggcaga gtcgtctccg tttcccttct cccggcagcc tgcttgccgt    1680
tggggtctga ggaccgtga  ggacatttct ttcctgttcg ttgggtctgc catggcagtg    1740
cctgtctagt cctgggtact tgatcatggc tggagatgga agtctggctt tctttttat    1800 taaattcccg ttttcggtg  aagttttcct tctctttgtt aatcttttg ggtacagtag     1860 tgaaagtttc tttcgagtct agccccgcc  ttttctcctg atctccaggc gtgttggatg    1920
ccccccaccc ctcactgtgc gcctgggcac ttgctgggtg ccgtggcctg gtctcctcaa    1980
gaggccctgg ccccggcctg cgggcaaagt ggagtcaggg cacctgctct gcgcaggccc    2040
ggggtatgcg cgcgtctcag gcttggggaa gcgtccc                             2077

<210> SEQ ID NO 9
<211> LENGTH: 2889
<212> TYPE: DNA
<213> ORGANISM: Homo sapiens

<400> SEQUENCE: 9
ggatgtttcc tctgagagac cagcccggca gctcacaggg tgggcagatt gctttccttt     60
cttttagtgg aggaagggta attgttttac ttactggcag tgagtaatag agtaaaaaaa    120
aaaaccccaa aaaacaaaaa gcagtggata attggggaaa gtggagtctg tgagagaaca    180
gcaccagctc acgcttgacc caggctcgtg agccacagaa atgatggaat tctctccttg    240
gttgctggag ctggcagtct catgggtccc agctctccca gaagggggtg aggctaggct    300
gtccttcctt ataagcatgt ggctgctgtg gccagagcgt gctggggccc acccgcctct    360
gcatttgcac gatcggcgcc cggacacgcg agatcgcacg gcaacgcac tcctcggctc     420 ttcccgctcc tgagcgcccc tcccggggtc ttggcgtctc tctcctcccc tgcacttcgg    480
ttttgaagca atcccaggc  ccgtggcatt tcagctgtcc gtccctccgg gcagcgccct    540
aagaaagggg gtgtttcctg catctccgtg tcactgccac acctgacaaa agtggcacac    600
ggtccttgtg ttgcctgttg cccaggccat gggatgcttc cctgatcatc tcaaagcctc    660
ctttgaatgg caatttgttc agctcaggac gcgaacgagg cccttgcact gctgttgttc    720
actctttcct gttgggagat gcacccccct tccctctgtc tggtcggcac ctcacccgt     780 gtcactttct ggattattct gcctcctcct ggtgtccacc tgcatctcag agctggaaga    840
tagtgctggg attcgaggca cctcgagggt gggcgtgcag gtcccatgtg ctggtctggc    900
aggagcttct ctgtgccatt gcagtgcggg gagccgtgcg gggccgccct tgctctggcc    960
cgggagccac tcatgaccct ttgcccatct cctcctgtag gtggacggcc tgttcatcat    1020
cgggtggatg tacctgcctc cccatgaccc ccacgtcgat gacctatga gattcaagcc     1080
```

```
tctgttcagg atccacctga tggagaggaa ggctgccaca gtggagtgca tgtacggcca    1140
caaagggccc caccacggcc acatccaggt gtgtgcagcg gcggggctgg gtcctcactg    1200
tcccagggct gtcctgtgtg ggctccagcc aggcctgccg tgctattctc agctgcagac    1260
ctgggctgta gcagatcggc gggtgggagg gaggctccgc cctgccctgc tgtgcattgt    1320
ttacgcctcc gtggcgcagt ggactctgca gcggtcactt gctggacccc tcttgattct    1380
gctctcagtt agagccgctg tttctttgca acttcagttc ctctgtcttt ttttcctgtt    1440
tgcaagaata tcagtgtgga atcaagtgcg ctctctgttc tctgatctgg tctggcagtg    1500
gcccccacgg tgagcacagc gtgtcatctg ccacaccttg tgtgtgagat gcagcccttt    1560
tgctgctctg tgtcacgctg ggaaatgcaa acgccactct ctcagatgtg ccactgcctc    1620
ctgctcttgg gggagtgttg ctcagggaga ctcagctccc tccgctggca ccgcgttggt    1680
cgcatcttgg gtgcctgcag tggggtttgg tgggtgtggt gagggagggg tcgtggccac    1740
ctgcctgggg tggggatgc tgtgatggac tctgttcctc actcttctct ttccttgtgt     1800
tgcaaacact gaagattgtg aagaaggatg agttctccac caagtgcaac cagacggacc    1860
accacaggat gtccggcggg aggcaggagg tgagcccacc agccggccct gtgttcatat    1920
ggtgcggacc tttcctttcc ccacggggaa agtacagacc catgcgggag agaagtcagc    1980
agcatgcgac ctgcatggtg gctgtttcac atggttcagc cggtattgtc agtgcagacc    2040
gtgcatccgg cacactcgag aacagcatc gtgcgggcgg gcaggttgcc ggtcccctcc     2100
ccctgcagaa cgaacgaacc acacaggccg tttcttcagt tagctctgct ttgcccctct    2160
ggcgggcaca tccacttgct gaggggttgc tgggaggctg cttctaggat gtgagctgca    2220
gggagacccg agggctgcac ccagagttcc tgtgtttccc atccttgagc agaccgtgtg    2280
gaggcttccg gatcgtgcca gtgcagcggg gaagcctgtg tgtgattgtt tgcctgagta    2340
ttttaatatt gcccttgagt tttagctttc aaggatctaa gtcttactgc cctctcaaaa    2400
tactcttaag aaggaaggtg cggtggctca cacctgtatt cccagctctt tgggaggctg    2460
aggcaagagg atcacttaaa gtcaggagtt caaaaccagc ctgggcaaca tagtgagacc    2520
ctgtctctac aaaaaccaaa aatattagct gggtatggtg gcatgccagc tactcaggag    2580
gctgaggtga gaggattgtc tgagcccagg aggtggagac tgcagtgagc tatgagcgca    2640
ccaccgcact cccatgtggg tggcagagtg agaccctgcc tcaaaggaa aacaaaaaa      2700 ttagccaggc atgctaccat gctacgggg tatgccatgt tgcccaggct ggtcacaaac     2760
tcctgggctc aagccgtctt cccaccttga cctcccaaag tgctgggatt gcaggtgtga    2820
gccatcgcgc gcggccaggg tgtgcttttc ttagctagtt tgagttgtgg tggtttcccc    2880
atcagccag                                                            2889

<210> SEQ ID NO 10
<211> LENGTH: 4378
<212> TYPE: DNA
<213> ORGANISM: Homo sapiens

<400> SEQUENCE: 10
gtggttttca gaatagatct taaacgtatt ttgtaacatt tattcccaag tcttatgttt      60
ttttgaggat tttgtacata gaattttttt aaatttttatt tttatatttt gtgctgctag    120
gacataaaaa tccaggtggc ttctgtgttg accatgtggt cctgccaggt gctcagtgca    180
gctcctgcag tgatttctgt ttcttgtcgg agtttggagc agtgatgtat gaaagcgatt    240
gaccatcgtg tttcctcttt tttgtgagtt gcttatgcgt ccctttcaga gttaggtcta    300
```

-continued

```
gataatgact ggaaacactg tattgagctg ggaacttgga agtttgggtg aattctgtaa    360
attgtgtaga atcaaaccat taagcacgaa atatcctcag caccatgtga tggcagaatg    420
cagggcggac tggtgggggct gcggagtttt tgggaaccgc cttaacatac ctgcttttcc    480
tttgaaaaag gaaaatccac ccagtcactg gccgagggct cagtgcatcg tccttggctg    540
actcgcacgg ctcaggggttg gtggtgaggg cttctggaac actcaggctc ccaggagcca    600
gagaagcagg ctgaggggct gtgctgtgca gggccagagt ctgtgtagat gctgttcctg    660
ccccaccggt gggcatggaa gggaggccca ccctgagttc tggtcatggc gtgccccc       720
gcctcacctg gctccctgt agcccctgct gcctccgacc cagcagacca agggcccgga     780
accttcactt tttgttggca ggcacctctg acgtggggtc aaatccgca gctccccttt     840
ctcttcccag cgccaagtcc atcctccccc accaagaggg ccctgcaggt gcctgtgcac    900
tgacaaagaa ggacacactg tgtcctctca gcggcacagc cggcagcctc ttcacagcct    960
cctgtcatat ggatattcat gacctgtgtt cttttggaag gagtttcgga cgtggctgag   1020
ggaggaatgg gggcgcacgc tggaggacat cttccacgag cacatgcagg agctcatcct   1080
gatgaagttc atctacacca gtcagtacga gtgagtgcgg ctcctgctcg gtgctggggt   1140
agccctctcc tggtgtgtgc tgggaccag ccctgtcccg gtgggtgctg ggcatagtc    1200
ctttgtctca gtgggtgctg gggttcagcc ctctctcctg ctgggggctg ggagtacagc   1260
ccctctctct ctgggtgctt ggagcatagt tcgctctttc tgtgggtact tggaacacag   1320
cccctctctc tgtgggtgct gggagtgcag gcctccctgt agctgctgtg gcacagcccc   1380
agacccatc cttcacccgg gtgtctgttt ttatctgatt tcctgtcacc cctgccaaca    1440
ctggcactct agagctcagc cccgctcagc ccagtgcggg gatcccctcc atggtgactt   1500
gggctccttt ctcctgggta atggagcaaa ctggcacttc cttttccctc ccacctaaag   1560
ctctgccctg gcgctgatgc cccccttaac cccagaagtc ctgttggaag cgtgcgtgct   1620
ggtgggtggt gggggtgagg gctcccctgg gcgcattgct gcccacaggc ctggtggaca   1680
cctgccctg gttgagctga gctgcccgcc ctaccccgcc ctgcaaagct catccctggc    1740
accttgggcg ttctcagtcc tgcctgcccc acgaggtctc ctgtactgac ccgtccgctc   1800
cccacagcaa ctgcctgacc taccgccgca tctacctgcc gcccagccgc ccgacgacc    1860
tcatcaagcc tggcctcttc aaaggtacct atggcagcca cggcctggag attgtgatgc   1920
tcagcttcca cggccggcgt gccaggggca ccaagatcac ggtgagtggc ggctgacctg   1980
gttggtgggg ctctgggggc acctggccca agtgggctgt ggagtcaggg aacttgggca   2040
gacactgatc cccggcaccc ttgctcctca gagtgggctt gcacctgcag ccccgggagc   2100
ttgggaaagc agattctcgg gccccagcca gccccactga accagaattg catttccacg   2160
agaccctcag ggagtctgtg tgcttccaag gtggccttcc cacagcaccg ctcagccccg   2220
gccaccctgg cagccctgtg gggtttagga agtctggaca gcagacccca cacagaggct   2280
cagatttaac tggggacagc ctgggaaagg ggccctcca gcagctgcat ggagacccctt   2340
gtgcttgcag acagctccca ccctgtctga gcttcagcag ctcctctcct tggagtggcc   2400
tgagggtggg ctgtgtggtg agcccagcag tgaacagggg ctcattgtcc catgccaggg   2460
ctcctggcac atgctgcccg cctgccctga atggttattg gggatcctgg cagacagcgc   2520
ctgaaggggc gaagcctatt ccccgagcct ccagggatca gggccacatc tggcataatg   2580
gggcattccc tggaccccag agtttttggct cctggactcc tcacggagtt ttggggctga   2640
```

| | |
|---|---:|
| cgcatcttcc cagggctcgg ctcccgagct ctgcctttca ggcagacaga tgtgggctgc | 2700 |
| cccccttgggc tgctgcccag ctctgggatg ttctttgaac ttctctgggc gcagttgagc | 2760 |
| aggtatgagc caccgtcctc agggcactc ataggtgttg ctggccctgc cactttctaa | 2820 |
| gggattctga gacttcttct tctgtaaggg acgttgctaa gtcagtagga gggctggtgc | 2880 |
| cagctcgctc agccagaggt ggatctgggc tggagcccac acagtggtac tgctgctgct | 2940 |
| gctggcctga gccctgctga ctgccacctg ctccacaggg cgaccccaac atccccgctg | 3000 |
| ggcagcagac agtggagatc gacctgaggc atcggatcca gctgcccgac ctcgagaacc | 3060 |
| agcgcaactt caatgagctc tcccgcatcg tcctggaggt gcgcgagagg gtgcgccagg | 3120 |
| agcagcagga aggcgggcac gaggcgggcg agggtcgtgg ccggcagggc cccgggagt | 3180 |
| cccagccaag ccctgcccag cccagggcag aggcgcccag caagggccca gatgggacac | 3240 |
| ctggtgagga tggtggcgag cctggggatg ccgtagctgc ggccgagcag cctgcccagt | 3300 |
| gtgggcaggg gcagccgttc gtgctgcccg tgggcgtgag ctccaggaat gaggactacc | 3360 |
| cccgaacctg caggatgtgg taaggatgcg gcgggtactg gggcctgaag gtgggacagc | 3420 |
| atgggcttca gcgagggccc cagccccaca cctagcacag gcggagaggg cctgtgacct | 3480 |
| cacagagggc ggcagccggt gctttgggac aggagtgcgg cctctgaccc cttgggccat | 3540 |
| gttccccagc acctgagcaa gcggccgcgc agctgggtcc cgtcttggag gctcctgtcc | 3600 |
| ttccacccct tctggggtac ctcagagctg caggggcatg aggcttccag atgcctcaca | 3660 |
| tccctgcaat agtgccgctc ccccagggc ttctaaagct acttgtttgc agtcaatcaa | 3720 |
| gtgaaatatc atgtaaactg tccagcagct ttgaaagtag agaatgaaca aggccccttc | 3780 |
| cccacccacc ctgtggaaag cccgtctggt ttggtgtcct cctggacagc gtcttgccgg | 3840 |
| tcacctttgg ccatctcccg gtgcgtggtt cagatgtggg tcctgctttc ctgccccctc | 3900 |
| cctcctctgt gcctgcctgc ctctgctgtg ccgggccagt gccttggtgg ccagtggagt | 3960 |
| ggacaccagc tgcgactgcg tgggaggggc tggcattgcc gctgccactg cagggcttgg | 4020 |
| gcggctgaca tgggacgagg cttgcacagc tgccagctcc tgtctcgctg acttttttta | 4080 |
| tacagttttg tctgggccac cgccttcagt gccacgggcc ccttgccgtt caggctgctc | 4140 |
| ctcatagatg aacaaggccc tgccccgtgt ccttacccct tagagctgtt taaattcaaa | 4200 |
| tgaactgaaa ctgaatatga aaaatccagg ccctcagccg cccaggccat gtttcaagtg | 4260 |
| ctccatggcc acatgtggct ggtggacagt gcagctctag aacattccat caccacagag | 4320 |
| ggttctgctg gacagtggcc ttgggggctg ttttgagggt ccgcctgtca gtctcctg | 4378 |

```
<210> SEQ ID NO 11
<211> LENGTH: 3174
<212> TYPE: DNA
<213> ORGANISM: Homo sapiens

<400> SEQUENCE: 11
```

| | |
|---|---:|
| atagctaaaa aaggaaaaag ctctgttacc cttcaaacat ctcagaactc ctaatacctc | 60 |
| acagtgggct cagagccagt ttgcgagtca cagcacgtgc tgcagccact gaccaggaag | 120 |
| acctgtccag cctccgtccc cagctaacct gcaggacagt ccctgacgtg ctgaatatgg | 180 |
| gggctcccgg gccttccct gtctagttta tggatctgca gggcctggcc acggcacctg | 240 |
| tacagggaat gcctgttgct ttttttctga ccacagtgcc gatggctgca cctgcctctg | 300 |
| ggccctggaa cttctccccg agcttgagaa gccctctgag gccaggccct ggtccacggg | 360 |
| gctgttcttt cccccggcct ttggagcctc agtgggtgat tccaggccag cccttactt | 420 |

-continued

```
ctcgtcatct gttggaagaa tttagctgct tgcaagacag acataagtgt cttcctgtct    480
gatgttgacc tcaaagccat aaatgggtgt ttgcgacttc tgagttaatg tcagctgcag    540
gctgcctgta ttagagctaa ttgtatgggg acataactcc cagacattaa gattttttt     600 cacattgggc ctcctttatg aaatgtgtgt tttggaacag agctctctgg gcctgcagag    660
acctcgtttt agttcagtgt ttcagcattg tgcagtcagt gggtgaatcc ctcacgggtg    720
ctgcgagtca gcgcccatcc cccgagcagc cccgagctct ggcctctgcg tccatcatca    780
ggtgggctcg gcctgcgccc ttagctaccc cttcagagac aggctcagcc cacacccca     840 gctgcccctg cagagacagg ctggctctgg gagtcagctt ctggctgatg aacagtggat    900
gtggctcttg cggcacagag cggggtcgca gaatgctgta cgtggcgtgc atttgactca    960
gccctccccc agctcacagt tccctcttg tttctgctca gttttatgg cacaggcctc      1020 atcgcgggcc acggcttcac cagccctgaa cgcaccccg gggtcttcat cctcttcgat     1080
gaggaccgct tcgggttcgt ctggctggag ctgaaatcct tcagcctgta cagccgggtc    1140
caggccacct tccggaacgc agatgcgccg tccccacagg ccttcgatga gatgctcaag    1200
aacattcagt ccctcacctc ctgaccggcc acatccttgc cgccacatcc cgggtggctc    1260
tggggctctg aactctgacc tgtgaataga agcagcatgc actttgggaaa tccgcctttt   1320 tgaccagaac gcacacctcg tcggggggcc cagtccagcc acccccagc actttatgta     1380 gagagtgtga catagacctg catatttgtc agtgccatga tggaagaagc tgagcatgtc    1440
ttaccaaaaa cagagagaac gagcctgaat acagcagatg taggggacag ccgtgggacc    1500
gcgtgagaat tgaagcggtg gggttcccgc accctgggct ggctggtggt tttctcggga   1560
agcaggaccc tcctgactgg tgctcttcct gtgagcggat agagtgatag actgggtcgt    1620
gtgtgagacg catgtgctcc accccactcc ttttggggga agccaggcaa cagtggcctc    1680
tgggaggggg tcaggaagag gcgaacagct caggcagcgc aggtgtgatg ggcacagtac    1740
gcagagcaag ctcgggaagt tggtaggatc tcaggcttgg ggccgggact ctggagtgaa    1800
tccccatttc tctaccggct tgcttggagt ttggacagaa gcattcacc tctgatctca     1860 gcttccccac ctgtggagtg ggtttagtga cctgagtcac tagggaatgt cacctgaatg    1920
cacagcccag cccatgcacc tgccccagcc cctccagctt tggagccaag gccatcgttc    1980
cagccacttg actgtcctcg acggcctgtt ccagacaggg cgtttgtttt gtccatgcct    2040
tcctccctgc acgcacacgg cgtcaaaacc aagctgccgg ccactgtctc cagaacgcaa    2100
ggctccaggc ccgtgtgtct gaagcagtga gtggtccaca caggtgccag gagtgcccat    2160
atgagatgac gaggaaaccc ctttgcaggt gaggggacag ctttctagaa aagccacacc    2220
tgcatctggg gacacacttt ggaaagtggg accctccagc ctggagaccc catggactga    2280
tgcctccact gctgtgtgcc ccatgttgtg ttaacacctg cgtgtgggga ccccatctga    2340
ggtcttggct gaggttggca tctcctgaag aacagagagc acggtgtcca gagctggccc    2400
ttcccccagc ccacagccag ctccgtgccc gagtgggcgt cccagcgag ccttccctct     2460 ctgccgcttg tccttgtgtc tgggctgctc caagtccttg tgctgggcac cctggacacg    2520
tcctgctggt gagggacctc gggaaggtga cagtctgtgt gccttggtgt ggagaccaac    2580
ctgaggatgt cctgggaaat gttttcctga tgaatttctc cttgactggc ctttaaagaa    2640
cataagaatt cccattgccc agcctcagtg catttggcaa atgcttactt tgcttcccag    2700
agtcagagaa ttggcaaagg ttcctaaatg gtaatctggc cggcctggga gaaagactca    2760
```

| | | | | |
|---|---|---|---|---|
| cgagaaaagc | cagtggagaa | agcgcccttc | cagggcggca | gcagcgggag ccacgcagac | 2820 |
| cccgaggcgc | acctgctggc | tcttgtgtgt | ggccccagtt | tctagcggct tttgcagcat | 2880 |
| tagcctacaa | gctttgtcac | tccctgccct | ctgtggtggt | cactgttttt ctctcttgcc | 2940 |
| aaatgaggca | gtctctgagt | gacggtgact | gtggccttga | agcctggagg actgttgggc | 3000 |
| atgtagactg | gcaccttgaa | gattcaccat | tgtttaaata | aaatcaagca aatgcttttt | 3060 |
| taccaagagc | ccgagcctcg | ctctaaggga | cgcagtccta | gaggcgtgcc ctttgggct | 3120 |
| tgaagagcac | actgtgggac | gcacgtgctt | ctgattaaag | gaatctcaga tctc | 3174 |

```
<210> SEQ ID NO 12
<211> LENGTH: 1767
<212> TYPE: DNA
<213> ORGANISM: Homo sapiens

<400> SEQUENCE: 12
```

| | | | | | |
|---|---|---|---|---|---|
| cgcgtccgcg | tgcgcgcctc | cgcggtggtg | acgggcatgg | cggtgtgtgc tcggctctgc | 60 |
| ggcgtgggcc | ccgcgcgtgg | gtgccgccgc | cgccagcagc | gccgcggccc ggccgagact | 120 |
| gcggcggcgg | acagtgaggc | ggacacggac | cccgaggagg | agcgcatcga ggcggggccg | 180 |
| gcgcgttgct | ctctgctgga | gctcccgcct | gagctgctcg | tggagatctt cgcgtcgctg | 240 |
| cccggcaccg | acctgcccag | cctggctcag | gtctgcagca | ggttccgccg aatcttgcac | 300 |
| acggacacca | tctggagacg | cgctgccgc | gaggagtatg | gcgtttgtga gaacctgcgg | 360 |
| aagctggaga | tcacaggtgt | gtcttgccgg | gacgtctatg | caaaactgct tcaccgatac | 420 |
| agacacattt | tggggctgtg | gcagccagat | atcgggccgt | acggaggatt gctgaacgtc | 480 |
| gtggtggacg | gactgttcat | cattggctgg | atgtacctgc | cacctcatga cccccacgtg | 540 |
| ggagacccca | tgcggttcaa | gccactgttt | agaatccatc | tgatggagag gaagtcggct | 600 |
| acagtggagt | gtatgtacgg | ccacaaaggg | ccccacaacg | ccacatcca gattgtgaag | 660 |
| agggacgagt | tctccaccaa | gtgtaaccag | acagatcacc | acaggatgtc cggtgggagg | 720 |
| caggaggagt | ttcggacgtg | gctgaaggag | gagtgggggcc | gcacgctgga agacatcttc | 780 |
| cacgagcaca | tgcaggagct | gattctgatg | aagttcatct | acaccagtca gtacgacaac | 840 |
| tgcctgacct | accgacggat | ctacctcccg | cccagccacc | ctgacgacct catcaagccc | 900 |
| ggcctcttca | agggcaccta | tggcagccac | gggctggaga | ttgtgatgct cagcttccac | 960 |
| ggctcacgcg | cctggggcac | caagatcacg | ggcgacccca | acatcccgc gggacagcag | 1020 |
| actgtagaga | ttgacctgca | gcgccgcatc | cagctgccgg | acgtggagaa cctccgaaac | 1080 |
| ttcaacgagc | tctccaggat | tgtcctggag | gtccgggagc | aggtgcggca ggagcaggag | 1140 |
| gccggcgagg | gcgccgcgcc | acccgggag | ccttcagcca | aggccgctga tgggccacct | 1200 |
| gctaaggacg | gcaaagagcc | tggaggtgga | gccgaggcag | ctgagcagtc ggcctcgtct | 1260 |
| gggcaggggc | agccgtttgt | gcttcctgtg | ggtgtcagct | cgaggaacga ggattacccc | 1320 |
| cgcacttgcc | gcctatgttt | ctatggcaca | ggcctcatcg | ctggccacgg ctttaccagc | 1380 |
| cctgagcgca | ccccggagt | cttcgtcctg | tttgatgagg | accgctttgg atttctgtgg | 1440 |
| ctggaattga | agtccttcag | cttgtacagc | cgagtccagg | ccaccttcca gaacgccgcc | 1500 |
| gcgccgtcgc | cgcaggcctt | tgacgagatg | ctcaggaaca | tccagtctct cacctcctga | 1560 |
| cctccgcatc | gtgggcggag | aggctgcacc | ggggcccggg | tggggaagc atgcacttta | 1620 |
| gaaatgaacg | cacacctcct | cactgggtc | ccggtcgccc | cgggacgctt cttgtatagt | 1680 |

-continued

```
gtgtaacata ctcttgtaca tttgacttgt tggtagctat gaaggagaac gctaagcatg    1740
gtgagaaaat aaacggagtt gagccag                                        1767
```

<210> SEQ ID NO 13
<211> LENGTH: 507
<212> TYPE: PRT
<213> ORGANISM: Homo sapiens

<400> SEQUENCE: 13

```
Met Ala Val Cys Ala Arg Leu Cys Gly Val Gly Pro Ala Arg Gly Cys
1               5                   10                  15

Arg Arg Arg Gln Gln Arg Gly Pro Ala Glu Thr Ala Ala Ala Asp
            20                  25                  30

Ser Glu Ala Asp Thr Asp Pro Glu Glu Arg Ile Glu Ala Gly Pro
        35                  40                  45

Ala Arg Cys Ser Leu Leu Glu Leu Pro Pro Glu Leu Leu Val Glu Ile
    50                  55                  60

Phe Ala Ser Leu Pro Gly Thr Asp Leu Pro Ser Leu Ala Gln Val Cys
65                  70                  75                  80

Ser Arg Phe Arg Arg Ile Leu His Thr Asp Thr Ile Trp Arg Arg
                85                  90                  95

Cys Arg Glu Glu Tyr Gly Val Cys Glu Asn Leu Arg Lys Leu Glu Ile
            100                 105                 110

Thr Gly Val Ser Cys Arg Asp Val Tyr Ala Lys Leu Leu His Arg Tyr
        115                 120                 125

Arg His Ile Leu Gly Leu Trp Gln Pro Asp Ile Gly Pro Tyr Gly Gly
    130                 135                 140

Leu Leu Asn Val Val Asp Gly Leu Phe Ile Ile Gly Trp Met Tyr
145                 150                 155                 160

Leu Pro Pro His Asp Pro His Val Gly Asp Pro Met Arg Phe Lys Pro
                165                 170                 175

Leu Phe Arg Ile His Leu Met Glu Arg Lys Ser Ala Thr Val Glu Cys
            180                 185                 190

Met Tyr Gly His Lys Gly Pro His Asn Gly His Ile Gln Ile Val Lys
        195                 200                 205

Arg Asp Glu Phe Ser Thr Lys Cys Asn Gln Thr Asp His His Arg Met
    210                 215                 220

Ser Gly Gly Arg Gln Glu Glu Phe Arg Thr Trp Leu Lys Glu Glu Trp
225                 230                 235                 240

Gly Arg Thr Leu Glu Asp Ile Phe His Glu His Met Gln Glu Leu Ile
                245                 250                 255

Leu Met Lys Phe Ile Tyr Thr Ser Gln Tyr Asp Asn Cys Leu Thr Tyr
            260                 265                 270

Arg Arg Ile Tyr Leu Pro Pro Ser His Pro Asp Asp Leu Ile Lys Pro
        275                 280                 285

Gly Leu Phe Lys Gly Thr Tyr Gly Ser His Gly Leu Glu Ile Val Met
    290                 295                 300

Leu Ser Phe His Gly Ser Arg Ala Trp Gly Thr Lys Ile Thr Gly Asp
305                 310                 315                 320

Pro Asn Ile Pro Ala Gly Gln Gln Thr Val Glu Ile Asp Leu Gln Arg
                325                 330                 335

Arg Ile Gln Leu Pro Asp Val Glu Asn Leu Arg Asn Phe Asn Glu Leu
            340                 345                 350

Ser Arg Ile Val Leu Glu Val Arg Glu Gln Val Arg Gln Glu Gln Glu
```

```
                     355                   360                   365
Ala Gly Glu Gly Ala Ala Pro Pro Arg Glu Pro Ser Ala Lys Ala Ala
    370                 375                 380

Asp Gly Pro Pro Ala Lys Asp Gly Lys Glu Pro Gly Gly Gly Ala Glu
385                 390                 395                 400

Ala Ala Glu Gln Ser Ala Ser Ser Gly Gln Gly Gln Pro Phe Val Leu
                405                 410                 415

Pro Val Gly Val Ser Ser Arg Asn Glu Asp Tyr Pro Arg Thr Cys Arg
            420                 425                 430

Leu Cys Phe Tyr Gly Thr Gly Leu Ile Ala Gly His Gly Phe Thr Ser
        435                 440                 445

Pro Glu Arg Thr Pro Gly Val Phe Val Leu Phe Asp Glu Asp Arg Phe
    450                 455                 460

Gly Phe Leu Trp Leu Glu Leu Lys Ser Phe Ser Leu Tyr Ser Arg Val
465                 470                 475                 480

Gln Ala Thr Phe Gln Asn Ala Ala Pro Ser Pro Gln Ala Phe Asp
                485                 490                 495

Glu Met Leu Arg Asn Ile Gln Ser Leu Thr Ser
    500                 505

<210> SEQ ID NO 14
<211> LENGTH: 5106
<212> TYPE: DNA
<213> ORGANISM: Homo sapiens

<400> SEQUENCE: 14
ggcatggcgg tgtgtgctcg cctttgcggc gtgggcccgt cgcgcggatg tcggcgccgc      60
cagcagcgcc ggggcccggc cgagacggcg gcggccgaca gcgagccgga cacagacccc     120
gaggaggagc gcatcgaggc tagcgccggg gtcgggggcg gcttgtgcgc gggcccctcg     180
ccgccgcccc cgcgctgctc gctgctggag ctgccgcccg agctgctggt ggagatcttc     240
gcgtcgctgc cgggcacgga cctacccagc ttggcccagg tctgcacgaa gttccggcgc     300
atcctccaca ccgacaccat ctggaggagg cgttgccgtg aggagtatgg tgtttgcgaa     360
aacttgcgga agctggagat cacaggcgtg tcttgtcggg acgtctatgc gaagctgctt     420
caccgatata gacacatttt tggattgtgg cagccagata tcgggccata cggaggactg     480
ctgaacgtgg tggtggacgg cctgttcatc atcgggtgga tgtacctgcc tccccatgac     540
ccccacgtcg atgaccctat gagattcaag cctctgttca ggatccacct gatggagagg     600
aaggctgcca cagtggagtg catgtacggc cacaaagggc ccaccacggg ccacatccag     660
attgtgaaga aggatgagtt ctccaccaag tgcaaccaga cggaccacca caggatgtcc     720
ggcgggaggc aggaggagtt tcggacgtgg ctgagggagg aatgggggcg cacgctggag     780
gacatcttcc acgagcacat gcaggagctc atcctgatga agttcatcta caccagtcag     840
tacgacaact gcctgaccta ccgccgcatc tacctgccgc ccagccgccc cgacgacctc     900
atcaagcctg gcctcttcaa aggtacctat ggcagccacg gcctggagat tgtgatgctc     960
agcttccacg gccggcgtgc cagggcacc aagatcacgg gcgaccccaa catccccgct    1020
gggcagcaga cagtggagat cgacctgagg catcggatcc agctgccgga cctcgagaac    1080
cagcgcaact tcaatgagct ctcccgcatc gtcctggagg tgcgcgagag ggtgcgccag    1140
gagcagcagg aaggcgggca cgaggcgggc gagggtcgtg gccggcaggg cccccgggag    1200
tcccagccaa gccctgccca gcccagggca gaggcgccca gcaagggccc agatgggaca    1260
```

```
cctggtgagg atggtggcga gcctggggat gccgtagctg cggccgagca gcctgcccag   1320
tgtgggcagg ggcagccgtt cgtgctgccc gtgggcgtga gctccaggaa tgaggactac   1380
ccccgaacct gcaggatgtg ttttatggc acaggcctca tcgcgggcca cggcttcacc     1440
agccctgaac gcacccccgg ggtcttcatc ctcttcgatg aggaccgctt cgggttcgtc   1500
tggctggagc tgaaatcctt cagcctgtac agccgggtcc aggccacctt ccggaacgca   1560
gatgcgccgt ccccacaggc cttcgatgag atgctcaaga acattcagtc cctcacctcc   1620
tgaccggcca catccttgcc gccacatccc gggtggctct ggggctctga actctgacct   1680
gtgaatagaa gcagcatgca cttttggaaat ccggccttt gaccagaacg cacacctcgt  1740
cgggggcccc agtccagcca ccccccagca ctttatgtag agagtgtgac atagacctgc   1800
atatttgtca gtgccatgat ggaagaagct gagcatgtct taccaaaaac agagagaacg   1860
agcctgaata cagcagatgt aggggacagc cgtgggaccg cgtgagaatt gaagcggtgg   1920
ggttcccgca ccctgggctg gctggtggtt ttctcgggaa gcaggaccct cctgactggt   1980
gctcttcctg tgagcggata gagtgataga ctgggtcgtg tgtgagacgc atgtgctcca   2040
ccccactcct tttgggggaa gccaggcaac agtggcctct ggggggggt caggaagagg     2100
cgaacagctc aggcagcgca ggtgtgatgg gcacagtacg cagagcaagc tcgggaagtt   2160
ggtaggatct caggcttggg gccgggactc tggagtgaat ccccatttct ctaccggctt   2220
gcttggagtt tggacagaag catttcacct ctgatctcag cttccccacc tgtggagtgg   2280
gtttagtgac ctgagtcact agggaatgtc acctgaatgc acagcccagc ccatgcacct   2340
gccccagccc ctccagcttt ggagccaagg ccatcgttcc agccacttga ctgtcctcga   2400
cggcctgttc cagacagggc gtttgttttg tccatgcctt cctccctgca cgcacacggc   2460
gtcaaaacca agctgccggc cactgtctcc agaacgcaag gctccaggcc cgtgtgtctg   2520
aagcagtgag tggtccacac aggtgccagg agtgcccata tgagatgacg aggaaacccc   2580
tttgcaggtg aggggacagc tttctagaaa agccacacct gcatctgggg acacactttg   2640
gaaagtggga ccctccagcc tggagacccc atggactgat gcctccactg ctgtgtgccc   2700
catgttgtgt taacacctgc gtgtggggac cccatctgag gtcttggctg aggttggcat   2760
ctcctgaaga acagagagca cggtgtccag agctggccct tcccccagcc cacagccagc   2820
tccgtgcccg agtgggcgtc cccagcgagc cttccctctc tgccgcttgt ccttgtgtct   2880
gggctgctcc aagtccttgt gctgggcacc ctggacacgt cctgctggtg agggacctcg   2940
ggaaggtgac agtctgtgtg ccttggtgtg agaccaacc tgaggatgtc ctgggaaatg     3000
ttttcctgat gaatttctcc ttgactggcc tttaaagaac ataagaattc ccattgccca   3060
gcctcagtgc atttggcaaa tgcttacttt gcttcccaga gtcagagaat tggcaaaggt   3120
tcctaaatgg taatctggcc ggcctgggag aaagactcac gagaaaagcc agtggagaaa   3180
gcgcccttcc agggcggcag cagcgggagc cacgcagacc ccgaggcgca cctgctggct   3240
cttgtgtgtg gccccagttt ctagcggctt ttgcagcatt agcctacaag ctttgtcact   3300
ccctgccctc tgtggtggtc actgttttc tctcttgcca aatgaggcag tctctgagtg     3360
acggtgactg tggccttgaa gcctggagga ctgttgggca tgtagactgg caccttgaag   3420
attcaccatt gtttaaataa aatcaagcaa atgcttttt accaagagcc cgagcctcgc    3480
tctaagggac gcagtcctag aggcgtgccc tttgggcctt gaagagcaca ctgtgggacg   3540
cacgtgcttc tgattaaagg aatctcgat ctcaattacg cttccagtgt ttgggtatag    3600
aaatagcttc cacccatcat gtctcagcca tgggctgttg gtcagttcat gtggctcctg   3660
```

| | |
|---|---|
| gttctggtgt gtatgttggg ggcggggggtc tctccatggt ggtgacctgc agtgatgcca | 3720 |
| ggcagggcca gagccacaca gccaggaaag ggaggccttt ttggccgcac agccagtccc | 3780 |
| ttcagtcgtg actacaggtc ttgttttttc cgctccgatg tgtccttagc cagttcttgg | 3840 |
| ctccggttct gtagggacag gcactgaatc tgcgcgcctc aaaacagcag cttcccttcc | 3900 |
| gggggagggc atccaccctc tcaggggatc ctgcaggtgg cccatttcct gcaggtgaga | 3960 |
| actcggaagg gctgatgtcg tcatcagagg cctaagggca gctgagagtt ggataaaacc | 4020 |
| gtttccaagg aggaggctga gtaacccagt tcaggacagc caagcgcatt aggcttgatt | 4080 |
| ggggaaggtg gcaggtggag ttgggaggtt gggactctcc atcttttgca ccacggatgc | 4140 |
| ctttctgtcg ctgtctcact ctggggcagg atcaagtctg ctctctggag tggggctgcc | 4200 |
| tgcagtgcag ctctgcacac ctgaacgtgt tctttgtcac ttgtttggaa atgatgtgat | 4260 |
| tgaagatttc agagaggtca ttggaggctt ttctgtgccg gcactgaatg ttcatttgca | 4320 |
| tgaggaagtt gcaaacgact tctgcaggct gagattcaag gcaggtggta ttggggtccc | 4380 |
| tcagcccacc tgggccgtga cctcaagtgt ccactgctga gtgtgagtgg ctttgcaggc | 4440 |
| ctggtggtgg gagagcctca ggctccctcc ttcttcgttc ctgaccatgc cctgggcccc | 4500 |
| ttcagtctgc ctgcggctct gtggcatccc tgccctgaca ctgggcacct gtgcccctag | 4560 |
| caagcccacc tggcacacga ggagggaggg gtgggtggcc atgtccttcc tctagccaca | 4620 |
| tgccctgctg gccgctccat tctgagcttt gtgcagaacc gggtctgagc tggagatttt | 4680 |
| tctctgagaa cctgcagttg tgctgcagcc gcacgcaagg gccttcagc cgctggctct | 4740 |
| ggcttccctg actcctcagg gcgtgttcac ccccaggctt tctcacctgc acacggttag | 4800 |
| gccattttca gtgctcgtgg gcagtcacgg acagcagcag aaaactcctca gccccttttgt | 4860 |
| tacttcagaa cgcctgccca catgcatctt ctgagctcgt gttgtcctca tggccgtggg | 4920 |
| gtcttgggtg cgaacaggag atgctgagct gtggtccacc gtccaaggtg ctgcagaaag | 4980 |
| cagctaggct ctttttaggat gtttctattc tggttgctgc cttcgtggtg taacttttaa | 5040 |
| gaacacttac gggaatgtgc tcatagaacc atcacctgtc ctgagaataa aactcctgga | 5100 |
| atcatg | 5106 |

<210> SEQ ID NO 15
<211> LENGTH: 5193
<212> TYPE: DNA
<213> ORGANISM: Homo sapiens

<400> SEQUENCE: 15

| | |
|---|---|
| ggcatggcgg tgtgtgctcg cctttgcggc gtgggcccgt cgcgcggatg tcggcgccgc | 60 |
| cagcagcgcc ggggcccggc cgagacggcg gcggccgaca gcgagccgga cacagacccc | 120 |
| gaggaggagc gcatcgaggc tagcgccggg gtcgggggcg gcttgtgcgc gggcccctcg | 180 |
| ccgccgcccc cgcgctgctc gctgctggag ctgccgcccg agctgctggt ggagatcttc | 240 |
| gcgtcgctgc cgggcacgga cctacccagc ttggcccagg tctgcacgaa gttccggcgc | 300 |
| atcctccaca ccgacaccat ctggaggagg cgttgccgtg aggagtatgg tgtttgcgaa | 360 |
| aacttgcgga agctggagat cacaggcgtg tcttgtcggg acgtctatgc gaagcgtata | 420 |
| aaccctcgcg tgaagtcggg acgttttgtg aaaattctcc ctgattatga gcacatggcg | 480 |
| tacagagacg tttacacctg cctgcttcac cgatatagac acattttggg attgtggcag | 540 |
| ccagatatcg ggccatacgg aggactgctg aacgtggtgg tggacggcct gttcatcatc | 600 |

-continued

```
gggtggatgt acctgcctcc ccatgacccc cacgtcgatg accctatgag attcaagcct    660
ctgttcagga tccacctgat ggagaggaag gctgccacag tggagtgcat gtacggccac    720
aaagggcccc accacggcca catccagatt gtgaagaagg atgagttctc caccaagtgc    780
aaccagacgg accaccacag gatgtccggc gggaggcagg aggagtttcg gacgtggctg    840
agggaggaat gggggcgcac gctggaggac atcttccacg agcacatgca ggagctcatc    900
ctgatgaagt tcatctacac cagtcagtac gacaactgcc tgacctaccg ccgcatctac    960
ctgccgccca gccgcccga cgacctcatc aagcctggcc tcttcaaagg tacctatggc   1020
agccacggcc tggagattgt gatgctcagc ttccacggcc ggcgtgccag ggcaccaag    1080
atcacgggcg accccaacat ccccgctggg cagcagacag tggagatcga cctgaggcat   1140
cggatccagc tgcccgacct cgagaaccag cgcaacttca atgagctctc ccgcatcgtc   1200
ctggaggtgc gcgagagggt gcgccaggag cagcaggaag gcgggcacga ggcgggcgag   1260
ggtcgtggcc gcagggccc ccgggagtcc cagccaagcc ctgcccagcc cagggcagag   1320
gcgcccagca agggcccaga tgggacacct ggtgaggatg tggcgagcc tggggatgcc   1380
gtagctgcgg ccgagcagcc tgcccagtgt gggcagggggc agccgttcgt gctgcccgtg   1440
ggcgtgagct ccaggaatga ggactacccc cgaacctgca ggatgtgttt ttatggcaca   1500
ggcctcatcg cgggccacgg cttcaccagc cctgaacgca ccccgggggt cttcatcctc   1560
ttcgatgagg accgcttcgg gttcgtctgg ctggagctga atccttcag cctgtacagc   1620
cgggtccagg ccaccttccg gaacgcagat gcgccgtccc cacaggcctt cgatgagatg   1680
ctcaagaaca ttcagtccct cacctcctga ccggccacat ccttgccgcc acatcccggg   1740
tggctctggg gctctgaact ctgacctgtg aatagaagca gcatgcactt tggaaatccg   1800
gccttttgac cagaacgcac acctcgtcgg ggggcccagt ccagccaccc cccagcactt   1860
tatgtagaga gtgtgacata gacctgcata tttgtcagtg ccatgatgga agaagctgag   1920
catgtcttac caaaaacaga gagaacgagc ctgaatacag cagatgtagg ggacagccgt   1980
gggaccgcgt gagaattgaa gcggtggggt tcccgcaccc tgggctggct ggtggttttc   2040
tcgggaagca ggaccctcct gactggtgct cttcctgtga gcggatagag tgatagactg   2100
ggtcgtgtgt gagacgcatg tgctccaccc cactccttttt gggggaagcc aggcaacagt   2160
ggcctctggg aggggtcag gaagaggcga acagctcagg cagcgcaggt gtgatgggca   2220
cagtacgcag agcaagctcg ggaagttggt aggatctcag gcttgggcc gggactctgg   2280
agtgaatccc catttctcta ccggcttgct tggagtttgg acagaagcat ttcacctctg   2340
atctcagctt ccccacctgt ggagtgggtt tagtgacctg agtcactagg gaatgtcacc   2400
tgaatgcaca gcccagccca tgcacctgcc ccagcccctc cagcttttgga gccaaggcca   2460
tcgttccagc cacttgactg tcctcgacgg cctgttccag acagggcgtt tgttttgtcc   2520
atgccttcct ccctgcacgc acacggcgtc aaaaccaagc tgccggccac tgtctccaga   2580
acgcaaggct ccaggcccgt gtgtctgaag cagtgagtgg tccacacagg tgccaggagt   2640
gcccatatga gatgacgagg aaacccctttt gcaggtgagg ggacagcttt ctagaaaagc   2700
cacacctgca tctggggaca cactttggaa agtgggaccc tccagcctgg agaccccatg   2760
gactgatgcc tccactgctg tgtgcccat gttgtgttaa cacctgcgtg tggggacccc   2820
atctgaggtc ttggctgagg ttggcatctc ctgaagaaca gagagcacgg tgtccagagc   2880
tggccctccc cccagcccac agccagctcc gtgcccgagt gggcgtcccc agcgagcctt   2940
ccctctctgc cgcttgtcct tgtgtctggg ctgctccaag tccttgtgct gggcaccctg   3000
```

```
gacacgtcct gctggtgagg gacctcggga aggtgacagt ctgtgtgcct tggtgtggag    3060
accaacctga ggatgtcctg ggaaatgttt tcctgatgaa tttctccttg actggccttt    3120
aaagaacata agaattccca ttgcccagcc tcagtgcatt tggcaaatgc ttactttgct    3180
tcccagagtc agagaattgg caaaggttcc taaatggtaa tctggccggc tgggagaaa     3240 gactcacgag aaaagccagt ggagaaagcg cccttccagg gcggcagcag cgggagccac    3300
gcagaccccg aggcgcacct gctggctctt gtgtgtggcc ccagtttcta gcggcttttg    3360
cagcattagc ctacaagctt tgtcactccc tgccctctgt ggtggtcact gtttttctct    3420
cttgccaaat gaggcagtct ctgagtgacg gtgactgtgg ccttgaagcc tggaggactg    3480
ttgggcatgt agactggcac cttgaagatt caccattgtt taaataaaat caagcaaatg    3540 ctttttttacc aagagcccga gcctcgctct aagggacgca gtcctagagg cgtgcccttt    3600
ggggcttgaa gagcacactg tgggacgcac gtgcttctga ttaaaggaat ctcagatctc    3660
aattacgctt ccagtgtttg ggtatagaaa tagcttccac ccatcatgtc tcagccatgg    3720
gctgttggtc agttcatgtg gctcctggtt ctggtgtgta tgttggggc ggggtctct      3780 ccatggtggt gacctgcagt gatgccaggc agggccagag ccacacagcc aggaaaggga    3840
ggcctttttg ccgcacagc cagtcccttc agtcgtgact acaggtcttg ttttttccgc     3900
tccgatgtgt ccttagccag ttcttggctc cggttctgta gggacaggca ctgaatctgc    3960
gcgcctcaaa acagcagctt cccttccggg ggagggcatc caccctctca ggggatcctg    4020
caggtggccc atttcctgca ggtgagaact cggaagggct gatgtcgtca tcagaggcct    4080
aagggcagct gagagttgga taaaaccgtt tccaaggagg aggctgagta acccagttca    4140
ggacagccaa gcgcattagg cttgattggg aaggtggca ggtggagttg ggaggttggg     4200
actctccatc ttttgcacca cggatgcctt tctgtcgctg tctcactctg gggcaggatc    4260
aagtctgctc tctggagtgg ggctgcctgc agtgcagctc tgcacacctg aacgtgttct    4320
ttgtcacttg tttggaaatg atgtgattga agatttcaga gaggtcattg gaggcttttc    4380
tgtgccggca ctgaatgttc atttgcatga ggaagttgca aacgacttct gcaggctgag    4440
attcaaggca ggtggtattg gggtccctca gcccacctgg gccgtgacct caagtgtcca    4500
ctgctgagtg tgagtggctt tgcaggcctg gtggtgggag agcctcaggc tccctccttc    4560
ttcgttcctg accatgccct gggccccttc agtctgcctg cggctctgtg gcatccctgc    4620
cctgacactg ggcacctgtg cccctagcaa gcccacctgg cacacgagga gggaggggtg    4680
ggtggccatg tccttcctct agccacatgc cctgctggcc gctccattct gagctttgtg    4740
cagaaccggg tctgagctgg agatttttct ctgagaacct gcagttgtgc tgcagccgca    4800
cgcaagggcc cttcagccgc tggctctggc ttccctgact cctcagggcg tgttcacccc    4860 caggcttttct cacctgcaca cggttaggcc attttcagtg ctcgtgggca gtcacggaca    4920
gcagcagaaa ctcctcagcc cctttgttac ttcagaacgc ctgcccacat gcatcttctg    4980
agctcgtgtt gtcctcatgg ccgtggggtc ttgggtgcga acaggagatg ctgagctgtg    5040
gtccaccgtc caaggtgctg cagaaagcag ctaggctctt ttaggatgtt tctattctgg    5100 ttgctgccttt cgtggtgtaa ctttttaagaa cacttacggg aatgtgctca tagaaccatc    5160
acctgtcctg agaataaaac tcctggaatc atg                                 5193

<210> SEQ ID NO 16
<211> LENGTH: 5924
<212> TYPE: DNA
```

<213> ORGANISM: Homo sapiens

<400> SEQUENCE: 16

```
ggcatggcgg tgtgtgctcg cctttgcggc gtgggcccgt cgcgcggatg tcggcgccgc      60
cagcagcgcc ggggcccggc cgagacggcg gcggccgaca gcgagccgga cacagacccc    120
gaggaggagc gcatcgaggc tagcgccggg gtcgggggcg gcttgtgcgc gggcccctcg    180
ccgccgcccc cgcgctgctc gctgctggag ctgccgcccg agctgctggt ggagatcttc    240
gcgtcgctgc cgggcacgga cctacccagc ttggcccagg tctgcacgaa gttccggcgc    300
atcctccaca ccgacaccat ctggaggagg cgttgccgtg aggagtatgg tgtttgcgaa    360
aacttgcgga agctggagat cacaggcgtg tcttgtcggg acgtctatgc gaagctgctt    420
caccgatata gacacatttt gggattgtgg cagccagata tcgggccata cggaggactg    480
ctgaacgtgg tggtggacgg cctgttcatc atcgggtgga tgtacctgcc tccccatgac    540
ccccacgtcg atgaccctat gagattcaag cctctgttca ggatccacct gatggagagg    600
aaggctgcca cagtggagtg catgtacggc cacaaagggc cccaccacgg ccacatccag    660
attgtgaaga aggatgagtt ctccaccaag tgcaaccaga cggaccacca caggatgtcc    720
ggcgggaggc aggaggagtt tcggacgtgg ctgagggagg aatgggggcg cacgctggag    780
gacatcttcc acgagcacat gcaggagctc atcctgatga agttcatcta caccagtcag    840
tacgacaact gcctgaccta ccgccgcatc tacctgccgc ccagccgccc cgacgacctc    900
atcaagcctg gcctcttcaa aggtacctat ggcagccacg gcctggagat tgtgatgctc    960
agcttccacg gccggcgtgc cagggcacc aagatcacgg gcgaccccaa catccccgct   1020
gggcagcaga cagtggagat cgacctgagg catcggatcc agctgcccga cctcgagaac   1080
cagcgcaact tcaatgagct ctcccgcatc gtcctggagg tgcgcgagag ggtgcgccag   1140
gagcagcagg aaggcgggca cgaggcgggc gagggtcgtg gccggcaggg ccccggggag   1200
tcccagccaa gccctgccca gcccagggca gaggcgccca gcaagggccc agatgggaca   1260
cctggtgagg atggtggcga gcctggggat gccgtagctg cggccgagca gcctgcccag   1320
tgtgggcagg ggcagccgtt cgtgctgccc gtgggcgtga gctccaggaa tgaggactac   1380
ccccgaacct gcaggatgtg tttttatggc acaggcctca tcgcgggcca cggcttcacc   1440
agccctgaac gcaccccgg ggtcttcatc ctcttcgatg aggaccgctt cgggttcgtc   1500
tggctggagc tgaaatcctt cagcctgtac agccgggtcc aggccacctt ccggaacgca   1560
gatgcgccgt cccacaggc cttcgatgag atgctcaaga acattcagtc cctcacctcc   1620
tgaccggcca catccttgcc gccacatccc gggtggctct gggctctga actctgacct   1680
gtgaatagaa gcagcatgca cttttggaaat ccggcctttt gaccagaacg cacacctcgt   1740
cgggggccc agtccagcca ccccccagca cttatgtag agagtgtgac atagacctgc   1800
atatttgtca gtgccatgat ggaagaagct gagcatgtct taccaaaaac agagagaacg   1860
agcctgaata cagcagatgt agggacagc cgtgggaccg cgtgagaatt gaagcggtgg   1920
ggttcccgca ccctgggctg gctggtggtt ttctcgggaa gcaggaccct cctgactggt   1980
gctcttcctg tgagcggata gagtgataga ctgggtcgtg tgtgagacgc atgtgctcca   2040
ccccactcct tttgggggaa gccaggcaac agtggcctct ggagggggt caggaagagg   2100
cgaacagctc aggcagcgca ggtgtgatgg gcacagtacg cagagcaagc tcgggaagtt   2160
ggtaggatct caggcttggg gccgggactc tggagtgaat ccccatttct ctaccggctt   2220
gcttggagtt tggacagaag catttcacct ctgatctcag cttccccacc tgtggagtgg   2280
```

```
gtttagtgac ctgagtcact agggaatgtc acctgaatgc acagcccagc ccatgcacct    2340
gccccagccc ctccagcttt ggagccaagg ccatcgttcc agccacttga ctgtcctcga    2400
cggcctgttc cagacagggc gtttgttttg tccatgcctt cctccctgca cgcacacggc    2460
gtcaaaacca agctgccggc cactgtctcc agaacgcaag gctccaggcc cgtgtgtctg    2520
aagcagtgag tggtccacac aggtgccagg agtgcccata tgagatgacg aggaaacccc    2580
tttgcaggtg aggggacagc tttctagaaa agccacacct gcatctgggg acacactttg    2640
gaaagtggga ccctccagcc tggagacccc atggactgat gcctccactg ctgtgtgccc    2700
catgttgtgt taacacctgc gtgtggggac cccatctgag gtcttggctg aggttggcat    2760
ctcctgaaga acagagagca cggtgtccag agctggccct tcccccagcc cacagccagc    2820
tccgtgcccg agtgggcgtc cccagcgagc cttccctctc tgccgcttgt ccttgtgtct    2880
gggctgctcc aagtccttgt gctgggcacc ctggacacgt cctgctggtg agggacctcg    2940
ggaaggtgac agtctgtgtg ccttggtgtg agaccaacc tgaggatgtc ctgggaaatg    3000
ttttcctgat gaatttctcc ttgactggcc tttaaagaac ataagaattc ccattgccca    3060
gcctcagtgc atttggcaaa tgcttacttt gcttcccaga gtcagagaat tggcaaaggt    3120
tcctaaatgg taatctggcc ggcctgggag aaagactcac gagaaaagcc agtggagaaa    3180
gcgcccttcc agggcggcag cagcgggagc cacgcagacc ccgaggcgca cctgctggct    3240
cttgtgtgtg gccccagttt ctagcggctt ttgcagcatt agcctacaag ctttgtcact    3300
ccctgccctc tgtggtggtc actgttttc tctcttgcca aatgaggcag tctctgagtg    3360
acggtgactg tggccttgaa gcctggagga ctgttgggca tgtagactgg caccttgaag    3420
attcaccatt gtttaaataa aatcaagcaa atgcttttt accaagagcc cgagcctcgc    3480
tctaagggac gcagtcctag aggcgtgccc tttgggctt gaagagcaca ctgtgggacg    3540
cacgtgcttc tgattaaagg aatctcagat ctcaattacg cttccagtgt ttgggtatag    3600
aaatagcttc cacccatcat gtctcagcca tgggctgttg gtcagttcat gtggctcctg    3660
gttctggtgt gtatgttggg ggcggggtc tctccatggt ggtgacctgc agtgatgcca    3720
ggcagggcca gagccacaca gccaggaaag ggaggccttt ttggccgcac agccagtccc    3780
ttcagtcgtg actacaggtc ttgttttttc cgctccgatg tgtccttagc cagttcttgg    3840
ctccggttct gtagggacag gcactgaatc tgcgcgcctc aaaacagcag cttcccttcc    3900
gggggagggc atccaccctc tcaggggatc ctgcaggtgg cccatttcct gcaggtgaga    3960
actcggaagg gctgatgtcg tcatcagagg cctaagggca gctgagagtt ggataaaacc    4020
gtttccaagg aggaggctga gtaacccagt tcaggacagc caagcgcatt aggcttgatt    4080
ggggaaggtg gcaggtggag ttgggaggtt gggactctcc atcttttgca ccacggatgc    4140 cttttctgtcg ctgtctcact ctggggcagg atcaagtctg ctctctggag tggggctgcc    4200
tgcagtgcag ctctgcacac ctgaacgtgt tctttgtcac ttgtttggaa atgatgtgat    4260
tgaagatttc agagaggtca ttggaggctt ttctgtgccg gcactgaatg ttcatttgca    4320
tgaggaagtt gcaaacgact tctgcaggct gagattcaag gcaggtggta ttggggtccc    4380
tcagcccacc tgggccgtga cctcaagtgt ccactgctga gtgtgagtgg ctttgcaggc    4440
ctggtggtgg gagagcctca ggctccctcc ttcttcgttc ctgaccatgc cctgggcccc    4500
ttcagtctgc ctgcggctct gtggcatccc tgccctgaca ctgggcacct gtgcccctag    4560
caagcccacc tggcacacga ggagggaggg gtgggtggcc atgtccttcc tctagccaca    4620
```

```
tgccctgctg gccgctccat tctgagcttt gtgcagaacc gggtctgagc tggagatttt    4680
tctctgagaa cctgcagttg tgctgcagcc gcacgcaagg gcccttcagc cgctggctct    4740
ggcttccctg actcctcagg gcgtgttcac cccaggctt  tctcacctgc acacggttag    4800
gccattttca gtgctcgtgg gcagtcacgg acagcagcag aaactcctca gccccttgt     4860 tacttcagaa cgcctgccca catgcatctt ctgagctcgt gttgtcctca tggccgtggg    4920
gtcttgggtg cgaacaggag atgctgagct gtggtccacc gtccaaggtg ctgcagaaag    4980
cagctaggct cttttaggat gtttctattc tggttgctgc cttcgtggtg taactttaa    5040 gaacacttac gggaatgtgc tcatagaacc atcacctgtc ctgagaataa aactcctgga    5100
atcatgatca agtccagtgt taacgtggcc caacctgtct gtacttctgg ggagagacca    5160
ggaacatcac tggactcctc atccccgtaa ttatttagag aagatgcaag cagcagatag    5220
tctccatgcg gctggtactt tttttgttgt ttttgagac agggtcttgc tctgtcacct     5280
gggctggagt gcagagcggc gatcatggct ccctgaggcc tcaacctact aggctcaagc    5340
tgtctgcccg ccttagcctc ccaagtagct gggaccacag gcacccacca ccaccatgct    5400
tggctaactt gttttgtag agatggagtt ttgccatgtt gctcaggttg gtctcgaact     5460
cccgatctca ggtgatccac ccgcctcggc ctcccaaagt gctgggatta caggcgtgag    5520
cccctgcgcc ccagccttgg ggcctgtctt tgaatgggaa tgagactgtg caaaccgtgg    5580
actaccctgt gtcacccaca gctcagtggc ctgcctgccg gccctcaggg gctgctgacc    5640
gggagaccag ccagagcacg aggggtcag  ggctgtgtgg gttttggcct gattctgcat    5700
ttggttgttt ctgggggcca tgtagcctgc ctgcattagg aaagcgctgt gccatctgat    5760
catgagcacc tctgcacccc ctggtaaggt gaccttgcag caggagctgt gccctgcctg    5820
ggtaggcacc cactaggtag gaccggagca atcctggcag ccgccacctg cacccgtgca    5880
cttgtttctc ctcacagttt caagtaaatc cgtttttgaa ggct                     5924
```

<210> SEQ ID NO 17
<211> LENGTH: 6011
<212> TYPE: DNA
<213> ORGANISM: Homo sapiens

<400> SEQUENCE: 17

```
ggcatggcgg tgtgtgctcg cctttgcggc gtgggcccgt cgcgcggatg tcggcgccgc      60
cagcagcgcc ggggcccggc cgagacggcg gcggccgaca gcgagccgga cacagacccc     120
gaggaggagc gcatcgaggc tagcgccggg gtcgggggcg gcttgtgcgc gggcccctcg     180
ccgccgcccc cgcgctgctc gctgctggag ctgccgcccg agctgctggt ggagatcttc     240
gcgtcgctgc cgggcacgga cctacccagc ttggcccagg tctgcacgaa gttccggcgc     300
atcctccaca ccgacaccat ctggaggagg cgttgccgtg aggagtatgg tgtttgcgaa     360
aacttgcgga agctggagat cacaggcgtg tcttgtcggg acgtctatgc gaagcgtata     420
aaccctcgcg tgaagtcggg acgttttgtg aaaattctcc ctgattatga gcacatggcg     480
tacagagacg tttacacctg cctgcttcac cgatatagac acattttggg attgtggcag     540
ccagatatcg ggccatacgg aggactgctg aacgtggtgg tggacggcct gttcatcatc     600
gggtggatgt acctgcctcc ccatgacccc cacgtcgatg accctatgag attcaagcct     660
ctgttcagga tccacctgat ggagaggaag gctgccacag tggagtgcat gtacggccac     720
aaagggcccc accacggcca catccagatt gtgaagaagg atgagttctc caccaagtgc     780
aaccagacgg accaccacag gatgtccggc gggaggcagg aggagtttcg gacgtggctg     840
```

-continued

```
agggaggaat gggggcgcac gctggaggac atcttccacg agcacatgca ggagctcatc      900
ctgatgaagt tcatctacac cagtcagtac gacaactgcc tgacctaccg ccgcatctac      960
ctgccgccca gccgccccga cgacctcatc aagcctggcc tcttcaaagg tacctatggc     1020
agccacggcc tggagattgt gatgctcagc ttccacggcc ggcgtgccag gggcaccaag     1080
atcacgggcg accccaacat ccccgctggg cagcagacag tggagatcga cctgaggcat     1140
cggatccagc tgcccgacct cgagaaccag cgcaacttca atgagctctc ccgcatcgtc     1200
ctggaggtgc gcgagagggt gcgccaggag cagcaggaag gcgggcacga ggcgggcgag     1260
ggtcgtggcc ggcagggccc ccgggagtcc cagccaagcc ctgcccagcc cagggcagag     1320
gcgcccagca agggcccaga tgggacacct ggtgaggatg gtggcgagcc tggggatgcc     1380
gtagctgcgg ccgagcagcc tgcccagtgt gggcagggggc agccgttcgt gctgccgtg     1440
ggcgtgagct ccaggaatga ggactacccc cgaacctgca ggatgtgttt ttatggcaca     1500
ggcctcatcg cgggccacgg cttcaccagc cctgaacgca ccccgggggt cttcatcctc     1560
ttcgatgagg accgcttcgg gttcgtctgg ctggagctga atccttcag cctgtacagc      1620
cgggtccagg ccaccttccg gaacgcagat gcgccgtccc cacaggcctt cgatgagatg     1680
ctcaagaaca ttcagtccct cacctcctga ccggccacat ccttgccgcc acatcccggg     1740
tggctctggg gctctgaact ctgacctgtg aatagaagca gcatgcactt tggaaatccg     1800
gccttttgac cagaacgcac acctcgtcgg ggggcccagt ccagccaccc cccagcactt     1860
tatgtagaga gtgtgacata gacctgcata tttgtcagtg ccatgatgga agaagctgag     1920
catgtcttac caaaaacaga gagaacgagc ctgaatacag cagatgtagg ggacagccgt     1980
gggaccgcgt gagaattgaa gcggtggggt tcccgcaccc tgggctggct ggtggttttc     2040
tcgggaagca ggaccctcct gactggtgct cttcctgtga gcggatagag tgatagactg     2100
ggtcgtgtgt gagacgcatg tgctccaccc cactccttt gggggaagcc aggcaacagt      2160
ggcctctggg aggggtcag gaagaggcga acagctcagg cagcgcaggt gtgatgggca      2220
cagtacgcag agcaagctcg ggaagttggt aggatctcag gcttggggcc gggactctgg     2280
agtgaatccc catttctcta ccggcttgct tggagtttgg acagaagcat ttcacctctg     2340
atctcagctt ccccacctgt ggagtgggtt tagtgacctg agtcactagg gaatgtcacc     2400
tgaatgcaca gcccagccca tgcacctgcc ccagcccctc cagctttgga gccaaggcca     2460
tcgttccagc cacttgactg tcctcgacgg cctgttccag acagggcgtt tgttttgtcc     2520
atgccttcct ccctgcacgc acacggcgtc aaaaccaagc tgccggccac tgtctccaga     2580
acgcaaggct ccaggcccgt gtgtctgaag cagtgagtgg tccacacagg tgccaggagt     2640
gcccatatga gatgacgagg aaacccctt gcaggtgagg ggacagcttt ctagaaaagc      2700
cacacctgca tctggggaca cactttggaa agtgggaccc tccagcctgg agaccccatg     2760
gactgatgcc tccactgctg tgtgcccat gttgtgttaa cacctgcgtg tggggacccc      2820
atctgaggtc ttggctgagg ttggcatctc ctgaagaaca gagagcacgg tgtccagagc     2880
tggcccttcc cccagcccac agccagctcc gtgcccgagt gggcgtcccc agcgagcctt     2940
ccctctctgc cgcttgtcct tgtgtctggg ctgctccaag tccttgtgct gggcaccctg     3000
gacacgtcct gctggtgagg gacctcggga aggtgacagt ctgtgtgcct tggtgtggag     3060
accaacctga ggatgtcctg ggaaatgttt tcctgatgaa tttctccttg actggccttt     3120
aaagaacata agaattccca ttgcccagcc tcagtgcatt tggcaaatgc ttactttgct     3180
```

```
tcccagagtc agagaattgg caaaggttcc taaatggtaa tctggccggc ctgggagaaa    3240
gactcacgag aaaagccagt ggagaaagcg cccttccagg gcggcagcag cgggagccac    3300
gcagaccccg aggcgcacct gctggctctt gtgtgtggcc ccagtttcta gcggcttttg    3360
cagcattagc ctacaagctt tgtcactccc tgccctctgt ggtggtcact gttttttctct   3420
cttgccaaat gaggcagtct ctgagtgacg gtgactgtgg ccttgaagcc tggaggactg    3480
ttgggcatgt agactggcac cttgaagatt caccattgtt taaataaaat caagcaaatg    3540
cttttttacc aagagcccga gcctcgctct aagggacgca gtcctagagg cgtgcccttt    3600
ggggcttgaa gagcacactg tgggacgcac gtgcttctga ttaaaggaat ctcagatctc    3660
aattacgctt ccagtgtttg ggtatagaaa tagcttccac ccatcatgtc tcagccatgg    3720
gctgttggtc agttcatgtg gctcctggtt ctggtgtgta tgttggggc ggggtctct      3780
ccatggtggt gacctgcagt gatgccaggc agggccagag ccacacagcc aggaaaggga    3840
ggccttttttg gccgcacagc cagtcccttc agtcgtgact acaggtcttg ttttttccgc   3900
tccgatgtgt ccttagccag ttcttggctc cggttctgta gggacaggca ctgaatctgc    3960
gcgcctcaaa acagcagctt cccttccggg ggagggcatc caccctctca ggggatcctg    4020
caggtggccc atttcctgca ggtgagaact cggaagggct gatgtcgtca tcagaggcct    4080
aagggcagct gagagttgga taaaaccgtt tccaaggagg aggctgagta acccagttca    4140
ggacagccaa gcgcattagg cttgattggg gaaggtggca ggtggagttg ggaggttggg    4200
actctccatc ttttgcacca cggatgcctt tctgtcgctg tctcactctg ggcaggatc     4260
aagtctgctc tctggagtgg ggctgcctgc agtgcagctc tgcacacctg aacgtgttct    4320
ttgtcacttg tttggaaatg atgtgattga agatttcaga gaggtcattg gaggcttttc    4380
tgtgccggca ctgaatgttc atttgcatga ggaagttgca aacgacttct gcaggctgag    4440
attcaaggca ggtggtattg gggtccctca gcccacctgg gccgtgacct caagtgtcca    4500
ctgctgagtg tgagtggctt tgcaggcctg gtggtgggag agcctcaggc tccctccttc    4560
ttcgttcctg accatgccct gggcccttc agtctgcctg cggctctgtg gcatccctgc     4620
cctgacactg ggcacctgtg cccctagcaa gcccacctgg cacacgagga gggaggggtg    4680
ggtggccatg tccttcctct agccacatgc cctgctggcc gctccattct gagctttgtg    4740
cagaaccggg tctgagctgg agattttttct ctgagaacct gcagttgtgc tgcagccgca   4800
cgcaagggcc cttcagccgc tggctctggc ttccctgact cctcagggcg tgttcacccc    4860
caggctttct cacctgcaca cggttaggcc attttcagtg ctcgtgggca gtcacggaca    4920
gcagcagaaa ctcctcagcc cctttgttac ttcagaacgc ctgcccacat gcatcttctg    4980
agctcgtgtt gtcctcatgg ccgtggggtc ttgggtgcga acaggagatg ctgagctgtg    5040
gtccaccgtc caaggtgctg cagaaagcag ctaggctctt ttaggatgtt tctattctgg    5100
ttgctgcctt cgtggtgtaa cttttaagaa cacttacggg aatgtgctca tagaaccatc    5160
acctgtcctg agaataaaac tcctggaatc atgatcaagt ccagtgttaa cgtggcccaa    5220
cctgtctgta cttctgggga gagaccagga acatcactgg actcctcatc cccgtaatta    5280
tttagagaag atgcaagcag cagatagtct ccatgcggct ggtactttt ttgttgtttt     5340
ttgagacagg tcttgctct gtcacctggg ctggagtgca gagcggcgat catggctccc     5400
tgaggcctca acctactagg ctcaagctgt ctgcccgcct tagcctccca agtagctggg    5460
accacaggca cccaccacca ccatgcttgg ctaacttgtt tttgtagaga tggagttttg    5520
ccatgttgct caggttggtc tcgaactccc gatctcaggt gatccacccg cctcggcctc    5580
```

-continued

| | |
|---|---|
| ccaaagtgct gggattacag gcgtgagccc ctgcgcccca gccttggggc ctgtctttga | 5640 |
| atgggaatga gactgtgcaa accgtggact accctgtgtc acccacagct cagtggcctg | 5700 |
| cctgccggcc ctcaggggct gctgaccggg agaccagcca gagcacgagg gggtcagggc | 5760 |
| tgtgtgggtt ttggcctgat tctgcatttg gttgtttctg ggggccatgt agcctgcctg | 5820 |
| cattaggaaa gcgctgtgcc atctgatcat gagcacctct gcaccccctg gtaaggtgac | 5880 |
| cttgcagcag gagctgtgcc ctgcctgggt aggcacccac taggtaggac cggagcaatc | 5940 |
| ctggcagccg ccacctgcac ccgtgcactt gtttctcctc acagtttcaa gtaaatccgt | 6000 |
| ttttgaaggc t | 6011 |

<210> SEQ ID NO 18
<211> LENGTH: 7521
<212> TYPE: DNA
<213> ORGANISM: Homo sapiens

<400> SEQUENCE: 18

| | |
|---|---|
| ggcatggcgg tgtgtgctcg cctttgcggc gtgggcccgt cgcgcggatg tcggcgccgc | 60 |
| cagcagcgcc ggggcccggc cgagacggcg gcggccgaca gcgagccgga cacagacccc | 120 |
| gaggaggagc gcatcgaggc tagcgccggg gtcgggggcg gcttgtgcgc gggcccctcg | 180 |
| ccgccgcccc cgcgctgctc gctgctggag ctgccgcccg agctgctggt ggagatcttc | 240 |
| gcgtcgctgc cgggcacgga cctacccagc ttggcccagg tctgcacgaa gttccggcgc | 300 |
| atcctccaca ccgacaccat ctggaggagg cgttgccgtg aggagtatgg tgtttgcgaa | 360 |
| aacttgcgga agctggagat cacaggcgtg tcttgtcggg acgtctatgc gaagctgctt | 420 |
| caccgatata gacacatttt gggattgtgg cagccagata tcgggccata cggaggactg | 480 |
| ctgaacgtgg tggtggacgg cctgttcatc atcgggtgga tgtacctgcc tccccatgac | 540 |
| ccccacgtcg atgaccctat gagattcaag cctctgttca ggatccacct gatggagagg | 600 |
| aaggctgcca cagtggagtg catgtacggc cacaaagggc cccaccacgg ccacatccag | 660 |
| attgtgaaga aggatgagtt ctccaccaag tgcaaccaga cggaccacca caggatgtcc | 720 |
| ggcgggaggc aggaggagtt tcggacgtgg ctgagggagg aatgggggcg cacgctggag | 780 |
| gacatcttcc acgagcacat gcaggagctc atcctgatga agttcatcta caccagtcag | 840 |
| tacgacaact gcctgaccta ccgccgcatc tacctgccgc ccagccgccc cgacgacctc | 900 |
| atcaagcctg gcctcttcaa aggtacctat ggcagccacg gcctggagat tgtgatgctc | 960 |
| agcttccacg gccggcgtgc caggggcacc aagatcacgg gcgaccccaa catccccgct | 1020 |
| gggcagcaga cagtggagat cgacctgagg catcggatcc agctgcccga cctcgagaac | 1080 |
| cagcgcaact tcaatgagct ctcccgcatc gtcctggagg tgcgcgagag ggtgcgccag | 1140 |
| gagcagcagg aaggcgggca cgaggcgggc gagggtcgtg gccggcaggg ccccggggag | 1200 |
| tcccagccaa gccctgccca gcccagggca gaggcgccca gcaagggccc agatgggaca | 1260 |
| cctggtgagg atggtggcga gcctggggat gccgtagctg cggccgagca gcctgcccag | 1320 |
| tgtgggcagg ggcagccgtt cgtgctgccc gtgggcgtga gctccaggaa tgaggactac | 1380 |
| ccccgaacct gcaggatgtg tttttatggc acaggcctca tcgcgggcca cggcttcacc | 1440 |
| agccctgaac gcaccccccgg ggtcttcatc ctcttcgatg aggaccgctt cgggttcgtc | 1500 |
| tggctggagc tgaaatcctt cagcctgtac agccgggtcc aggccacctt ccggaacgca | 1560 |
| gatgcgccgt ccccacaggc cttcgatgag atgctcaaga acattcagtc cctcacctcc | 1620 |

```
tgaccggcca catccttgcc gccacatccc gggtggctct ggggctctga actctgacct    1680
gtgaatagaa gcagcatgca ctttggaaat ccggccttt gaccagaacg cacacctcgt     1740
cggggggccc agtccagcca cccccagca ctttatgtag agagtgtgac atagacctgc     1800
atatttgtca gtgccatgat ggaagaagct gagcatgtct taccaaaaac agagagaacg    1860
agcctgaata cagcagatgt aggggacagc cgtgggaccg cgtgagaatt gaagcggtgg    1920
ggttcccgca ccctgggctg gctggtggtt ttctcgggaa gcaggaccct cctgactggt    1980
gctcttcctg tgagcggata gagtgataga ctgggtcgtg tgtgagacgc atgtgctcca    2040
ccccactcct tttgggggaa gccaggcaac agtggcctct gggagggggt caggaagagg    2100
cgaacagctc aggcagcgca ggtgtgatgg gcacagtacg cagagcaagc tcgggaagtt    2160
ggtaggatct caggcttggg gccgggactc tggagtgaat ccccatttct ctaccggctt    2220
gcttggagtt tggacagaag catttcacct ctgatctcag cttccccacc tgtggagtgg    2280
gtttagtgac ctgagtcact agggaatgtc acctgaatgc acagcccagc ccatgcacct    2340
gccccagccc ctccagcttt ggagccaagg ccatcgttcc agccacttga ctgtcctcga    2400
cggcctgttc cagacagggc gtttgttttg tccatgcctt cctccctgca cgcacacggc    2460
gtcaaaacca agctgccggc cactgtctcc agaacgcaag gctccaggcc cgtgtgtctg    2520
aagcagtgag tggtccacac aggtgccagg agtgcccata tgagatgacg aggaaacccc    2580
tttgcaggtg aggggacagc tttctagaaa agccacacct gcatctgggg acacactttg    2640
gaaagtggga ccctccagcc tggagacccc atggactgat gcctccactg ctgtgtgccc    2700
catgttgtgt taacacctgc gtgtggggac cccatctgag gtcttggctg aggttggcat    2760
ctcctgaaga acagagagca cggtgtccag agctggccct tcccccagcc cacagccagc    2820
tccgtgcccg agtgggcgtc cccagcgagc cttccctctc tgccgcttgt ccttgtgtct    2880
gggctgctcc aagtccttgt gctgggcacc ctggacacgt cctgctggtg agggacctcg    2940
ggaaggtgac agtctgtgtg ccttggtgtg agaccaacc tgaggatgtc ctgggaaatg     3000
ttttcctgat gaatttctcc ttgactggcc tttaaagaac ataagaattc ccattgccca    3060
gcctcagtgc atttggcaaa tgcttacttt gcttcccaga gtcagagaat tggcaaaggt    3120
tcctaaatgg taatctggcc ggcctgggag aaagactcac gagaaaagcc agtggagaaa    3180
gcgcccttcc agggcggcag cagcgggagc cacgcagacc ccgaggcgca cctgctggct    3240
cttgtgtgtg gccccagttt ctagcggctt ttgcagcatt agcctacaag ctttgtcact    3300
ccctgccctc tgtggtggtc actgttttc tctcttgcca aatgaggcag tctctgagtg     3360
acggtgactg tggccttgaa gcctggagga ctgttgggca tgtagactgg cacccttgaag   3420 attcaccatt gtttaaataa aatcaagcaa atgcttttt accaagagcc cgagcctcgc     3480
tctaagggac gcagtcctag aggcgtgccc tttgggcttt gaagagcaca ctgtgggacg    3540
cacgtgcttc tgattaaagg aatctcagat ctcaattacg cttccagtgt ttgggtatag    3600
aaatagcttc cacccatcat gtctcagcca tgggctgttg gtcagttcat gtggctcctg    3660
gttctggtgt gtatgttggg ggcggggtc tctccatggt ggtgacctgc agtgatgcca     3720
ggcagggcca gagccacaca gccaggaaag ggaggccttt ttggccgcac agccagtccc    3780
ttcagtcgtg actacaggtc ttgttttttc cgctccgatg tgtccttagc cagttcttgg    3840
ctccggttct gtagggacag gcactgaatc tgcgcgcctc aaaacagcag cttcccttcc    3900 ggggagggc atccaccctc tcaggggatc ctgcaggtgg cccatttcct gcaggtgaga     3960
actcggaagg gctgatgtcg tcatcagagg cctaagggca gctgagagtt ggataaaacc    4020
```

```
gtttccaagg aggaggctga gtaacccagt tcaggacagc caagcgcatt aggcttgatt    4080
ggggaaggtg gcaggtggag ttgggaggtt gggactctcc atcttttgca ccacggatgc    4140
ctttctgtcg ctgtctcact ctggggcagg atcaagtctg ctctctggag tggggctgcc    4200
tgcagtgcag ctctgcacac ctgaacgtgt tctttgtcac ttgtttggaa atgatgtgat    4260
tgaagatttc agagaggtca ttggaggctt ttctgtgccg gcactgaatg ttcatttgca    4320
tgaggaagtt gcaaacgact tctgcaggct gagattcaag gcaggtggta ttggggtccc    4380
tcagcccacc tggccgtgca cctcaagtgt ccactgctga gtgtgagtgg ctttgcaggc    4440
ctggtggtgg gagagcctca ggctccctcc ttcttcgttc ctgaccatgc cctgggcccc    4500
ttcagtctgc ctgcggctct gtggcatccc tgccctgaca ctgggcacct gtgcccctag    4560
caagcccacc tggcacacga ggagggaggg gtgggtggcc atgtccttcc tctagccaca    4620
tgccctgctg gccgctccat tctgagcttt gtgcagaacc gggtctgagc tggagatttt    4680
tctctgagaa cctgcagttg tgctgcagcc gcacgcaagg gcccttcagc cgctggctct    4740
ggcttccctg actcctcagg gcgtgttcac ccccaggctt tctcacctgc acacggttag    4800
gccattttca gtgctcgtgg gcagtcacgg acagcagcag aaactcctca gccccttgt     4860 tacttcagaa cgcctgccca catgcatctt ctgagctcgt gttgtcctca tggccgtggg    4920
gtcttgggtg cgaacaggag atgctgagct gtggtccacc gtccaaggtg ctgcagaaag    4980
cagctaggct ctttaggat gtttctattc tggttgctgc cttcgtggtg taactttaa      5040 gaacacttac gggaatgtgc tcatagaacc atcacctgtc ctgagaataa aactcctgga    5100
atcatgatca gtccagtgt taacgtggcc caacctgtct gtacttctgg ggagagacca     5160
ggaacatcac tggactcctc atccccgtaa ttatttagag aagatgcaag cagcagatag    5220
tctccatgcg gctggtactt ttttgttgt ttttgagac agggtcttgc tctgtcacct      5280
gggctggagt gcagagcggc gatcatggct ccctgaggcc tcaacctact aggctcaagc    5340
tgtctgcccg ccttagcctc ccaagtagct gggaccacag gcacccacca ccaccatgct    5400
tggctaactt gttttttgtag agatggagtt ttgccatgtt gctcaggttg gtctcgaact    5460
cccgatctca ggtgatccac ccgcctcggc ctcccaaagt gctgggatta caggcgtgag    5520
cccctgcgcc ccagccttgg ggcctgtctt tgaatgggaa tgagactgtg caaaccgtgg    5580
actaccctgt gtcacccaca gctcagtggc ctgcctgccg gccctcaggg gctgctgacc    5640
gggagaccag ccagagcacg aggggtcag ggctgtgtgg gttttggcct gattctgcat      5700
ttggttgttt ctgggggcca tgtagcctgc ctgcattagg aaagcgctgt gccatctgat    5760
catgagcacc tctgcacccc ctggtaaggt gaccttgcag caggagctgt gccctgcctg    5820
ggtaggcacc cactaggtag gaccggagca atcctggcag ccgccacctg cacccgtgca    5880
cttgtttctc ctcacagttt caagtaaatc cgttttgaa ggcttgttgt gtgttttgtg      5940
atttctttgg gaatatgagt tggacggagg cgagagcctt aagccatgcg agctgtcggc    6000
ctgggaaccc agacttccca gcttcttgag gaagtgtcag atttcccgcg ttgacagaag    6060
ggagcattga agggatgcct tggagcccag acagtggttg tccctgtgtc cttccctttg    6120
acctggcatc agaggtgtct cgagtcccta cccaggacc cagaggagtt cgggcccag      6180 tagattttct tagattaag ccaaagtgag ttgcattatc tgcaacgagg acagatatgg      6240
gagggaatgt gctgagagcc aggcagatga actgaggatc tcattgatct ttcttttgtg    6300
tttactaaac tcatatgttc ttgtaaacag ttctttagca tagacagtga aagtaccccc    6360
```

```
tgttctcatc ccagcctccc cgtgagtcac tgctgctaat taatgctgtt agcttggaat     6420
tgtagaaaca ggatgttttc catggtaatg cactcaaagt acaccctcga ttggcagaaa     6480
ttggcaagtg tgattttcca agtgttggca gtgatgcagg ggaacaggaa cgcaggtggg     6540
gcagctgttt tggggacagc tggtactagc tcatggcact aaggacacgg gcccagggac     6600
tggcatctgc atcctgaggt gtccaccctc gggcaacgcg agagcccagg catgggccac     6660
gcagggatgt tcattgctac actgtgacaa ctgtcacagg ccggaaggag gcaggtggac     6720
tacggtggag ccacccatgc tgtcacctgg cagacgggca cacagccttg ttccgttgca     6780
aaacaagtga gagatggtat tggtgtaaca tgtaaaaatg caaatactta atttttatca     6840
attcatgtgt ggggaaaagc tgaagatacg cgtgggaatg tgtggtcac ttctaggggt     6900 gtcggagggt agaacttcaa ctgttttgct ttaaaaagta aggatcgcat ggcagaacta     6960
gcatctgttc acctgttgat cctgataccg tggattacga gacccccct ctttctgtg     7020 tggttcagaa acaagcccct cagacaggac acagtgccca gggcagtga cctgcaggcc     7080 cacccactgc catctccgct ggtctcgggg ttgccacata gcctgccagc tgcggctgct     7140
tcctgggtgc cctccaggga gagcaggga tcgtgggtcc ccggcggtgg gtgtttcctt     7200
ctccggggag agcaggggat cgtgggtccc cggtggtggg tgtttccttc tctaaggttt     7260
gctgctgttt ccaggccttt ctgtggggcc tgggtcctgt cctggggcca agccacgggg     7320
tcatcctcag ctgcactggg cgtgccaacc acaaacgagt cacttgctac aagcagcacc     7380
atgcagcctc ctgtctggac gagaccctgc ccccacaga ctggagacgc accccgattt     7440
cccaggtcac aggggaagt gtggatctga taagggacta aatgtggcgt ctttcatatg     7500
tttctcttac atattttatt t                                               7521

<210> SEQ ID NO 19
<211> LENGTH: 7608
<212> TYPE: DNA
<213> ORGANISM: Homo sapiens

<400> SEQUENCE: 19
ggcatggcgg tgtgtgctcg cctttgcggc gtgggcccgt cgcgcggatg tcggcgccgc       60
cagcagcgcc ggggcccggc cgagacggcg gcggccgaca gcgagccgga cacagacccc      120
gaggaggagc gcatcgaggc tagcgccggg gtcggggggcg gcttgtgcgc gggcccctcg      180
ccgccgcccc cgcgctgctc gctgctggag ctgccgcccg agctgctggt ggagatcttc      240
gcgtcgctgc cgggcacgga cctacccagc ttggcccagg tctgcacgaa gttccggcgc      300
atcctccaca ccgacaccat ctggaggagg cgttgccgtg aggagtatgg tgtttgcgaa      360
aacttgcgga agctggagat cacaggcgtg tcttgtcggg acgtctatgc gaagcgtata      420
aaccctcgcg tgaagtcggg acgttttgtg aaaattctcc ctgattatga gcacatggcg      480
tacagagacg tttacacctg cctgcttcac cgatatagac acattttggg attgtggcag      540
ccagatatcg ggccatacgg aggactgctg aacgtggtgg tggacggcct gttcatcatc      600
gggtggatgt acctgcctcc ccatgacccc cacgtcgatg accctatgag attcaagcct      660
ctgttcagga tccacctgat ggagaggaag gctgccacag tggagtgcat gtacggccac      720
aaagggcccc accacggcca catccagatt gtgaagaagg atgagttctc caccaagtgc      780
aaccagacgg accaccacag gatgtccggc gggaggcagg aggagtttcg acgtggctg      840 agggaggaat gggggcgcac gctggaggac atcttccacg agcacatgca ggagctcatc      900
ctgatgaagt tcatctacac cagtcagtac gacaactgcc tgacctaccg ccgcatctac      960
```

```
ctgccgccca gccgcccga cgacctcatc aagcctggcc tcttcaaagg tacctatggc    1020
agccacggcc tggagattgt gatgctcagc ttccacggcc ggcgtgccag gggcaccaag    1080
atcacgggcg accccaacat ccccgctggg cagcagacag tggagatcga cctgaggcat    1140
cggatccagc tgcccgacct cgagaaccag cgcaacttca atgagctctc ccgcatcgtc    1200
ctggaggtgc gcgagagggt gcgccaggag cagcaggaag gcgggcacga ggcgggcgag    1260
ggtcgtggcc ggcagggccc ccgggagtcc cagccaagcc ctgcccagcc cagggcagag    1320
gcgcccagca agggcccaga tgggacacct ggtgaggatg gtggcgagcc tggggatgcc    1380
gtagctgcgg ccgagcagcc tgcccagtgt gggcagggc agccgttcgt gctgccgtg    1440 ggcgtgagct ccaggaatga ggactacccc gaacctgca ggatgtgttt ttatggcaca    1500
ggcctcatcg cgggccacgg cttcaccagc cctgaacgca ccccggggt cttcatcctc    1560 ttcgatgagg accgcttcgg gttcgtctgg ctggagctga atccttcag cctgtacagc    1620 cgggtccagg ccaccttccg gaacgcagat gcgccgtccc acaggccttc gatgagatg    1680 ctcaagaaca ttcagtccct cacctcctga ccggccacat ccttgccgcc acatcccggg    1740
tggctctggg gctctgaact ctgacctgtg aatagaagca gcatgcactt tggaaatccg    1800
gccttttgac cagaacgcac acctcgtcgg ggggcccagt ccagccaccc cccagcactt    1860
tatgtagaga gtgtgacata gacctgcata tttgtcagtg ccatgatgga agaagctgag    1920
catgtcttac caaaaacaga gagaacgagc ctgaatacag cagatgtagg ggacagccgt    1980
gggaccgcgt gagaattgaa gcggtgggt tcccgcaccc tgggctggct ggtggttttc    2040
tcgggaagca ggaccctcct gactggtgct cttcctgtga gcggatagag tgatagactg    2100
ggtcgtgtgt gagacgcatg tgctccaccc cactccttt gggggaagcc aggcaacagt    2160
ggcctctggg aggggtcag gaagaggcga acagctcagg cagcgcaggt gtgatgggca    2220
cagtacgcag agcaagctcg ggaagttggt aggatctcag gcttggggcc gggactctgg    2280
agtgaatccc catttctcta ccggcttgct tggagtttgg acagaagcat ttcacctctg    2340
atctcagctt ccccacctgt ggagtgggtt tagtgacctg agtcactagg gaatgtcacc    2400
tgaatgcaca gcccagccca tgcacctgcc ccagcccctc cagctttgga gccaaggcca    2460
tcgttccagc cacttgactg tcctcgacgg cctgttccag acagggcgtt tgttttgtcc    2520
atgccttcct ccctgcacgc acacggcgtc aaaaccaagc tgccggccac tgtctccaga    2580
acgcaaggct ccaggcccgt gtgtctgaag cagtgagtgg tccacacagg tgccaggagt    2640
gcccatatga gatgacgagg aaaccccttt gcaggtgagg ggacagcttt ctagaaaagc    2700
cacacctgca tctggggaca cactttggaa agtgggaccc tccagcctgg agaccccatg    2760
gactgatgcc tccactgctg tgtgcccat gttgtgttaa cacctgcgtg tggggacccc    2820
atctgaggtc ttggctgagg ttggcatctc ctgaagaaca gagagcacgg tgtccagagc    2880
tggcccttcc cccagcccac agccagctcc gtgcccgagt gggcgtcccc agcgagcctt    2940
ccctctctgc cgcttgtcct tgtgtctggg ctgctccaag tccttgtgct gggcaccctg    3000
gacacgtcct gctggtgagg gacctcggga aggtgacagt ctgtgtgcct tggtgtggag    3060
accaacctga ggatgtcctg ggaaatgttt tcctgatgaa tttctccttg actggccttt    3120
aaagaacata agaattccca ttgcccagcc tcagtgcatt tggcaaatgc ttactttgct    3180
tcccagagtc agagaattgg caaaggttcc taaatggtaa tctggccggc ctgggagaaa    3240
gactcacgag aaaagccagt ggagaaagcg cccttccagg gcggcagcag cgggagccac    3300
```

```
gcagacccg   aggcgcacct   gctggctctt   gtgtgtggcc   ccagtttcta   gcggcttttg    3360
cagcattagc  ctacaagctt   tgtcactccc   tgccctctgt   ggtggtcact   gttttctct     3420
cttgccaaat  gaggcagtct   ctgagtgacg   gtgactgtgg   ccttgaagcc   tggaggactg    3480
ttgggcatgt  agactggcac   cttgaagatt   caccattgtt   taaataaaat   caagcaaatg    3540
cttttttacc  aagagcccga   gcctcgctct   aagggacgca   gtcctagagg   cgtgcccttt    3600
ggggcttgaa  gagcacactg   tgggacgcac   gtgcttctga   ttaaaggaat   ctcagatctc    3660
aattacgctt  ccagtgtttg   ggtatagaaa   tagcttccac   ccatcatgtc   tcagccatgg    3720
gctgttggtc  agttcatgtg   gctcctggtt   ctggtgtgta   tgttggggc    gggggtctct    3780
ccatggtggt  gacctgcagt   gatgccaggc   agggccagag   ccacacagcc   aggaaaggga    3840
ggccttttg   gccgcacagc   cagtcccttc   agtcgtgact   acaggtcttg   tttttccgc     3900
tccgatgtgt  ccttagccag   ttcttggctc   cggttctgta   gggacaggca   ctgaatctgc    3960
gcgcctcaaa  acagcagctt   cccttccggg   ggagggcatc   caccctctca   ggggatcctg    4020
caggtggccc  atttcctgca   ggtgagaact   cggaagggct   gatgtcgtca   tcagaggcct    4080
aagggcagct  gagagttgga   taaaaccgtt   tccaaggagg   aggctgagta   acccagttca    4140
ggacagccaa  gcgcattagg   cttgattggg   gaaggtggca   ggtggagttg   ggaggttggg    4200
actctccatc  ttttgcacca   cggatgcctt   tctgtcgctg   tctcactctg   ggcaggatc     4260
aagtctgctc  tctggagtgg   ggctgcctgc   agtgcagctc   tgcacacctg   aacgtgttct    4320
ttgtcacttg  tttggaaatg   atgtgattga   agatttcaga   gaggtcattg   gaggcttttc    4380
tgtgccggca  ctgaatgttc   atttgcatga   ggaagttgca   aacgacttct   gcaggctgag    4440
attcaaggca  ggtggtattg   gggtccctca   gcccacctgg   gccgtgacct   caagtgtcca    4500
ctgctgagtg  tgagtggctt   tgcaggcctg   gtggtgggag   agcctcaggc   tccctccttc    4560
ttcgttcctg  accatgccct   gggcccttc    agtctgcctg   cggctctgtg   gcatccctgc    4620
cctgacactg  ggcacctgtg   ccctagcaa    gcccacctgg   cacacgagga   gggaggggtg    4680
ggtggccatg  tccttcctct   agccacatgc   cctgctggcc   gctccattct   gagctttgtg    4740
cagaaccggg  tctgagctgg   agattttct    ctgagaacct   gcagttgtgc   tgcagccgca    4800
cgcaagggcc  cttcagccgc   tggctctggc   ttccctgact   cctcagggcg   tgttcacccc    4860
caggctttct  cacctgcaca   cggttaggcc   attttcagtg   ctcgtgggca   gtcacggaca    4920
gcagcagaaa  ctcctcagcc   cctttgttac   ttcagaacgc   ctgcccacat   gcatcttctg    4980
agctcgtgtt  gtcctcatgg   ccgtggggtc   ttgggtgcga   acaggagatg   ctgagctgtg    5040
gtccaccgtc  caaggtgctg   cagaaagcag   ctaggctctt   ttaggatgtt   tctattctgg    5100
ttgctgcctt  cgtggtgtaa   cttttaagaa   cacttacggg   aatgtgctca   tagaaccatc    5160
acctgtcctg  agaataaaac   tcctggaatc   atgatcaagt   ccagtgttaa   cgtggcccaa    5220
cctgtctgta  cttctgggga   gagaccagga   acatcactgg   actcctcatc   cccgtaatta    5280
tttagagaag  atgcaagcag   cagatagtct   ccatgcggct   ggtactttt    ttgttgtttt    5340
ttgagacagg  tcttgctct    gtcacctggg   ctggagtgca   gagcggcgat   catggctccc    5400
tgaggcctca  acctactagg   ctcaagctgt   ctgcccgcct   tagcctccca   agtagctggg    5460
accacaggca  cccaccacca   ccatgcttgg   ctaacttgtt   tttgtagaga   tggagttttg    5520
ccatgttgct  caggttggtc   tcgaactccc   gatctcaggt   gatccacccg   cctcggcctc    5580
ccaaagtgct  gggattacag   gcgtgagccc   ctgcgcccca   gccttgggc    ctgtctttga    5640
atgggaatga  gactgtgcaa   accgtggact   accctgtgtc   acccacagct   cagtggcctg    5700
```

```
cctgccggcc ctcaggggct gctgaccggg agaccagcca gagcacgagg gggtcagggc    5760
tgtgtgggtt ttggcctgat tctgcatttg gttgtttctg ggggccatgt agcctgcctg    5820
cattaggaaa gcgctgtgcc atctgatcat gagcacctct gcaccccctg gtaaggtgac    5880
cttgcagcag gagctgtgcc ctgcctgggt aggcacccac taggtaggac cggagcaatc    5940
ctggcagccg ccacctgcac ccgtgcactt gtttctcctc acagtttcaa gtaaatccgt    6000
ttttgaaggc ttgttgtgtg ttttgtgatt tctttgggaa tatgagttgg acggaggcga    6060
gagccttaag ccatgcgagc tgtcggcctg gaacccaga cttcccagct tcttgaggaa     6120
gtgtcagatt tcccgcgttg acagaaggga gcattgaagg gatgccttgg agcccagaca    6180
gtggttgtcc ctgtgtcctt ccctttgacc tggcatcaga ggtgtctcga gtccctaccc    6240
agggacccag aggagttcgg gccccagtag attttcttag atttaagcca aagtgagttg    6300
cattatctgc aacgaggaca gatatgggag ggaatgtgct gagagccagg cagatgaact    6360
gaggatctca ttgatctttc ttttgtgttt actaaactca tatgttcttg taaacagttc    6420
tttagcatag acagtgaaag taccccctgt tctcatccca gcctcccgt gagtcactgc     6480 tgctaattaa tgctgttagc ttggaattgt agaaacagga tgttttccat ggtaatgcac    6540
tcaaagtaca ccctcgattg gcagaaattg gcagtgtga ttttccaagt gttggcagtg     6600
atgcagggga acaggaacgc aggtggggca gctgttttgg ggacagctgg tactagctca    6660
tggcactaag gacacgggcc cagggactgg catctgcatc ctgaggtgtc caccctcggg    6720
caacgcgaga gcccaggcat gggccacgca gggatgttca ttgctacact gtgacaactg    6780
tcacaggccg gaaggaggca ggtggactac ggtggagcca cccatgctgt cacctggcag    6840
acgggcacac agccttgttc cgttgcaaaa caagtgagag atggtattgg tgtaacatgt    6900
aaaaatgcaa atacttaatt tttatcaatt catgtgtggg gaaaagctga agatacgcgt    6960
gggaatggtg tggtcacttc tagggtgtc ggagggtaga acttcaactg ttttgcttta     7020
aaaagtaagg atcgcatggc agaactagca tctgttcacc tgttgatcct gataccgtgg    7080
attacgagac cccccctctt ttctgtgtgg ttcagaaaca agcccctcag acaggacaca    7140
gtgcccaggg gcagtgacct gcaggcccac ccactgccat ctccgctggt ctcggggttg    7200
ccacatagcc tgccagctgc ggctgcttcc tgggtgccct ccagggagag caggggatcg    7260
tgggtccccg gcggtggtg tttccttctc cggggagagc aggggatcgt gggtccccgg     7320
tggtgggtgt ttccttctct aaggtttgct gctgtttcca ggcctttctg tggggcctgg    7380
gtcctgtcct ggggccaagc cacggggtca tcctcagctg cactgggcgt gccaaccaca    7440
aacgagtcac ttgctacaag cagcaccatg cagcctcctg tctggacgag accctgcccc    7500
ccacagactg gagacgcacc ccgatttccc aggtcacagg gggaagtgtg gatctgataa    7560
gggactaaat gtggcgtctt tcatatgttt ctcttacata ttttattt                 7608
```

<210> SEQ ID NO 20
<211> LENGTH: 21
<212> TYPE: DNA
<213> ORGANISM: Homo sapiens

<400> SEQUENCE: 20
gtgaagaagg atgagttctc c    21

<210> SEQ ID NO 21
<211> LENGTH: 20
<212> TYPE: DNA

```
<213> ORGANISM: Homo sapiens

<400> SEQUENCE: 21
agctgagcat cacaatctcc                                              20

<210> SEQ ID NO 22
<211> LENGTH: 25
<212> TYPE: DNA
<213> ORGANISM: Homo sapiens

<400> SEQUENCE: 22
ggagcttccc caactcataa atgcc                                        25

<210> SEQ ID NO 23
<211> LENGTH: 25
<212> TYPE: DNA
<213> ORGANISM: Homo sapiens

<400> SEQUENCE: 23
gcatgatgtc tgatgtggtc agtaa                                        25

<210> SEQ ID NO 24
<211> LENGTH: 20
<212> TYPE: DNA
<213> ORGANISM: Homo sapiens

<400> SEQUENCE: 24
tgcgaagctg cttcaccgat                                              20

<210> SEQ ID NO 25
<211> LENGTH: 21
<212> TYPE: DNA
<213> ORGANISM: Homo sapiens

<400> SEQUENCE: 25
ggccgtacat gcactccact g                                            21

<210> SEQ ID NO 26
<211> LENGTH: 20
<212> TYPE: DNA
<213> ORGANISM: Homo sapiens

<400> SEQUENCE: 26
gagaacctgc agttgtgctg                                              20

<210> SEQ ID NO 27
<211> LENGTH: 20
<212> TYPE: DNA
<213> ORGANISM: Homo sapiens

<400> SEQUENCE: 27
atggtgctgc ttgtagcaag                                              20

<210> SEQ ID NO 28
<211> LENGTH: 21
<212> TYPE: DNA
<213> ORGANISM: Homo sapiens

<400> SEQUENCE: 28
tgcccatatg agatgacgag g                                            21

<210> SEQ ID NO 29
<211> LENGTH: 21
```

-continued

```
<212> TYPE: DNA
<213> ORGANISM: Homo sapiens

<400> SEQUENCE: 29
acactcagca gtggacactt g                                             21

<210> SEQ ID NO 30
<211> LENGTH: 24
<212> TYPE: DNA
<213> ORGANISM: Homo sapiens

<400> SEQUENCE: 30
ggcaaatgct ggacccaaca caaa                                          24

<210> SEQ ID NO 31
<211> LENGTH: 24
<212> TYPE: DNA
<213> ORGANISM: Homo sapiens

<400> SEQUENCE: 31
ctaggcatgg gagggaacaa ggaa                                          24

<210> SEQ ID NO 32
<211> LENGTH: 21
<212> TYPE: DNA
<213> ORGANISM: Homo sapiens

<400> SEQUENCE: 32
gactgggctg cgtgctcatc c                                             21

<210> SEQ ID NO 33
<211> LENGTH: 24
<212> TYPE: DNA
<213> ORGANISM: Homo sapiens

<400> SEQUENCE: 33
aggccctgtg gtcactcata ctgc                                          24

<210> SEQ ID NO 34
<211> LENGTH: 20
<212> TYPE: DNA
<213> ORGANISM: Homo sapiens

<400> SEQUENCE: 34
aggggctaac aatggacacc                                               20

<210> SEQ ID NO 35
<211> LENGTH: 22
<212> TYPE: DNA
<213> ORGANISM: Homo sapiens

<400> SEQUENCE: 35
ccgaagataa gggggaacta ct                                            22

<210> SEQ ID NO 36
<211> LENGTH: 21
<212> TYPE: DNA
<213> ORGANISM: Homo sapiens

<400> SEQUENCE: 36
ccggcgggag gcaggaggag t                                             21

<210> SEQ ID NO 37
```

```
<211> LENGTH: 24
<212> TYPE: DNA
<213> ORGANISM: Homo sapiens

<400> SEQUENCE: 37
gcggcggtag gtcaggcagt tgtc                                              24

<210> SEQ ID NO 38
<211> LENGTH: 20
<212> TYPE: DNA
<213> ORGANISM: Homo sapiens

<400> SEQUENCE: 38
tgcgaagctg cttcaccgat                                                   20

<210> SEQ ID NO 39
<211> LENGTH: 21
<212> TYPE: DNA
<213> ORGANISM: Homo sapiens

<400> SEQUENCE: 39
ggccgtacat gcactccact g                                                 21

<210> SEQ ID NO 40
<211> LENGTH: 22
<212> TYPE: DNA
<213> ORGANISM: Homo sapiens

<400> SEQUENCE: 40
gtgaagtcgg gacgttttgt ga                                                22

<210> SEQ ID NO 41
<211> LENGTH: 21
<212> TYPE: DNA
<213> ORGANISM: Homo sapiens

<400> SEQUENCE: 41
ccgtggtggg gccctttgtg g                                                 21

<210> SEQ ID NO 42
<211> LENGTH: 20
<212> TYPE: DNA
<213> ORGANISM: Homo sapiens

<400> SEQUENCE: 42
cttgttacag agtatggtgt                                                   20

<210> SEQ ID NO 43
<211> LENGTH: 20
<212> TYPE: DNA
<213> ORGANISM: Homo sapiens

<400> SEQUENCE: 43
gtctgttcag gtataaaccc                                                   20

<210> SEQ ID NO 44
<211> LENGTH: 20
<212> TYPE: DNA
<213> ORGANISM: Homo sapiens

<400> SEQUENCE: 44
cctcctgtag tgcttcaccg                                                   20
```

```
<210> SEQ ID NO 45
<211> LENGTH: 20
<212> TYPE: DNA
<213> ORGANISM: Homo sapiens

<400> SEQUENCE: 45
cctcctgtag gtggacggcc                                              20

<210> SEQ ID NO 46
<211> LENGTH: 20
<212> TYPE: DNA
<213> ORGANISM: Homo sapiens

<400> SEQUENCE: 46
aacactgaag attgtgaaga                                              20

<210> SEQ ID NO 47
<211> LENGTH: 20
<212> TYPE: DNA
<213> ORGANISM: Homo sapiens

<400> SEQUENCE: 47
cttttggaag gagtttcgga                                              20

<210> SEQ ID NO 48
<211> LENGTH: 20
<212> TYPE: DNA
<213> ORGANISM: Homo sapiens

<400> SEQUENCE: 48
ctccccacag caactgcctg                                              20

<210> SEQ ID NO 49
<211> LENGTH: 20
<212> TYPE: DNA
<213> ORGANISM: Homo sapiens

<400> SEQUENCE: 49
tgctccacag ggcgacccca                                              20

<210> SEQ ID NO 50
<211> LENGTH: 20
<212> TYPE: DNA
<213> ORGANISM: Homo sapiens

<400> SEQUENCE: 50
ttctgctcag tttttatggc                                              20

<210> SEQ ID NO 51
<211> LENGTH: 20
<212> TYPE: DNA
<213> ORGANISM: Homo sapiens

<400> SEQUENCE: 51
tgccgtgagg gtgagcgcgc                                              20

<210> SEQ ID NO 52
<211> LENGTH: 20
<212> TYPE: DNA
<213> ORGANISM: Homo sapiens

<400> SEQUENCE: 52
tatgcgaagc gtgagtgaat                                              20
```

-continued

```
<210> SEQ ID NO 53
<211> LENGTH: 20
<212> TYPE: DNA
<213> ORGANISM: Homo sapiens

<400> SEQUENCE: 53
tacacctgcc gtatgtacct                                               20

<210> SEQ ID NO 54
<211> LENGTH: 20
<212> TYPE: DNA
<213> ORGANISM: Homo sapiens

<400> SEQUENCE: 54
gaacgtggtg gtaagtcccg                                               20

<210> SEQ ID NO 55
<211> LENGTH: 20
<212> TYPE: DNA
<213> ORGANISM: Homo sapiens

<400> SEQUENCE: 55
ccacatccag gtgtgtgcag                                               20

<210> SEQ ID NO 56
<211> LENGTH: 20
<212> TYPE: DNA
<213> ORGANISM: Homo sapiens

<400> SEQUENCE: 56
gaggcaggag gtgagcccac                                               20

<210> SEQ ID NO 57
<211> LENGTH: 20
<212> TYPE: DNA
<213> ORGANISM: Homo sapiens

<400> SEQUENCE: 57
gtcagtacga gtgagtgcgg                                               20

<210> SEQ ID NO 58
<211> LENGTH: 20
<212> TYPE: DNA
<213> ORGANISM: Homo sapiens

<400> SEQUENCE: 58
caagatcacg gtgagtggcg                                               20

<210> SEQ ID NO 59
<211> LENGTH: 19
<212> TYPE: DNA
<213> ORGANISM: Homo sapiens

<400> SEQUENCE: 59
gcaggatgtg gtaaggatg                                                19

<210> SEQ ID NO 60
<211> LENGTH: 19
<212> TYPE: DNA
<213> ORGANISM: Homo sapiens

<400> SEQUENCE: 60
gcgctggagc gtgcgcaca                                                19
```

```
<210> SEQ ID NO 61
<211> LENGTH: 18
<212> TYPE: DNA
<213> ORGANISM: Homo sapiens

<400> SEQUENCE: 61 ggtcggggc ggcttgtg                                                    18

<210> SEQ ID NO 62
<211> LENGTH: 21
<212> TYPE: DNA
<213> ORGANISM: Homo sapiens

<400> SEQUENCE: 62
ctgtcgcgtt atgagttgtt g                                               21

<210> SEQ ID NO 63
<211> LENGTH: 20
<212> TYPE: DNA
<213> ORGANISM: Homo sapiens

<400> SEQUENCE: 63
aggcattggg tcgtattcac                                                 20

<210> SEQ ID NO 64
<211> LENGTH: 19
<212> TYPE: DNA
<213> ORGANISM: Homo sapiens

<400> SEQUENCE: 64
ggcacgctgg gtctaacac                                                  19

<210> SEQ ID NO 65
<211> LENGTH: 21
<212> TYPE: DNA
<213> ORGANISM: Homo sapiens

<400> SEQUENCE: 65
ctcatggacc tttgcccatc t                                               21

<210> SEQ ID NO 66
<211> LENGTH: 21
<212> TYPE: DNA
<213> ORGANISM: Homo sapiens

<400> SEQUENCE: 66
gtgatggact ctgttcctca c                                               21

<210> SEQ ID NO 67
<211> LENGTH: 21
<212> TYPE: DNA
<213> ORGANISM: Homo sapiens

<400> SEQUENCE: 67
cacagcctcc tgtcatatgg a                                               21

<210> SEQ ID NO 68
<211> LENGTH: 19
<212> TYPE: DNA
<213> ORGANISM: Homo sapiens

<400> SEQUENCE: 68
```

```
ggcgttctca gtcctgcct                                          19

<210> SEQ ID NO 69
<211> LENGTH: 19
<212> TYPE: DNA
<213> ORGANISM: Homo sapiens

<400> SEQUENCE: 69
ctggcctgag ccctgctga                                          19

<210> SEQ ID NO 70
<211> LENGTH: 19
<212> TYPE: DNA
<213> ORGANISM: Homo sapiens

<400> SEQUENCE: 70
caatgagctc tcccgcatc                                          19

<210> SEQ ID NO 71
<211> LENGTH: 20
<212> TYPE: DNA
<213> ORGANISM: Homo sapiens

<400> SEQUENCE: 71
agaatgctgt acgtggcgtg                                         20

<210> SEQ ID NO 72
<211> LENGTH: 19
<212> TYPE: DNA
<213> ORGANISM: Homo sapiens

<400> SEQUENCE: 72
agctcgggcg gcagctcca                                          19

<210> SEQ ID NO 73
<211> LENGTH: 18
<212> TYPE: DNA
<213> ORGANISM: Homo sapiens

<400> SEQUENCE: 73
gcctccacct ggcaggga                                           18

<210> SEQ ID NO 74
<211> LENGTH: 23
<212> TYPE: DNA
<213> ORGANISM: Homo sapiens

<400> SEQUENCE: 74
gtacaaagtt aatcatggat ggt                                     23

<210> SEQ ID NO 75
<211> LENGTH: 20
<212> TYPE: DNA
<213> ORGANISM: Homo sapiens

<400> SEQUENCE: 75
agaagccaaa gctcgcagga                                         20

<210> SEQ ID NO 76
<211> LENGTH: 19
<212> TYPE: DNA
<213> ORGANISM: Homo sapiens

<400> SEQUENCE: 76
```
cctgcccgtg cacagacct                                                19

<210> SEQ ID NO 77
<211> LENGTH: 21
<212> TYPE: DNA
<213> ORGANISM: Homo sapiens

<400> SEQUENCE: 77
gtctgcagct gagaatagca c                                             21

<210> SEQ ID NO 78
<211> LENGTH: 21
<212> TYPE: DNA
<213> ORGANISM: Homo sapiens

<400> SEQUENCE: 78
aggtccgcac catatgaaca c                                             21

<210> SEQ ID NO 79
<211> LENGTH: 19
<212> TYPE: DNA
<213> ORGANISM: Homo sapiens

<400> SEQUENCE: 79
accccagcac cgagcagga                                                19

<210> SEQ ID NO 80
<211> LENGTH: 19
<212> TYPE: DNA
<213> ORGANISM: Homo sapiens

<400> SEQUENCE: 80
ccctgactcc acagcccac                                                19

<210> SEQ ID NO 81
<211> LENGTH: 19
<212> TYPE: DNA
<213> ORGANISM: Homo sapiens

<400> SEQUENCE: 81
accctctcgc gcacctcca                                                19

<210> SEQ ID NO 82
<211> LENGTH: 19
<212> TYPE: DNA
<213> ORGANISM: Homo sapiens

<400> SEQUENCE: 82
ccatgctgtc ccaccttca                                                19

<210> SEQ ID NO 83
<211> LENGTH: 20
<212> TYPE: DNA
<213> ORGANISM: Homo sapiens

<400> SEQUENCE: 83
aggaggtgag ggactgaatg                                               20

<210> SEQ ID NO 84
<211> LENGTH: 47
<212> TYPE: PRT
<213> ORGANISM: Homo sapiens

```
<400> SEQUENCE: 84

Arg Cys Ser Leu Leu Glu Leu Pro Pro Glu Leu Leu Val Glu Ile Phe
1               5                   10                  15

Ala Ser Leu Pro Gly Thr Asp Leu Pro Ser Leu Ala Gln Val Cys Thr
            20                  25                  30

Lys Phe Arg Arg Ile Leu His Thr Asp Thr Ile Trp Arg Arg Arg
        35                  40                  45

<210> SEQ ID NO 85
<211> LENGTH: 50
<212> TYPE: PRT
<213> ORGANISM: Homo sapiens

<400> SEQUENCE: 85

Lys Pro Phe Pro Leu Leu Arg Leu Pro Glu Glu Ile Leu Arg Lys Ile
1               5                   10                  15

Leu Glu Lys Leu Asp Pro Ile Asp Leu Leu Arg Leu Arg Lys Val Ser
            20                  25                  30

Lys Lys Trp Arg Ser Leu Val Asp Ser Leu Asn Ile Trp Phe Lys Phe
        35                  40                  45

Ile Glu
    50
```